US012806189B2

(12) United States Patent
Mounir et al.

(10) Patent No.: US 12,806,189 B2
(45) Date of Patent: Nov. 24, 2026

(54) PHARMACEUTICAL COMBINATION AND TUMOR TREATMENT

(71) Applicant: IDEAYA Biosciences, Inc., South San Francisco, CA (US)

(72) Inventors: Zineb Mounir, Pacifica, CA (US); Marie-Claire Wagle, Burlingame, CA (US); Nandini Ravindran, South San Francisco, CA (US); Divya Pankajakshan, Daly City, CA (US); Mark R. Lackner, San Mateo, CA (US)

(73) Assignee: IDEAYA Biosciences, Inc., South San Francisco, CA (US)

( * ) Notice: Subject to any disclaimer, the term of this patent is extended or adjusted under 35 U.S.C. 154(b) by 402 days.

(21) Appl. No.: 18/043,298

(22) PCT Filed: Sep. 7, 2021

(86) PCT No.: PCT/US2021/049310
§ 371 (c)(1),
(2) Date: May 23, 2023

(87) PCT Pub. No.: WO2022/055893
PCT Pub. Date: Mar. 17, 2022

(65) Prior Publication Data

US 2025/0017921 A1 Jan. 16, 2025

Related U.S. Application Data

(60) Provisional application No. 63/075,702, filed on Sep. 8, 2020.

(51) Int. Cl.

| | |
|---|---|
| ***A61K 31/497*** | (2006.01) |
| ***A61K 31/4545*** | (2006.01) |
| ***A61P 35/04*** | (2006.01) |
| ***C12Q 1/6886*** | (2018.01) |
| ***G01N 33/5751*** | (2026.01) |

(52) U.S. Cl.
CPC ........ *A61K 31/497* (2013.01); *A61K 31/4545* (2013.01); *A61P 35/04* (2018.01); *C12Q 1/6886* (2013.01); *G01N 33/5751* (2026.01); *C12Q 2600/106* (2013.01); *C12Q 2600/156* (2013.01)

(58) Field of Classification Search
CPC ... A61K 31/497; A61K 31/4545; A61P 35/04; C12Q 1/6886; C12Q 2600/106; C12Q 2600/156; G01N 33/5743
See application file for complete search history.

(56) References Cited

U.S. PATENT DOCUMENTS

| | | | |
|---|---|---|---|
| 6,645,970 | B2 | 11/2003 | Albert et al. |
| 7,758,891 | B2 | 7/2010 | Desai et al. |
| 7,777,050 | B2 | 8/2010 | Wallace et al. |
| 8,460,743 | B2 | 6/2013 | Mueller et al. |
| 8,501,404 | B2 | 8/2013 | Bastian et al. |
| 8,592,455 | B2 | 11/2013 | Burger et al. |
| 8,703,962 | B2 | 4/2014 | Kyle et al. |
| 8,822,497 | B2 | 9/2014 | Burger et al. |
| 8,829,193 | B2 | 9/2014 | Burger et al. |
| 8,927,215 | B2 | 1/2015 | Bastian et al. |
| 8,946,235 | B2 | 2/2015 | Butterworth et al. |
| 9,452,998 | B2 | 9/2016 | Visser et al. |
| 9,845,309 | B2 | 12/2017 | Luzzio et al. |
| 9,963,700 | B2 | 5/2018 | Gollob et al. |
| 10,508,101 | B2 | 12/2019 | Luzzio et al. |
| 2006/0052396 | A1 | 3/2006 | Berg et al. |
| 2010/0120862 | A1 | 5/2010 | Tafesse |
| 2010/0267742 | A1 | 10/2010 | Plate |
| 2011/0130415 | A1 | 6/2011 | Singh et al. |
| 2012/0076272 | A1 | 3/2012 | Gertner et al. |
| 2012/0208815 | A1 | 8/2012 | Burger et al. |
| 2012/0225062 | A1 | 9/2012 | Burger et al. |
| 2013/0023497 | A1 | 1/2013 | Tao et al. |
| 2013/0109682 | A1 | 5/2013 | Burger et al. |
| 2014/0295452 | A1 | 10/2014 | Goetsch |
| 2015/0306101 | A1 | 10/2015 | Porter et al. |
| 2016/0046605 | A1 | 2/2016 | Visser et al. |
| 2016/0347737 | A1 | 12/2016 | Luzzio et al. |

(Continued)

FOREIGN PATENT DOCUMENTS

| | | | |
|---|---|---|---|
| AU | 2015298364 | A1 | 2/2017 |
| AU | 2015298364 | B2 | 8/2018 |

(Continued)

OTHER PUBLICATIONS

"International Application Serial No. PCT US2021 049310, International Preliminary Report on Patentability mailed Mar. 23, 2023", 7 pgs.
"Israeli Application Serial No. 300952, Notification Prior to Examination mailed Sep. 27, 2023", w English Translation, 5 pgs.
"Mexican Application Serial No. MX a 2023 002757 , Voluntary Amendment Filed May 20, 2024", w English Claims, 24 pgs.
"European Application Serial No. 21867451.3, Extended European Search Report mailed Jul. 31, 2024", 9 pgs.
"Japanese Application Serial No. 2023-515183, Voluntary Amendment filed Sep. 6, 2024", w English claims, 11 pgs.
"Brazilian Application Serial No. BR112023003911-8, Voluntary Amendment filed Sep. 5, 2024", w English claims, 166 pgs.

(Continued)

*Primary Examiner* — Kamal A Saeed
*Assistant Examiner* — Quincy Mckoy
(74) *Attorney, Agent, or Firm* — Goodwin Procter LLP

(57) ABSTRACT

A combination therapy is described involving a selective protein kinase C inhibitor and a cMET inhibitor, which is useful for treating metastatic uveal melanoma and other proliferative diseases, such as a tumor having a GNAQ or GNA11 mutation. The combination therapy can be provided by a pharmaceutical product, a method of treatment, or a kit. The combination therapy can involve use of a protein kinase C inhibitor and a cMET inhibitor. Also provided are methods useful for selecting patients or directing a course of treatment. In various examples, the protein kinase C can have the structure according to Formula II.

7 Claims, 44 Drawing Sheets

(56) References Cited

U.S. PATENT DOCUMENTS

| | | | |
|---|---|---|---|
| 2017/0039328 | A1 | 2/2017 | Kathleen et al. |
| 2017/0320853 | A1 | 11/2017 | Dandu et al. |
| 2018/0179181 | A1 | 6/2018 | Luzzio et al. |
| 2018/0243293 | A1 | 8/2018 | Halilovic et al. |
| 2019/0202809 | A1 | 7/2019 | Luzzio et al. |
| 2020/0262814 | A1 | 8/2020 | Luzzio et al. |
| 2020/0268749 | A1 | 8/2020 | Cooke et al. |
| 2020/0323863 | A1 | 10/2020 | Gutkind et al. |
| 2021/0230154 | A1 | 7/2021 | Vaswani et al. |
| 2021/0387962 | A1 | 12/2021 | Luzzio et al. |
| 2022/0079940 | A1 | 3/2022 | Centore et al. |
| 2022/0305008 | A1 | 9/2022 | Knox et al. |
| 2022/0323436 | A1 | 10/2022 | Cooke et al. |
| 2022/0401440 | A1 | 12/2022 | Hambleton et al. |
| 2024/0207257 | A1 | 6/2024 | Maurer et al. |
| 2024/0335440 | A1 | 10/2024 | Maurer et al. |
| 2025/0248996 | A1 | 8/2025 | Cooke et al. |

FOREIGN PATENT DOCUMENTS

| | | | |
|---|---|---|---|
| CA | 2956996 | A1 | 2/2016 |
| CN | 101679266 | A | 3/2010 |
| CN | 101801958 | A | 8/2010 |
| CN | 102317469 | A | 1/2012 |
| CN | 102482265 | A | 5/2012 |
| CN | 102821759 | A | 12/2012 |
| CN | 103080106 | A | 5/2013 |
| EP | 2178861 | B1 | 8/2014 |
| EP | 3177608 | A1 | 6/2017 |
| IN | 202317026268 | | 11/2023 |
| JP | 2010520228 | A | 6/2010 |
| JP | 2012529512 | A | 11/2012 |
| JP | 2013512281 | A | 4/2013 |
| JP | 2013231049 | A | 11/2013 |
| JP | 2014506917 | A | 3/2014 |
| JP | 2023541011 | | 9/2023 |
| WO | WO-0105390 | A2 | 1/2001 |
| WO | WO-0155115 | A1 | 8/2001 |
| WO | WO-0238561 | A1 | 5/2002 |
| WO | WO-03004472 | A1 | 1/2003 |
| WO | WO-03004475 | A1 | 1/2003 |
| WO | WO-03077914 | A1 | 9/2003 |
| WO | WO-2004055005 | A1 | 7/2004 |
| WO | WO-2004096795 | A2 | 11/2004 |
| WO | WO-2005079802 | A1 | 9/2005 |
| WO | WO-2006018280 | A2 | 2/2006 |
| WO | WO-2006045010 | A2 | 4/2006 |
| WO | WO-2006048771 | A1 | 5/2006 |
| WO | WO-2008002247 | A1 | 1/2008 |
| WO | WO-2008106692 | A1 | 9/2008 |
| WO | WO-2009014637 | A2 | 1/2009 |
| WO | WO-2009082346 | A1 | 7/2009 |
| WO | WO-2009143211 | A2 | 11/2009 |
| WO | WO-2010026124 | A1 | 3/2010 |
| WO | WO-2010046780 | A2 | 4/2010 |
| WO | WO-2010071837 | A1 | 6/2010 |
| WO | WO-2010075380 | A1 | 7/2010 |
| WO | WO-2011012661 | A1 | 2/2011 |
| WO | WO-2011018454 | A1 | 2/2011 |
| WO | WO-2011068898 | A1 | 6/2011 |
| WO | WO-2011076786 | A1 | 6/2011 |
| WO | WO-2011130691 | A2 | 10/2011 |
| WO | WO-2012004217 | A1 | 1/2012 |
| WO | WO-2012066095 | A1 | 5/2012 |
| WO | WO-2012101064 | A1 | 8/2012 |
| WO | WO-2012120415 | A1 | 9/2012 |
| WO | WO-2012129562 | A2 | 9/2012 |
| WO | WO-2012080729 | A4 | 11/2012 |
| WO | WO-2013111105 | A1 | 8/2013 |
| WO | WO-2013175388 | A1 | 11/2013 |
| WO | WO-2014012511 | A1 | 1/2014 |
| WO | WO-2014099880 | A1 | 6/2014 |
| WO | WO-2014174478 | A1 | 10/2014 |
| WO | WO-2014181287 | A1 | 11/2014 |
| WO | WO-2016020864 | A1 | 2/2016 |
| WO | WO-2017029588 | A2 | 2/2017 |
| WO | WO-2019053595 | A1 | 3/2019 |
| WO | WO-2020146355 | A1 | 7/2020 |
| WO | WO-2020198469 | A1 | 10/2020 |
| WO | WO-2021102004 | A1 | 5/2021 |
| WO | WO-2021155235 | A1 | 8/2021 |
| WO | WO-2022055893 | A1 | 3/2022 |
| WO | WO-2022221586 | A1 | 10/2022 |
| WO | WO-2023107894 | A1 | 6/2023 |
| WO | WO-2024044774 | A2 | 2/2024 |
| WO | WO-2024044775 | A1 | 2/2024 |
| WO | WO-2024220839 | A1 | 10/2024 |
| WO | WO-2025042981 | A2 | 2/2025 |
| WO | WO-2025240628 | A1 | 11/2025 |

OTHER PUBLICATIONS

"2011 International Melanoma Congress: Advancement Through Collaboration", Pigment Cell Res., 24(5), (Oct. 10, 2011), 990-1075.

"International Application Serial No. PCT/IB2014/060976, International Search Report mailed Aug. 4, 2014", 4 pgs.

"International Application Serial No. PCT/IB2014/060976, Written Opinion mailed Aug. 4, 2014", 4 pgs.

"International Application Serial No. PCT/IB2014/060976, Written Opinion mailed Oct. 27, 2015", 5 pgs.

"International Application Serial No. PCT/US2021/049310, International Search Report mailed Dec. 13, 2021", 2 pgs.

"International Application Serial No. PCT/US2021/049310, Written Opinion mailed Dec. 13, 2021", 5 pgs.

Baltschukat, Sabrina, et al., "Capmatinib (INC280) Is Active Against Models of Non-Small Cell Lung Cancer and Other Cancer Types with Defined Mechanisms of MET Activation", Clin Cancer Res; 25(10), (May 15, 2019), 13 pgs.

Carita, Guillaume, et al., "Dual inhibition of protein kinase C and p53-MDM2 or PKC and mTORC1 are novel efficient therapeutic approaches for uveal melanoma", Oncotarget, 7(23), (2016), 33542-33546.

Chen, Xu, et al., "Combined PKC and MEK inhibition in uveal melanoma with GNAQ and GNA11 mutations", Oncogene, 33(39), (Sep. 2014), 23 pgs.

Chen, Xu, et al., "RasGRP3 Mediates MAPK Pathway Activation in GNAQ Mutant Uveal Melanoma", Cancer Cell, 31(5), (May 8, 2017), 19 pgs.

Cheng, Hanyin, et al., "Co-targeting HGF/cMET Signaling with MEK Inhibitors in Metastatic Uveal Melanoma", Mol Cancer Ther; 16(3), (Mar. 2017), 14 pgs.

Cooke, Mariana, et al., "Protein Kinase C in Cancer: The Top Five Unanswered Questions", Mol Carcinog, 56(6), pp. 1531-1542, (2017), 22 pgs.

Croce, Michela, et al., "Targeted Therapy of Uveal Melanoma: Recent Failures and New Perspectives", Cancers, 11, (2019), 21 pgs.

Garg, Rachana, et al., "Protein kinase C and cancer: what we know and what we do not", Oncogene, 33(45), pp. 5225-5237, (2014), 34 pgs.

Grossoni, Valeria C, et al., "Opposite effects of protein kinase C beta1 (PKCb1) and PKCe in the metastatic potential of a breast cancer murine model", Breast Cancer Res Treat, 118(3), (2009), 469-480.

Heijkants, R C, et al., "Targeting MDMX and PKCDelta to improve current uveal melanoma therapeutic strategies", Oncogenesis, 7(3), (2018), 11 pgs.

Kang, Jeong-Hun, et al., "Protein Kinase C (PKC) Isozymes and Cancer", Hindawi Publishing Corp., New Journal of Science, vol. 2014, Art. 231418, (2014), 17 pgs.

Kermorgant, Stephanie, et al., "PKC controls HGF-dependent c-Met traffic, signalling and cell migration", The EMBO Journal, 23(19), (2004), 3721-3734.

Khan, Shaheer, et al., "Adjuvant crizotinib in highrisk uveal melanoma following definitive therapy (Abstract only)", Journal of Clinical Oncology, 38(15), suppl., [Online] Retrieved from the Internet: <URL: https://ascopubs.org/doi/abs/10.1200/JCO.2020.38.15_suppl. 10075>, (May 20, 2020), 5 pgs.

(56) References Cited

OTHER PUBLICATIONS

Mattoo, Abid R, et al., "Combination Treatments with the PKC Inhibitor, Enzastaurin, Enhance the Cytotoxicity of the Anti-Mesothelin Immunotoxin, SS1P", Plos One, 8(10), (Oct. 2013), 9 pgs.
Musi, Elgilda, et al., "The Phosphoinositide 3-Kinase a Selective Inhibitor BYL719 Enhances the Effect of the Protein Kinase C Inhibitor AEB071 in GNAQ/GNA11-Mutant Uveal Melanoma Cells", Mol Cancer Ther; 13(5), (May 2014), 12 pgs.
Naylor, Tara L., et al., "Protein Kinase C Inhibitor Sotrastaurin Selectively Inhibits the Growth of CD79 Mutant Diffuse Large B-Cell Lymphomas", Cancer Research, 71(7), (2011), 2643-2653.
Spigel, David R, et al., "Treatment Rationale Study Design for the MetLung Trial: A Randomized, Double-Blind Phase III Study of Onartuzumab (MetMAb) in Combination With Erlotinib Versus Erlotinib Alone in Patients Who Have Received Standard Chemotherapy for Stage IIIB or IV Met-Pos", Clinical Lung Cancer, 13(6), (2012), 500-504.
Surriga, Oliver, et al., "Crizotinib, a c-Met Inhibitor, Prevents Metastasis in a Metastatic Uveal Melanoma Model", Molecular Cancer Therapeutics, 12(12), (2013), 2817-2826.
Wilson, Frederick H, et al., "A Functional Landscape of Resistance to ALK Inhibition in Lung Cancer", Cancer Cell, 27(3), (Mar. 9, 2015), 25 pgs.
Wu, Xinqi, et al., "Protein kinase C inhibitor AEB071 targets ocular melanoma harboring GNAQ mutations via effects on the PKC/Erk1/2 and PKC/NF-kappaB pathways", Mol Cancer Ther., 11(9), (Sep. 2012), 1905-1914.
Wu, Xinqi, et al., "The Protein Kinase C Inhibitor Enzastaurin Exhibits Antitumor Activity against Uveal Melanoma", Plos One, 7(1): e29622, (2012), 10 pgs.
Xu, Yingying, et al., "Expression and clinical significance of c-Met in advanced esophageal squamous cell carcinoma", BMC Cancer, 15(6), (2015), 7 pgs.
"Mexican Application Serial No. MX a 2023 002757, Voluntary Amendment Filed Oct. 21, 2024", w English claims, 34 pgs.
"European Application Serial No. 21867451.3, Response filed Feb. 20, 2025 to Extended European Search Report mailed Jul. 31, 2024", 10 pgs.
"A Phase I Study of LXS196 in Patients with Metastatic Uveal Melanoma", Novartis Pharmaceuticals, (Nov. 10, 2015), 16 pages.
"European Application 21867451.3, Communication Under Rule 71.3 Feb. 5, 2026", 9 pages.
"European Application Serial No. 20891385.5, Extended European Search Report mailed Aug. 17, 2023", 9 pgs.
"European Application Serial No. 21867451.3, Communication Pursuant to Article 94(3) EPC mailed Aug. 6, 2025", 6 pgs.
"European Application Serial No. 21867451.3, Response filed Dec. 5, 2025 to Communication Pursuant to Article 94(3) EPC mailed Aug. 6, 2025", 180 pgs.
"IDEAYA Biosciences Common Stock Prospectus", IDEAYA Biosciences, Inc., (May 22, 2019), 3 pgs.
"International Application Serial No. PCT/IB2015/055951, International Search Report mailed Sep. 11, 2015", 4 pgs.
"International Application Serial No. PCT/IB2015/055951, Written Opinion mailed Sep. 11, 2015", 7 pgs.
"International Application Serial No. PCT/IB2018/056945, International Search Report mailed Jan. 3, 2019", 4 pgs.
"International Application Serial No. PCT/IB2018/056945, Written Opinion mailed Jan.. 3, 2019", 8 pgs.
"International Application Serial No. PCT/US2020/012542, International Search Report mailed May 4, 2020", 5 pgs.
"International Application Serial No. PCT/US2020/012542, Written Opinion mailed May 4, 2020", 6 pgs.
"International Application Serial No. PCT/US2020/061056, International Search Report mailed May 17, 2021", 6 pgs.
"International Application Serial No. PCT/US2020/061056, Written Opinion mailed May 17, 2021", 13 pgs.
"International Application Serial No. PCT/US2022/024909, International Search Report mailed Jul. 7, 2022", 3 pgs.
"International Application Serial No. PCT/US2022/024909, Written Opinion mailed Jul. 7, 2022", 7 pgs.
"International Application Serial No. PCT/US2022/080928, International Search Report mailed Mar. 9, 2023", 3 pgs.
"International Application Serial No. PCT/US2022/080928, Written Opinion mailed Mar. 9, 2023", 74 pgs.
"International Application Serial No. PCT/US2023/072953, International Search Report mailed Jan. 23, 2024", 3 pgs.
"International Application Serial No. PCT/US2023/072953, Written Opinion mailed Jan. 23, 2024", 6 pgs.
"International Application Serial No. PCT/US2023/072954, International Search Report mailed Feb. 7, 2024", 4 pgs.
"International Application Serial No. PCT/US2023/072954, Written Opinion mailed Feb. 7, 2024", 6 pgs.
"Japanese Application Serial No. 2023-515183, Notification of Reasons for Rejection mailed Oct. 7, 2025", W/English Translation, 6 pgs.
"Myfortic®", FDA Label, (2008).
"Pubchem SID: 104161043", SUBSTANCE (R)-3-(1-(2,6-dichloro-3-fluorophenyl)ethoxy)-5-(1-(piperidin-4-yl)-1H-pyrazol-4-yl)pyridin-2-amine, (Jan. 21, 2011), 4 pgs.
"Pubchem SID: 374358302", SUBSTANCE Darovasertib, (Jun. 6, 2018), 4 pgs.
Abera, Mahlet B., et al., "Protein Kinase C-alpha Mediates Erlotinib Resistance in Lung Cancer Cells", Molecular Pharmacology, 87(5), (May 2015), 832-841.
Abuhammad, S., et al., "Inhibition of the protein arginine methyltransferase PRMTS overcomes resistance to CDK4-inhibition in melanoma", SMR Congress 2017 Abstracts, Pigment Cell & Melanoma Research 31(1), (Jan. 2018), 125-230.
Ahn, N. G., et al., "Pharmacologic Inhibitors of MKK1 and MKK2", Methods in Enzymology, vol. 33, (2001), 15 pgs.
Amnon, Altman, et al., "Protein kinase C inhibitors for immune disorders", Drug Discovery Today 19, (2014), 1217-1221.
Ayturk, Ugur M, et al., "Somatic Activating Mutations in GNAQ and GNA11 Are Associated with Congenital Hemangioma", The American Journal of Human Genetics 98, (Apr. 7, 2016), 789-795.
Berge, Stephen M, et al., "Pharmaceutical Salts", Journal of Pharmaceutical Sciences, 66(1), (Jan. 1977), 1-19.
Budde, K., et al., "Sotrastaurin, a Novel Small Molecule Inhibiting Protein Kinase C: First Clinical Results in Renal-Transplant Recipients", American Journal of Transplantation 10, (2010), 571-581.
Chapman, Jeremy R., et al., "Cancer in the Transplant Recipient", Cold Spring Harbor Perspectives in Medicine, 3:a015677, (2013), 15 pgs.
Chou, T. C., et al., "Quantitative analysis of dose-effect relationships: the combined effects of multiple drugs or enzyme inhibitors", Advances in Enzyme Regulation, 22, (1984), 27-55.
Davies, L., et al., "PERP expression stabilizes active p53 via modulation of p53-MDM2 interaction in uveal melanoma cells", Cell Death and Disease 2, e136, (2011), 11 pgs.
De Lange J., et al., "Synergistic growth inhibition based on small-molecule p53 activation as treatment for intraocular melanoma", Oncogene 31, (2012), 1105-1116.
Frey, Christian R, et al., "Analysis of drug combinations with the PKC inhibitor IDE196 support dual MEK and PKC inhibition as a rational combination in metastatic uveal melanoma", Cancer Res 80, (2020), 2 pgs.
Gamsizkan, M., et al., "Mutation analysis of metastatic melanomas in the central nervous system: results of a panel of 5 genes in 48 cases", Clin Neuropathol.35(4), (2016), 178-185.
Gura, T., "Systems for Identifying New Drugs Are Often Faulty", Science, 278, (1997), 1041-1042.
Harbour, William J., et al., "The genetics of uveal melanoma: an emerging framework for targeted therapy", Pigment Cell Melanoma Res. 25(2), (Mar. 2012), 171-181.
Hayashi, Keitaro, et al., "Protein kinase C theta (PKC8): A key player in T cell life and death", Pharmacological Research 55, (2007), 537-544.
Holford, Nicholas H.G., et al., "Understanding the Dose-Effect Relationship: Clinical Application of Pharmacokinetic-Pharmacodynamic Models", Clinical Pharmacokinetics 6, (1981), 429-453.

(56) References Cited

OTHER PUBLICATIONS

Houben, Roland, et al., “High-Level Expression of Wild-Type p53 in Melanoma Cells is Frequently Associated with Inactivity in p53 Reporter Gene Assays”, PloS ONE 6(70):e22096, (2011), 7 pgs.
Huck, R. Bayard, et al., “Small Molecules Drive Big Improvements in Immuno-Oncology Therapies”, Angew. Chem. Int. Ed, 57,, (2018), 4412-4428.
Johnson, et al., “Relationships between drug activity in NCI preclinical in vitro and in vivo models and early clinical trials”, British Journal of Cancer, 84, (2001), 1424-1431.
Johnson, Douglas B, et al., “Comparative analysis of the Gnaq, GNA11, SF3B1, and EIF1AX driver mutations in melanoma and across the cancer spectrum”, Pigment Cell Melanoma Res. 29(4):470-473, (2016), 8 pgs.
Joshua, Anthony, “Neoadjuvant/adjuvant Trial of Darovasertib in Ocular Melanoma (NADOM)”, [Online]. Retrieved from the Internet: <URL: https://classic.clinicaltrials.gov/ct2/show/study/NCT05187884>, Dec. 11, 2023, (Dec. 11, 2013), 11 pgs.
Kaplteijn, Ellers, et al., “A Phase 1 trial of LXS196, a novel PKC inhibitor for metastatic uveal melanoma”, Cancer Res 79, (2019), 5 pgs.
Khan, Shaheer, et al., “Adjuvant crizotinib in high-risk uveal melanoma following definitive therapy”, Front. Oncol. 12, (Aug. 29, 2022).
Kim, CY, et al., “GNAQ mutation in a patient with metastatic mucosal melanoma”, BMC Cancer 14:516, (2014), 4 pgs.
Kusters-Vandevelde, Heidi, et al., “Activating mutations of the GNAQ gene: a frequent event in primary melanocytic neoplasms of the central nervous system”, Acta Neuropathol. 119(3), (2010), 7 pgs.
Kusters-Vandevelde, HV, et al., “Mutations in g protein encoding genes and chromosomal alterations in primary leptomeningeal melanocytic neoplasms”, Pathol Oncol Res. 21(2), (2015), 9 pages.
Kusters-Vandevelde , HV, et al., “Primary melanocytic tumors of the central nervous system: a review with focus on molecular aspects”, Brain Pathol. 25(2), (2015), 18 pages.
Lee, R. Matthew, et al., “Protein kinase C isozymes as potential therapeutic targets in immune disorders”, Expert Opin. Ther. Targeu 12(5), (Apr. 15, 2008), 535-552.
Lee, Sung Hak, et al., “Whole-exome sequencing identified mutational profiles of high-grade colon adenomas”, Oncotarget. 8(4), (2016), 10 pgs.
Lewis, S. Timothy, et al., “Signal Transduction through MAP Kinase Cascades”, Department of Chemistry and Biochemistry, Howard Hughes Medical Institute University of Colorado, Boulder, Colorado 80309, (1998), 49-139.
Loewe, et al., “About combination effects. I. Communication: Aids for the question”, Archives of Experimental Pathology and Pharmacology 114, (1926), 20 Pages.
Loewe, S., et al., “I.Mitteilung: Hilfsmittel der Fragestellung”, Eingegangen am 17. Y., (1926).
Mann, Karen M., et al., “Sleeping Beauty mutagenesis reveals cooperating mutations and pathways in pancreatic adenocarcinoma”, Proc Natl Acad Sci U S A. 109(16), (2012), 8 pgs.
Marwaha, N, et al., “Subcutaneous melanocytoma mimicking a lipoma: a rare presentation of a rare neoplasm with histological, immunohistochemical, cytogenetic and molecular characterization”, J Cutan Pathol. 43(12), (2016), 1186-1196.
Melia, B. M., et al., “Collaborative Ocular Melanoma Study (COMS) Randomized Trial of I-125 Brachytherapy for Medium Choroidal Melanoma”, I. visual acuity after 3 years COMS report No. 16 vol. 108, Issue 2, (Feb. 2001), 348-366.
Milella, Michele, et al., “Therapeutic targeting of the MEK/MAPK signal transduction module in acute myeloid leukemia”, J. Clin. Invest. 108, (2001), 851-859.
Mochly-Rosen, Daria, et al., “Protein kinase C, an elusive therapeutic target?”, Nat Rev Drug Discov. 11(12), (Dec. 2012), 937-957.
Moon, Ki Rang, et al., “Genetic Alterations in Primary Acral Melanoma and Acral Melanocytic Nevus in Korea:Common Mutated Genes Show Distinct Cytomorphological Features”, J Invest Dermatol. 138(4), (2018), 13 pgs.
O’Hayre, Morgan, et al., “The emerging mutational landscape of G proteins and G-protein-coupled receptors in cancer”, Nat Rev Cancer 13(6), (2013), 23 pgs.
Parish, Austin J, et al., “GNAS, GNAQ, and GNA11 alterations in patients with diverse cancers”, Cancer 124(20), (2018), 10 pgs.
Patel, Sapna P., et al., “GNA11 Mutation in a Patient With Cutaneous Origin Melanoma: A Case Report”, Medicine (Baltimore) 95(4):e2336, (2016), 4 pgs.
Patel, Sharmila, et al., “Small-molecule inhibitors of the p53-HDM2 interaction for the treatment of cancer”, Expert Opin. Investig. Drugs 17(12):, (2008), 1865-1882.
Pearce, et al., “Failure modes in anticancer drug discovery and development”, Cancer Drug Design and Discovery, (2008), 424-435.
Piperno-Neumann, S., et al., “A phase I trial of LXS196, a protein kinase C (PKC) inhibitor, for metastatic uveal melanoma”, Pigment Cell & Melanoma Research 31(1):196, (2018), 1 page.
Ren, Ji-Xia, et al., “Discovery of Novel Pim-1 Kinase Inhibitors by a Hierarchical Multistage Virtual Screening Approach Based on SVM Model, Pharmacophore, and Molecular Docking”, Journal of Chemical Information and Modeling. vol. 15, No. 6, (Jun. 27, 2011), 12 pgs.
Russ, G. R., et al., “Efficacy of Sotrastaurin Plus Tacrolimus After De Novo Kidney Transplantation: Randomized, Phase II Trial Results”, American Journal of Transplantation; 13:, (2013), 1746-1756.
Sebolt-Leopold, J. S., et al., “Blockade of the MAP kinase pathway suppresses growth of colon tumors in vivo”, Nature Medicine vol. 5 No. 7, (Jul. 1999), 7 pgs.
Simone, “Oncology: Introduction”, Cecil Textbook of Medicine, 20th Edition, vol. 1, (1996), 1004-1010.
Skvara, Hans, et al., “The PKC inhibitor AEB071 may be a therapeutic option for psoriasis”, J. Clin. Invest. 118, (2008), 3151-3159.
Stewart, R. Jubilee, et al., “Protein kinase C-a mediates epidermal growth factor receptor transactivation in human prostate cancer cells”, Mol Cancer Ther 4 (5), (2005), 726-732.
Theocharides, Constantine, et al., “Metastatic Melanoma to the Urinary Bladder of Ocular Origin Accompanied with Primary Cutaneous Melanoma: Diagnostic Challenge—A Report of a Case”, Case Rep Pathol. 2017:4818537, (2017), 5 pgs.
Tse, J. Y., et al., “Melanoma arising in a nevus of Ito: novel genetic mutations and a review of the literature on cutaneous malignant transformation of dermal melanocytosis”, J Cutan Pathol. 43(1), (2016), 7 pages.
Van De Nes, Johannes, et al., “Targeted next generation sequencing reveals unique mutation profile of primary melanocytic tumors of the central nervous system”, J Neurooncol. 127(3), (2016), 16 pgs.
Vicente, N., et al., “Uveal melanoma: Clinical characteristics, treatment and survival in a series of 500 patients”, Arch Soc Esp Oftalmol 88(11), (Nov. 2013), 6 pgs.
Wagle, et al., “Abstract 1343: Preclinical evaluation of a PKC and MET inhibitor combination in metastatic uveal melanoma”, Cancer Research 81(13-Supplemental):1343, (2021), 1 page.
Wang, Yizhuo, et al., “G protein subunit a q regulates gastric cancer growth via the p53/p21 and MEK/ERK pathways”, Oncol Rep. 37(4), (2017), 6 pgs.
Zilberg, C, et al., “Analysis of clinically relevant somatic mutations in high-risk head and neck cutaneous squamous cell carcinoma”, Mod Pathol. 31(2), (2018), 13 pgs.

IDE-196 [nM]

| HGF [ng/mL] | 0 | 0.64 | 3.2 | 16 | 80 | 400 | 2000 | 10000 |
|---|---|---|---|---|---|---|---|---|
| 0 | 100 +/-0 | 99 +/-5 | 100 +/-7 | 92 +/-3 | 68 +/-6 | 44 +/-3 | 35 +/-3 | 24 +/-1 |
| 0.14 | 101 +/-3 | 104 +/-3 | 113 +/-3 | 98 +/-5 | 77 +/-8 | 53 +/-7 | 45 +/-5 | 35 +/-2 |
| 0.41 | 126 +/-4 | 120 +/-6 | 127 +/-13 | 112 +/-5 | 88 +/-9 | 65 +/-6 | 53 +/-4 | 43 +/-3 |
| 1.23 | 121 +/-11 | 122 +/-8 | 132 +/-2 | 115 +/-6 | 95 +/-10 | 74 +/-4 | 60 +/-4 | 51 +/-6 |
| 3.7 | 141 +/-16 | 139 +/-16 | 139 +/-19 | 133 +/-13 | 123 +/-14 | 93 +/-12 | 76 +/-8 | 63 +/-6 |
| 11.11 | 149 +/-11 | 153 +/-14 | 151 +/-8 | 153 +/-11 | 147 +/-16 | 127 +/-13 | 103 +/-8 | 77 +/-6 |
| 33.33 | 170 +/-11 | 172 +/-6 | 176 +/-11 | 174 +/-6 | 179 +/-9 | 159 +/-15 | 123 +/-5 | 92 +/-6 |
| 100 | 172 +/-9 | 174 +/-4 | 182 +/-11 | 178 +/-4 | 183 +/-3 | 167 +/-5 | 132 +/-7 | 94 +/-5 |

HGF vs. IDE-196 in Mel-202 5k Disp

HSA Synergy and Antagonism
HGF vs. IDE-196 in Mel-202 5k Disp

Loewe Synergy and Antagonism
HGF vs. IDE-196 in Mel-202 5k Disp

Bliss Synergy and Antagonism
HGF vs. IDE-196 in Mel-202 5k Disp

HSA Synergy and Antagonism
HGF vs. IDE-196 in Mel-202 5k Disp

Loewe Synergy and Antagonism
HGF vs. IDE-196 in Mel-202 5k Disp

Bliss Synergy and Antagonism
HGF vs. IDE-196 in Mel-202 5k Disp

IDE-196 [nM]

| HGF [ng/mL] | 0 | 0.64 | 3.2 | 16 | 80 | 400 | 2000 | 10000 |
|---|---|---|---|---|---|---|---|---|
| 0 | 100 +/-0 | 105 +/-9 | 100 +/-5 | 80 +/-1 | 50 +/-2 | 33 +/-0 | 23 +/-1 | 14 +/-1 |
| 0.14 | 105 +/-4 | 115 +/-7 | 109 +/-7 | 92 +/-1 | 59 +/-3 | 35 +/-1 | 26 +/-2 | 17 +/-1 |
| 0.41 | 108 +/-5 | 117 +/-10 | 110 +/-10 | 93 +/-4 | 61 +/-5 | 37 +/-3 | 28 +/-3 | 19 +/-1 |
| 1.23 | 120 +/-7 | 121 +/-1 | 120 +/-6 | 100 +/-2 | 68 +/-2 | 42 +/-2 | 31 +/-1 | 21 +/-1 |
| 3.7 | 111 +/-4 | 120 +/-7 | 115 +/-5 | 100 +/-1 | 70 +/-2 | 48 +/-3 | 34 +/-3 | 21 +/-1 |
| 11.11 | 123 +/-7 | 126 +/-8 | 125 +/-4 | 115 +/-8 | 77 +/-4 | 52 +/-1 | 36 +/-1 | 23 +/-1 |
| 33.33 | 116 +/-9 | 114 +/-6 | 115 +/-7 | 105 +/-8 | 71 +/-4 | 50 +/-3 | 34 +/-0 | 22 +/-1 |
| 100 | 106 +/-10 | 105 +/-14 | 107 +/-16 | 94 +/-14 | 61 +/-8 | 46 +/-1 | 32 +/-3 | 20 +/-2 |

HGF vs. IDE-196 in 92.1 2.5k Disp

HSA Synergy and Antagonism
HGF vs. IDE-196 in 92.1 2.5k Disp

Loewe Synergy and Antagonism
HGF vs. IDE-196 in 92.1 2.5k Disp

Bliss Synergy and Antagonism
HGF vs. IDE-196 in 92.1 2.5k Disp

HSA Synergy and Antagonism
HGF vs. IDE-196 in 92.1 2.5k Disp

Loewe Synergy and Antagonism
HGF vs. IDE-196 in 92.1 2.5k Disp

Bliss Synergy and Antagonism
HGF vs. IDE-196 in 92.1 2.5k Disp

IDE-196 [nM]

| HGF [ng/mL] | 0 | 0.64 | 3.2 | 16 | 80 | 400 | 2000 | 10000 |
|---|---|---|---|---|---|---|---|---|
| 0 | 100 +/-0 | 104 +/-4 | 105 +/-12 | 95 +/-13 | 78 +/-19 | 68 +/-18 | 60 +/-13 | 62 +/-13 |
| 0.137174 | 107 +/-4 | 120 +/-9 | 125 +/-24 | 112 +/-23 | 94 +/-16 | 81 +/-13 | 75 +/-10 | 71 +/-12 |
| 0.411523 | 113 +/-23 | 122 +/-22 | 118 +/-19 | 117 +/-20 | 91 +/-13 | 79 +/-14 | 74 +/-10 | 70 +/-14 |
| 1.23457 | 124 +/-15 | 139 +/-23 | 131 +/-21 | 133 +/-20 | 109 +/-17 | 99 +/-17 | 80 +/-10 | 79 +/-16 |
| 3.7037 | 141 +/-24 | 155 +/-26 | 155 +/-27 | 158 +/-25 | 135 +/-24 | 109 +/-20 | 92 +/-13 | 77 +/-13 |
| 11.1111 | 143 +/-28 | 156 +/-26 | 167 +/-26 | 172 +/-17 | 153 +/-23 | 129 +/-15 | 107 +/-13 | 83 +/-9 |
| 33.3333 | 134 +/-13 | 148 +/-19 | 150 +/-16 | 158 +/-14 | 153 +/-23 | 126 +/-22 | 112 +/-20 | 84 +/-16 |
| 100 | 133 +/-23 | 145 +/-32 | 144 +/-27 | 149 +/-25 | 150 +/-30 | 136 +/-27 | 107 +/-23 | 78 +/-15 |

% Control

HGF vs. IDE-196 in MM28 2.5k Disp

Bliss Synergy and Antagonism
HGF vs. IDE-196 in MM28 2.5k Disp

HSA Synergy and Antagonism
HGF vs. IDE-196 in MM28 2.5k Disp

Bliss Synergy and Antagonism
HGF vs. IDE-196 in MM28 2.5k Disp

HSA Synergy and Antagonism
HGF vs. IDE-196 in MM28 2.5k Disp

Loewe Synergy and Antagonism
HGF vs. IDE-196 in MM28 2.5k Disp

IDE-196 [nM]

| Crizo [nM] | 0 | 0.64 | 3.2 | 16 | 80 | 400 | 2000 | 10000 |
|---|---|---|---|---|---|---|---|---|
| 0 | 100 +/-0 | 102 +/-12 | 106 +/-10 | 97 +/-10 | 88 +/-10 | 69 +/-11 | 59 +/-9 | 46 +/-3 |
| 13.7174 | 94 +/-7 | 97 +/-13 | 92 +/-10 | 85 +/-13 | 67 +/-9 | 52 +/-11 | 45 +/-9 | 36 +/-6 |
| 41.1523 | 90 +/-13 | 85 +/6 | 89 +/-8 | 76 +/-10 | 52 +/-6 | 36 +/-8 | 31 +/-8 | 27 +/-7 |
| 123.457 | 80 +/-22 | 79 +/-11 | 77 +/-9 | 64 +/-13 | 42 +/-9 | 29 +/-4 | 24 +/-5 | 20 +/-5 |
| 370.37 | 76 +/-18 | 81 +/-12 | 73 +/-10 | 64 +/-10 | 41 +/-9 | 26 +/-5 | 22 +/-5 | 16 +/-4 |
| 1111.11 | 56 +/-8 | 57 +/-8 | 54 +/-8 | 44 +/-6 | 26 +/-4 | 16 +/-3 | 13 +/-4 | [illegible] +/-2 |
| 3333.33 | 36 +/-9 | 35 +/-7 | 34 +/-9 | 26 +/-7 | 14 +/-4 | 7 +/-3 | 4 +/-2 | 2 +/-0 |
| 10000 | 1 +/-0 | 1 +/-0 | 1 +/-1 | 1 +/-0 | 0 +/-0 | 0 +/-0 | 0 +/-0 | 1 +/-0 |

Crizo vs. IDE-196 in Mel-202 5k Disp

Bliss Synergy and Antagonism
Crizo vs. IDE-196 in Mel202
2.5k Disp

Loewe Synergy and Antagonism
Crizo vs. IDE-196 in Mel202
2.5k Disp

HSA Synergy and Antagonism
Crizo vs. IDE-196 in Mel202 2.5k Disp

IDE-196 [nM]

| Capmatinib [nM] | 0 | 0.64 | 3.2 | 16 | 80 | 400 | 2000 | 10000 |
|---|---|---|---|---|---|---|---|---|
| 0 | 100 +/-0 | 106 +/-3 | 115 +/-11 | 96 +/-8 | 76 +/-8 | 51 +/-4 | 40 +/-1 | 32 +/-3 |
| 0.137174 | 79 +/-4 | 85 +/-4 | 89 +/-11 | 69 +/-7 | 47 +/-9 | 29 +/-4 | 24 +/-2 | 18 +/-2 |
| 0.411523 | 79 +/-5 | 80 +/2 | 82 +/-10 | 66 +/-7 | 45 +/-5 | 29 +/-3 | 23 +/-2 | 17 +/-2 |
| 1.23457 | 78 +/-6 | 75 +/-6 | 79 +/-9 | 62 +/-5 | 44 +/-6 | 29 +/-2 | 23 +/-3 | 18 +/-3 |
| 3.7037 | 74 +/-6 | 73 +/-7 | 75 +/-8 | 61 +/-1 | 44 +/-3 | 28 +/-2 | 22 +/-3 | 18 +/-2 |
| 11.1111 | 73 +/-6 | 76 +/-3 | 76 +/-8 | 64 +/-8 | 43 +/-4 | 27 +/-1 | 24 +/-2 | 19 +/-2 |
| 33.3333 | 72 +/-7 | 72 +/-4 | 71 +/-10 | 64 +/-9 | 43 +/-4 | 29 +/-2 | 25 +/-3 | 19 +/-2 |
| 10000 | 73 +/-4 | 76 +/-4 | 75 +/-6 | 67 +/-11 | 47 +/-4 | 29 +/-1 | 25 +/-4 | 21 +/-2 |

% Control

Cap vs. IDE-196 in Mel-202 5k Disp

Bliss Synergy and Antagonism
Cap vs. IDE-196 in Mel202
2.5k Disp

HSA Synergy and Antagonism
Cap vs. IDE-196 in Mel202
2.5k Disp

Loewe Synergy and Antagonism
Cap vs. IDE-196 in Mel202 2.5k Disp

IDE-196 [nM]

| Crizo [nM] (N=4) | 0.64 | 3.2 | 16 | 80 | 400 | 2000 | 10000 |
|---|---|---|---|---|---|---|---|
| 13.7174 | -19 +/-20 | -19 +/-16 | -9 +/-16 | 9 +/-11 | -4 +/-10 | -2 +/-9 | 2 +/-5 |
| 41.1523 | -19 +/-18 | -23 +/-18 | -7 +/-11 | 9 +/-14 | -3 +/-9 | -3 +/-7 | 2 +/-4 |
| 123.457 | -21 +/-21 | -16 +/-21 | -17 +/-23 | -8 +/-14 | -0 +/-9 | -6 +/-10 | 0 +/-6 |
| 370.37 | -12 +/-16 | -4 +/-15 | -3 +/-14 | 17 +/-12 | 6 +/-7 | 2 +/-7 | 5 +/-3 * |
| 1111.11 | 3 +/-19 | 13 +/-15 | 12 +/-15 | 19 +/-13 | [illegible] | 10 +/-6 * | -10 +/-3 * |
| 3333.33 | -4 +/-15 | 3 +/-13 | 4 +/-13 | [illegible] | 15 +/-3 ** | 9 +/-3 * | 9 +/-2 ** |
| 10000 | 0 +/-1 | 0 +/-2 | -1 +/-2 | 0 +/-1 | 0 +/-1 * | 0 +/-0 * | 0 +/-0 ** |

Synergy

Antagonism

Bliss Synergy and Antagonism
Crizo vs. IDE-196 in 92.1 2.5k Disp

IDE-196 [nM]

| Crizo [nM] (N=4) | 0.64 | 3.2 | 16 | 80 | 400 | 2000 | 10000 |
|---|---|---|---|---|---|---|---|
| 13.7174 | -19 +/-20 | -19 +/-16 | -9 +/-16 | 9 +/-11 | -4 +/-10 | -2 +/-9 | -2 +/-5 |
| 41.1523 | -19 +/-18 | -23 +/-18 | -7 +/-11 | 9 +/-14 | -3 +/-9 | -3 +/-7 | -2 +/-4 |
| 123.457 | -21 +/-21 | -16 +/-21 | -17 +/-23 | 8 +/-8 | 0 +/-9 | -6 +/-10 | 0 +/-6 |
| 370.37 | -12 +/-16 | -4 +/-15 | -2 +/-14 | 17 +/-12 | 6 +/-7 | 2 +/-7 | 5 +/-3 * |
| 1111.11 | 3 +/-19 | 15 +/-15 | 14 +/-15 | [illegible] | 19 +/-5 * | 11 +/-6 * | 10 +/-3 * |
| 3333.33 | -4 +/-15 | -4 +/-13 | 9 +/-13 | [illegible] | [illegible] | 23 +/-3 ** | 20 +/-2 ** |
| 10000 | 0 +/-1 | 0 +/-2 | -1 +/-2 | 1 +/-1 | 2 +/-1 * | 2 +/-0 * | 2 +/-0 ** |

Synergy

Antagonism

HSA Synergy and Antagonism
Crizo vs. IDE-196 in 92.1 2.5k Disp

IDE-196 [nM]

| Crizo [nM] (N=4) | 0.64 | 3.2 | 16 | 80 | 400 | 2000 | 10000 |
|---|---|---|---|---|---|---|---|
| 13.7174 | -20 +/-20 | -19 +/-16 | -9 +/-16 | 9 +/-11 | -4 +/-10 | -2 +/-9 | 2 +/-5 |
| 41.1523 | -19 +/-18 | -24 +/-18 | -7 +/-11 | 8 +/-14 | -4 +/-9 | -3 +/-7 | 2 +/-4 |
| 123.457 | -21 +/-21 | -16 +/-26 | -18 +/-23 | 7 +/-14 | 0 +/-9 | -7 +/-10 | 0 +/-6 |
| 370.37 | -12 +/-16 | -5 +/-15 | -4 +/-14 | 15 +/-12 | 5 +/-7 | 2 +/-7 | 5 +/-3 * |
| 1111.11 | 2 +/-19 | 11 +/-15 | 8 +/-15 | 19 +/-13 | 15 +/-5 * | 9 +/-6 * | 10 +/-3 * |
| 3333.33 | -4 +/-15 | 3 +/-13 | 4 +/-13 | [illegible] | [illegible] | 18 +/-3 ** | 19 +/-2 ** |
| 10000 | 0 +/-1 | 0 +/-2 | -1 +/-2 | 1 +/-1 | 2 +/-1 * | 2 +/-0 * | 2 +/-0 ** |

Synergy

Antagonism

Loewe Synergy and Antagonism
Crizo vs. IDE-196 in 92.1 2.5k Disp

FIG. 6A (Continued)

Bliss Synergy and Antagonism
Crizo vs. IDE-196 in 92.1 2.5k Disp

HSA Synergy and Antagonism
Crizo vs. IDE-196 in 92.1 2.5k Disp

Loewe Synergy and Antagonism
Crizo vs. IDE-196 in 92.1 2.5k Disp

Bliss Model
Cap vs. IDE-196 in 92.1 2.5k Disp

Bliss Synergy and Antagonism
Cap vs. IDE-196 in 92.1 2.5k Disp

HSA Synergy and Antagonism
Cap vs. IDE-196 in 92.1 2.5k Disp

Loewe Synergy and Antagonism
Cap vs. IDE-196 in 92.1 2.5k Disp

Bliss Synergy and Antagonism
Cap vs. IDE-196 in 92.1 2.5k Disp

HSA Synergy and Antagonism
Cap vs. IDE-196 in 92.1 2.5k Disp

Loewe Synergy and Antagonism
Cap vs. IDE-196 in 92.1 2.5k Disp

IDE-196 [nM]

| Crizo [nM] | 0 | 0.64 | 3.2 | 16 | 80 | 400 | 2000 | 10000 |
|---|---|---|---|---|---|---|---|---|
| 0 | 100 +/-0 | 116 +/-9 | 110 +/-8 | 104 +/-5 | 74 +/-6 | 50 +/-4 | 41 +/-3 | 36 +/-2 |
| 13.7174 | 97 +/-2 | 113 +/-6 | 106 +/-8 | 104 +/-9 | 72 +/-4 | 50 +/-3 | 38 +/-1 | 35 +/-2 |
| 41.1523 | 96 +/-3 | 105 +/-10 | 103 +/-4 | 100 +/-11 | 66 +/-8 | 47 +/-4 | 36 +/-1 | 33 +/-2 |
| 123.457 | 93 +/-4 | 98 +/-8 | 92 +/-4 | 90 +/-12 | 61 +/-3 | 41 +/-4 | 32 +/-2 | 32 +/-2 |
| 370.37 | 88 +/-7 | 93 +/-10 | 89 +/-5 | 88 +/-15 | 54 +/-4 | 37 +/-4 | 30 +/-3 | 29 +/-2 |
| 1111.11 | 80 +/-13 | 84 +/-9 | 79 +/-4 | 77 +/-11 | 47 +/-5 | 31 +/-4 | 26 +/-3 | 27 +/-3 |
| 3333.33 | 71 +/-9 | 67 +/-5 | 69 +/-5 | 60 +/-8 | 34 +/-2 | 24 +/-2 | 21 +/-2 | 24 +/-1 |
| 10000 | 34 +/-10 | 30 +/-0 | 36 +/-10 | 27 +/-11 | 12 +/-5 | 7 +/-4 | 7 +/-4 | 3 +/-1 |

% Control

Crizo vs. IDE-196 in MM28 5k Disp

Bliss Synergy and Antagonism
Crizo vs. IDE-196 in MM28 5k Disp

HSA Synergy and Antagonism
Crizo vs. IDE-196 in MM28 5k Disp

Loewe Synergy and Antagonism
Crizo vs. IDE-196 in MM28 5k Disp

Bliss Synergy and Antagonism
Crizo vs. IDE-196 in MM28 5k Disp

HSA Synergy and Antagonism
Crizo vs. IDE-196 in MM28 5k Disp

Loewe Synergy and Antagonism
Crizo vs. IDE-196 in MM28 5k Disp

Synergy Mapped to D-R (Bliss)
Crizo vs. IDE-196 in MM28 5k Disp

Synergy Mapped to D-R (HSA)
Crizo vs. IDE-196 in MM28 5k Disp

Synergy Mapped to D-R (LOEWE)
Crizo vs. IDE-196 in MM28 5k Disp

Abs $EC_{50}$ = 182nM

Abs $EC_{95}$ = 2e-02nM

IDE-196 [nM]

| Capmatinib [nM] | 0 | 0.64 | 3.2 | 16 | 80 | 400 | 2000 | 10000 |
|---|---|---|---|---|---|---|---|---|
| 0 | 100 +/-0 | 105 +/-2 | 99 +/-4 | 96 +/-4 | 69 +/-6 | 41 +/-2 | 33 +/-3 | 38 +/-2 |
| 13.7174 | 82 +/-2 | 84 +/-3 | 78 +/-4 | 74 +/-4 | 48 +/-2 | 30 +/-7 | 24 +/-0 | 31 +/-0 |
| 41.1523 | 84 +/-2 | 85 +/-1 | 83 +/-2 | 76 +/-1 | 51 +/-3 | 31 +/-2 | 25 +/-0 | 33 +/-1 |
| 123.457 | 87 +/-4 | 84 +/-2 | 83 +/-3 | 77 +/-4 | 52 +/-2 | 32 +/-3 | 25 +/-2 | 31 +/-1 |
| 370.37 | 88 +/-5 | 86 +/-5 | 85 +/-3 | 78 +/-4 | 53 +/-3 | 32 +/-3 | 26 +/-1 | 33 +/-2 |
| 1111.11 | 87 +/-4 | 88 +/-3 | 83 +/-1 | 77 +/-3 | 50 +/-1 | 32 +/-2 | 26 +/-1 | 33 +/-1 |
| 3333.33 | 88 +/-3 | 84 +/-5 | 83 +/-3 | 76 +/-4 | 49 +/-2 | 30 +/-1 | 27 +/-1 | 34 +/-2 |
| 10000 | 83 +/-3 | 83 +/-2 | 80 +/-3 | 69 +/-3 | 45 +/-2 | 29 +/-2 | 28 +/-3 | 37 +/-2 |

% Control

Cap vs. IDE-196 in MM28 5k Disp

Bliss Synergy and Antagonism
Cap vs. IDE-196 in MM28 5k Disp

HSA Synergy and Antagonism
Cap vs. IDE-196 in MM28 5k Disp

Loewe Synergy and Antagonism
Cap vs. IDE-196 in MM28 5k Disp

PHARMACEUTICAL COMBINATION AND TUMOR TREATMENT

CLAIM OF PRIORITY

This patent application is a U.S. National Stage Filing under 35 U.S.C. 371 from International Application No. PCT/US2021/049310, filed on Sep. 7, 2021, and published as WO 2022/055893 on Mar. 17, 2022, which application claims the benefit of priority to U.S. Application Ser. No. 63/075,702, filed Sep. 8, 2020, which is incorporated by reference herein in its entirety.

BACKGROUND

Uveal melanoma is the most common primary intraocular tumor in adults. While relatively rare, the cancer can be exceedingly deadly. Radiation, resection, and enucleation are widely used as first line treatments, yet these treatments are only modestly effective. Even after enucleation, the cancer can return—and spread—in up to half of patients. Common sites of metastasis include predominantly liver, and also lung, bone, subcutaneous tissue, and lymph. For patients overall, the five-year survival rate is about 15%. For patients with metastatic disease, the median survival is about ten months. There is currently no approved pharmaceutical therapy for treatment of metastatic uveal melanoma. Metastatic uveal melanoma has remained an uncured disease. See, Croce et al., Targeted Therapy of Uveal Melanoma: Recent Failures and New Perspectives, Cancers 2019, 11 (6), 846.

Protein Kinase C is being investigated as a target for treating metastatic uveal melanoma. About 90% of uveal melanoma tumors harbor mutations in the guanine nucleotide-binding proteins GNAQ or GNA11, which can function to activate PKC-family proteins and the downstream MAPK pathways involved in tumor proliferation. Non-uveal tumors can also exhibit such mutations. In humans, the PKC family includes a number of different isoforms, each protein isoform conferring differing regulatory and intracellular localization properties. Human PKC isoforms include: "classical" calcium-dependent PKCs alpha (α), beta-1 (βI), beta-2 (βII), and gamma (γ); "novel" calcium-independent PKCs delta (δ), epsilon (ε), eta (η), and theta (θ), and "atypical" PKCs zeta (ζ) and iota (ι).

Sotrastaurin is a maleimide-type PKC inhibitor that exhibits non-selective or "pan-selective" activity across the family of PKC isoforms, as well as showing activity against some kinases outside the PKC family. See, WO 2014/174478 A1. Enzastaurin, another maleimide-type PKC inhibitor, is a PKC inhibitor targets the classical, calcium-dependent PKC isoforms, specifically PKC isoform beta-1. See, US 2010/0267742 A1. Neither compound has been approved for therapeutic use in humans.

IDE196 represents a new class of PKC inhibitor, displays high potency against novel and classical PKC isoforms, is more active for the novel, calcium-independent PKC isoforms than against classic PKC isoforms, and delivers significant therapy for primary uveal melanoma. See WO 2019/053595. However, metastatic uveal melanoma seems to resist developing therapies.

Thus, there is an unmet need for therapies that can treat uveal melanoma, particularly metastatic uveal melanoma, as well as cancers characterized by tumors having GNAQ and GNA11 mutations.

SUMMARY

These and other needs are met by the present invention which is directed to pharmaceutical products, compositions, methods, and kits useful for treating metastatic uveal melanoma, tumors harboring GNAQ or GNA11 mutations and other proliferative diseases. In various aspects, the present invention involves a combination therapy comprising a protein kinase C inhibitor and a cMET inhibitor.

For example, an aspect of the invention is directed to methods of cancer treatment. In various aspects, a patient having metastatic uveal melanoma or a tumor having a GNAQ or GNA11 mutation ("GNAQ/11 tumor") is selected, and a cMET inhibitor and a protein kinase C inhibitor are co-administered to the selected patient.

The protein kinase C inhibitor can be represented by Formula II:

(II)

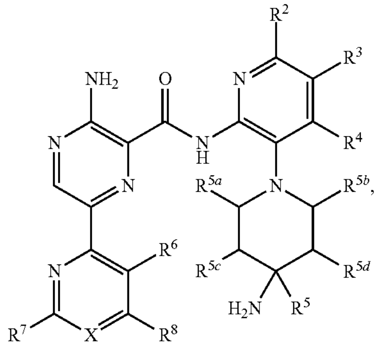

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$ alkoxy (optionally substituted by one or more halogens);

$R^{5a}$ and $R^{5b}$ are each independently selected from the group consisting of H, $^2H$ and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

In another aspect, the method can involve treating cancer in a patient having metastatic uveal melanoma exhibiting elevated cMET presence, which can be determined by assessing a biopsy of the metastatic uveal melanoma. The patient having such a form of metastatic uveal melanoma can be treated by co-administration of a cMET inhibitor and a protein kinase C inhibitor, which can be represented by Formula II as set forth above.

In yet another aspect, the method can involve treating cancer in a patient having a tumor with a GNAQ or GNA11 mutation ("GNAQ/11 tumor"), and which exhibits elevated cMET presence. The GNAQ/11 tumor can be a primary GNAQ/11 tumor or a metastatic GNAQ/11 tumor. Elevated cMET presence in the GNAQ/11 tumor can be determined by assessing a biopsy. Such a patient can be treated by co-administration of a cMET inhibitor and a protein kinase C inhibitor, which can be represented by Formula II as set forth above.

The present invention also provides pharmaceutical products and kits useful for selecting and treating a patient having a proliferative disease such as metastatic uveal melanoma or a GNAQ/11 tumor. Various products, kits, and compositions described herein incorporate a pharmaceutical combination comprising a PKC inhibitor and a cMET inhibitor.

A preferred example of the PKC inhibitor is 3-amino-N-(3-(4-amino-4-methylpiperidin-1-yl)pyridin-2-yl)-6-(3-(trifluoromethyl)pyridin-2-yl)pyrazine-2-carboxamide (Compound A). Preferred examples of the cMET inhibitor include crizotinib, capmatinib, cabozantinib, tivantinib, and any combination thereof.

DEFINITIONS

Figure 1A:
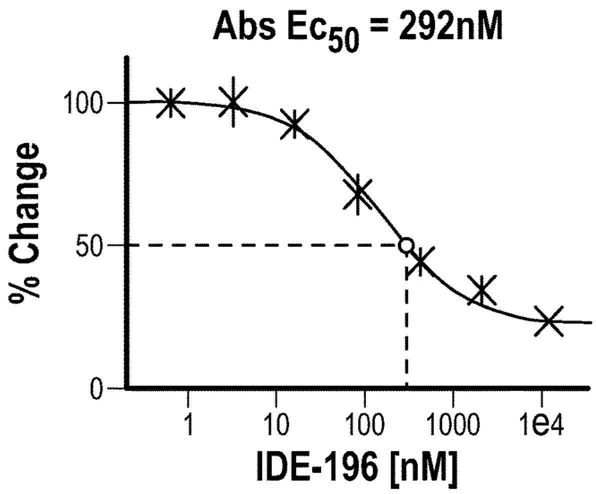
FIG. 1A provides charts illustrating the antagonistic effect of HGF on IDE 196 (Compound A defined below) in MEL-202 primary uveal melanoma cells.
Figure 1A:
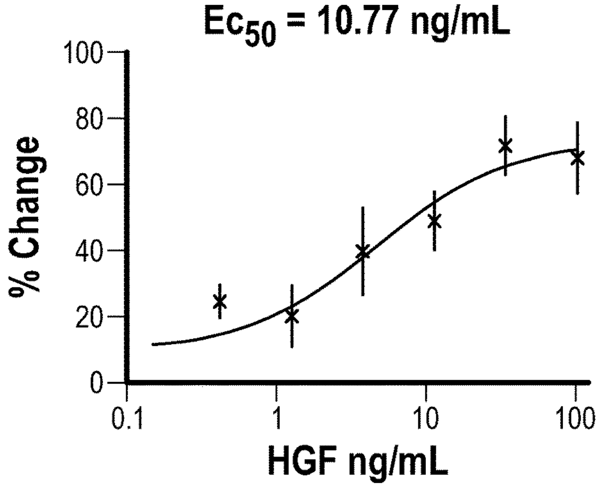
Figure 1A:
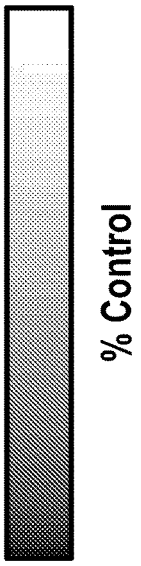
Figure 1A:
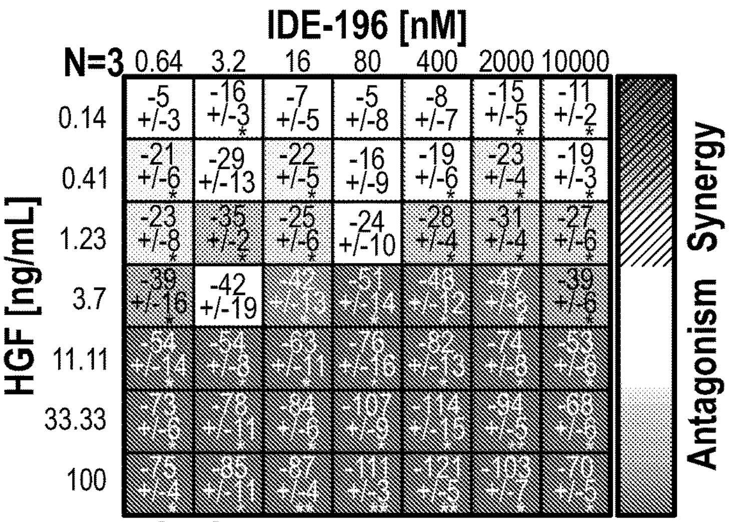
Figure 1A:
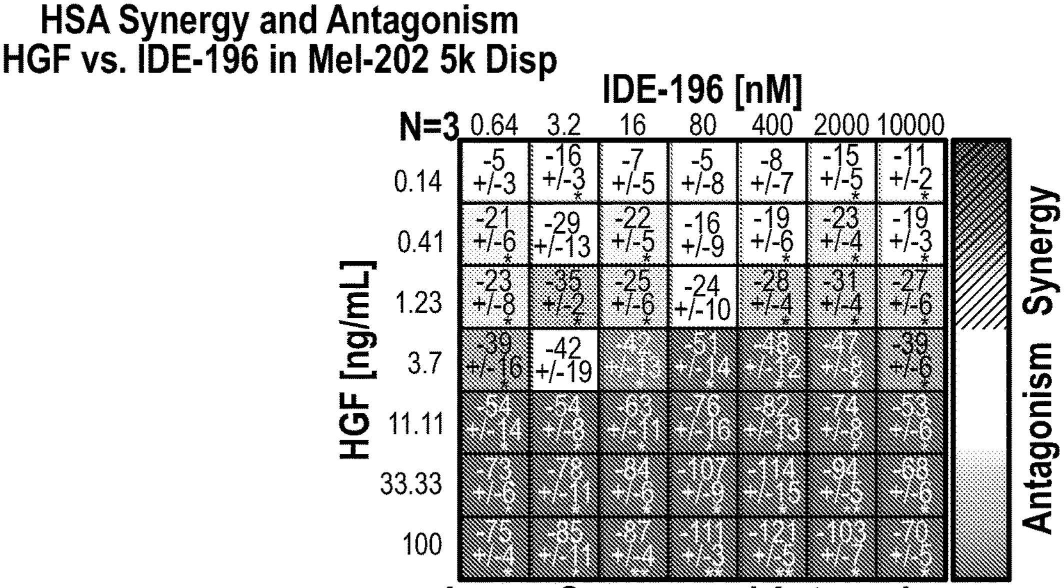
Figure 1A:
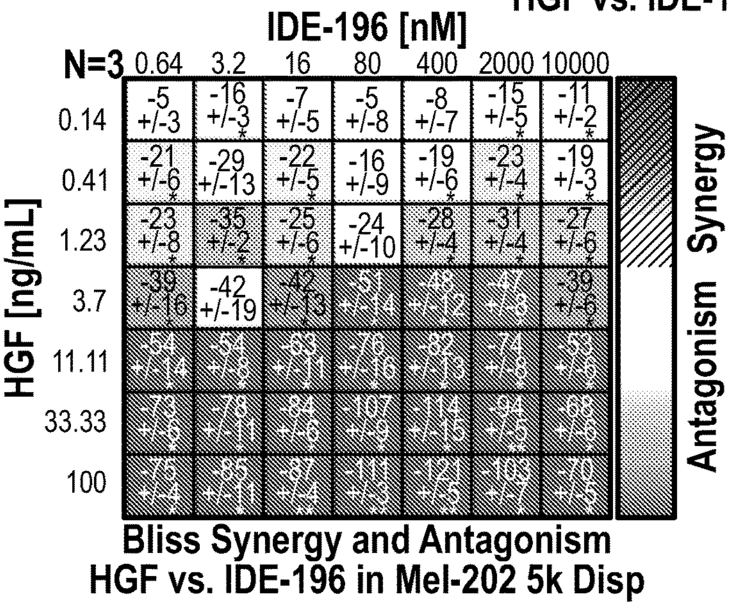
Figure 1A:
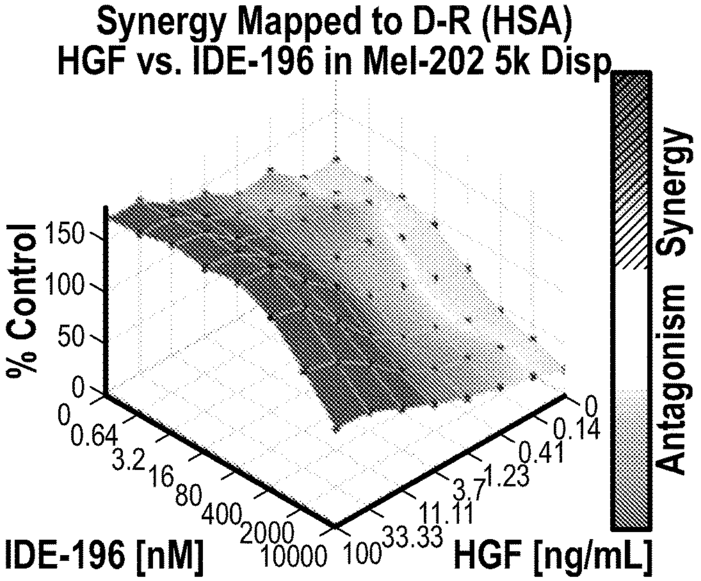
Figure 1A:
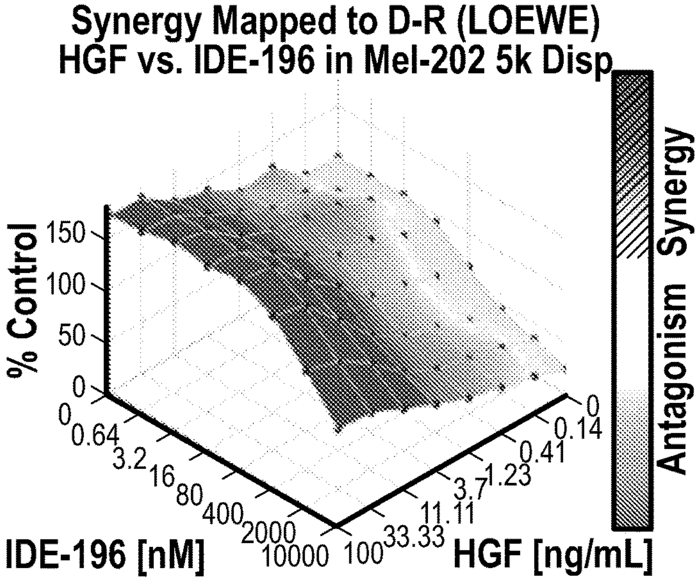
Figure 1A:
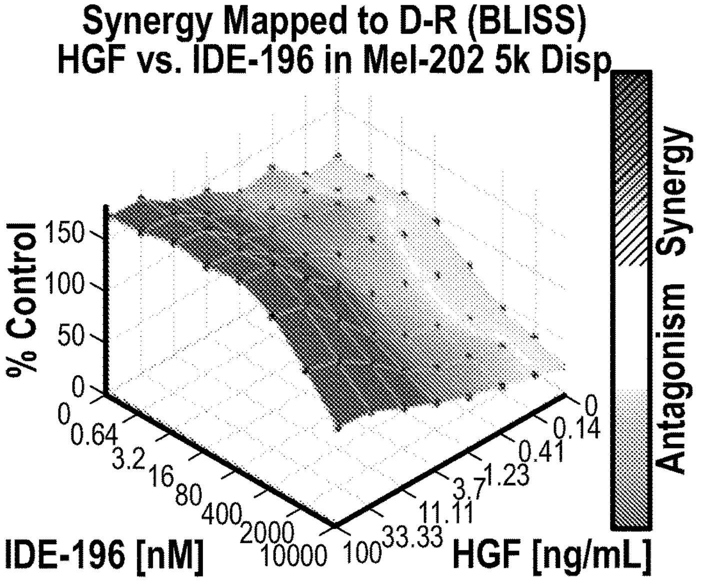
Figure 1A:
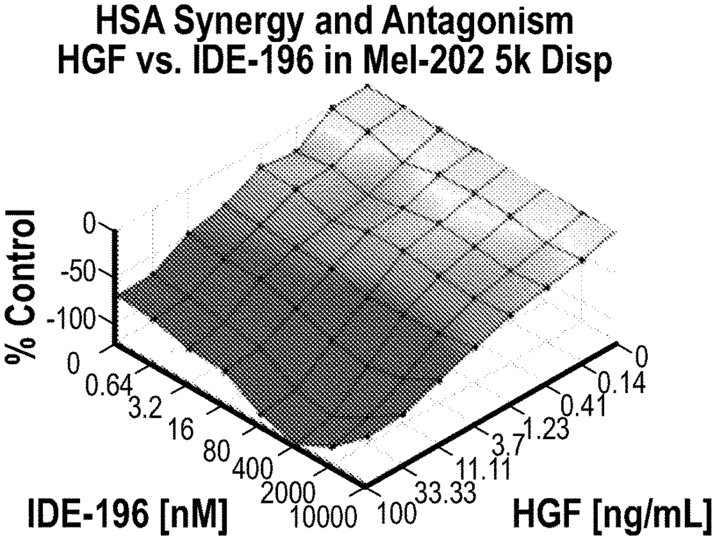
Figure 1A:
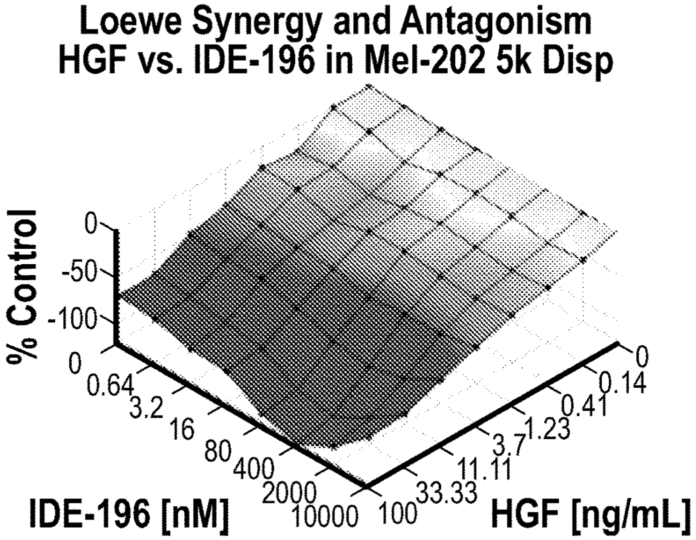
Figure 1A:
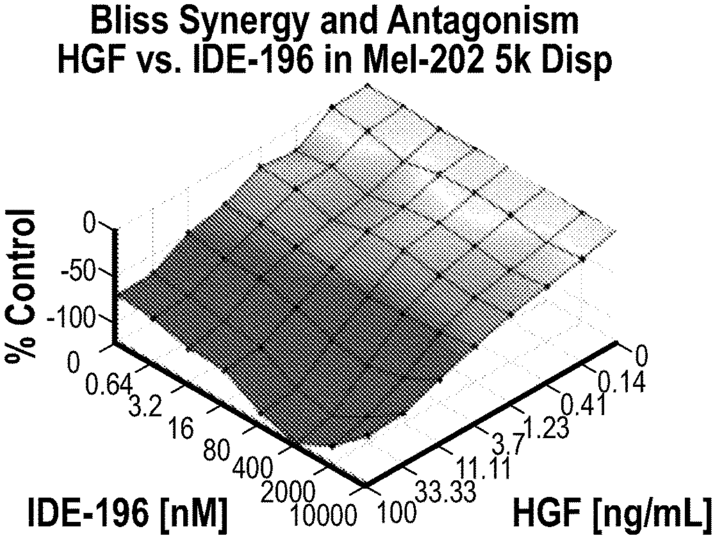

This Definitions Section is an integral part of the Detailed Description of the Invention. Unless defined otherwise, all technical and scientific terms used herein have the same meaning as commonly understood by a person of ordinary skill in the art.

The use of the articles "a", "an", and "the" in both the specification and claims are to be construed to cover both the singular and the plural, unless otherwise indicated herein or clearly contradicted by context. The terms "comprising", "having", "including" and "containing" are to be construed as open terms (for example meaning "including but not limited to") unless otherwise noted. The term "or" is used to refer to a nonexclusive "or" unless otherwise indicated herein or clearly contradicted by context. The statement "at least one of A and B" or "at least one of A or B" has the same meaning as "A or B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

The term "may" in the context of this application means "is permitted to" or "is able to" and is a synonym for the term "can." The term "may" as used herein does not mean possibility or chance.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation and can also be conducted sequentially in any order, and the resulting process will fall within the literal scope of the claimed process.

The terms "about", "approximately", or "approximate", when used in connection with a numerical value, means that a collection or range of values is included. As used herein "about X" includes a range of values that are ±25%, ±20%, ±10%, ±5%, ±2%, ±1%, ±0.5%, ±0.2%, or ±0.1% of X, where X is a numerical value. In one embodiment, the term "about" refers to a range of values which are 25% more or less than the specified value. In another embodiment, the term "about" refers to a range of values which are 20% more or less than the specified value. In yet another embodiment, the term "about" refers to a range of values which are 10% more or less than the specified value. Preferably, the term "about" refers to a range of values which are 5% more or less than the specified value. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

The phrase "alkyl" refers to alkyl groups that do not contain heteroatoms. Thus, the phrase includes straight chain alkyl groups, such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH_3)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)—CH(CH_3)(CH_2CH_3)$, $—CH_2CH_2—CH(CH_3)_2$, $—CH_2CH_2CH(CH_3)(CH_2CH_3)$, $—CH_2CH_2CH(CH_2CH_3)_2$, $—CH_2CH_2C(CH_3)_3$, $—CH_2CH_2C(CH_2CH_3)_3$, $—CH(CH_3) CH_2—CH(CH_3)_2$, $—CH(CH_3) CH(CH_3) CH(CH_3)_2$, $—CH(CH_2CH_3) CH(CH_3) CH(CH_3)(CH_2CH_3)$, and others. The phrase also includes cyclic alkyl groups such as cyclopropyl, cyclobutyl, cyclopentyl, cyclohexyl, cycloheptyl, and cyclooctyl, and such rings substituted with straight and branched chain alkyl groups as defined above. Thus, the term "$C_{1-12}$ alkyl group" includes primary alkyl groups, secondary alkyl groups, and TERTiary alkyl groups. Alkyl groups include straight and branched chain alkyl groups and cyclic alkyl groups having 1 to 12 carbon atoms with cyclic alkyl groups having at least 3 carbon atoms.

As used herein, "$C_{1-6}$ alkyl" includes both substituted or unsubstituted straight or branched chain alkyl groups having from 1 to 6 carbon atoms. Representative $C_{1-6}$ alkyl groups include, for example, $C_{1-3}$ alkyl, $C_{2-3}$ alkyl, methyl, ethyl, propyl, isopropyl, n-butyl, TERT-butyl, neopentyl, trifluoromethyl, pentafluoroethyl and the like. Unless stated otherwise, $C_{1-6}$ alkyl groups may be substituted, such as with halo, hydroxy, amino, nitro and/or cyano groups, and the like. Representative $C_{1-3}$ haloalkyl and $C_{1-3}$ hydroxyalkyl include chloromethyl, trichloromethyl, trifluoromethyl, fluoromethyl, fluoroethyl, chloroethyl, hydroxymethyl, hydroxyethyl, and the like. Other suitable substituted $C_{1-3}$ alkyl moieties include, for example, arylalkyl, aminoalkyl, aminoaralkyl, carbonylaminoalkyl, alkylcarbonylaminoalkyl, arylcarbonylaminoalkyl, arylalkylcarbonylaminoalkyl, aminoalkoxyalkyl and arylaminoalkyl, unless stated otherwise.

As used herein, "$C_{1-6}$ alkoxy" as used herein refers to the radical RO—, wherein R is $C_{1-6}$ alkyl. Representative examples of $C_{1-6}$ alkoxy groups include $C_{1-3}$ alkoxy, methoxy, ethoxy, t-butoxy, trifluoromethoxy and the like.

As used herein, the term "halogen" or "halo" refers to chloro, bromo, fluoro and iodo groups. "Haloalkyl" refers to a $C_{1-3}$ alkyl radical substituted with one or more halogen atoms. The term "haloalkoxy" refers to a $C_{1-3}$ alkoxy radical substituted with one or more halogen atoms.

"Hydroxy" or "Hydroxyl" refers to the group-OH.

"Amino" refers herein to the group $—NH_2$.

The term "aryl" refers herein to a 6-10 member fully unsaturated, conjugated carbocyclic ring system such as but not limited to phenyl or naphthyl. The aryl ring or rings may be unsubstituted or substituted by one or more halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl, a heteroaryl group and/or a 4-7 membered heterocyclyl ring having 1 to 3 heteroatoms selected from N, O and S, said heterocyclyl ring optionally substituted one or two substituents each independently selected from the group consisting of: H, $^2H$, halo, CN, $C_{1-3}$ alkyl, $C_{1-3}$ alkoxy, $C_{1-3}$ haloalkyl, and $C_{1-3}$ haloalkoxyalkyl groups.

The terms "carbocycloalkyl and carbobicyclic and carbobicyclyl" refer to $C_{3-16}$ cycloalkyl and bicycloalkyl groups in which all ring atoms are carbon. When used in connection with cycloalkyl substituents, the term "polycyclic" refers herein to fused and non-fused cyclic alkyl structures. The term "carbobicyclic or carbobicyclyl" refers to a saturated, or partially unsaturated carbocyclic ring fused to another carbocyclic ring, aryl ring, heterocyclic ring or heteroaryl ring. The cycloalkyl group is unsubstituted or substituted.

The term "$C_{1-3}$ alkylamino" refers herein to the group-NRR' where R and R' are each independently selected from hydrogen or a $C_{1-3}$ alkyl provided at least one of R and R' is $C_{1-3}$ alkyl.

The term "arylamino" refers herein to the group-NRR' where R is $C_{6-10}$ aryl, including phenyl, and R' is hydrogen, a $C_{1-3}$ alkyl, or $C_{6-10}$ aryl, including phenyl.

The terms "heterocycloalkyl, heterocyclyl, heterocycle and heterocyclic" are synonymous and refer herein to carbon and heteroatom rings which may be partially unsaturated or may be fully saturated and may have from 1 to 5, and more typically from 1 to 4 heteroatoms in the ring structure. Suitable heteroatoms employed in such rings are nitrogen, oxygen, and sulfur. Representative heterocycloalkyl/heterocyclyl moieties include, for example, morpholino, piperazinyl, piperidinyl, 1,2-oxazinane, 2-oxopiperazinyl, 2-oxopiperidinyl, N-methyl piperazinyl, and morpholinyl, each optionally substituted. and the like.

The term "heterobicyclic" refers to a bicyclic group in which heterocyclic ring is fused to a benzene ring or another 5- or 6-membered heterocyclic ring.

Heterocyclic moieties can be unsubstituted or monosubstituted or disubstituted with various substituents independently selected from hydroxy, halo, oxo (CO), alkylimino (RN═, wherein R is a $C_{1-3}$ alkyl or $C_{1-3}$ alkoxy group), amino, $C_{1-3}$ alkylamino, $C_{1-3}$ dialkylamino, acylaminoalkyl, $C_{1-3}$ alkoxy, $C_{1-3}$ alkyl, cycloalkyl or $C_{1-3}$ haloalkyl. Heterocyclic groups (heterocyclyl) may be attached at various positions as will be apparent to those having skill in the organic and medicinal chemistry arts in conjunction with the herein.

The term "heteroaryl" refers to 5-10 membered unsaturated, conjugated heterocyclic ring system, including fused ring systems, having 1 to 4 heteroatoms each independently selected from the group consisting of: O, N and S. The heteroaryl group may be optionally substituted with one or two substituents. A subset of the "heteroaryl" system is an aromatic $C_{6-10}$ heteroaryl group having from 1 to 4 heteroatoms as ring atoms in an aromatic ring with the remainder of the ring atoms being carbon atoms. Exemplary substituents include, but are not limited to: halo, CN, $C_{1-3}$ alkyl, $C_{1-3}$ alkoxy, $C_{1-3}$ haloalkyl, $C_{1-3}$ haloalkoxy, $C_{3-7}$ cycloalkyl, and 4-7 membered heterocyclyl having 1 or 2 heteroatoms selected from N, O and S, said heterocyclyl optionally substituted with 1 to 3 substituents each independently selected from the group consisting of: halo, CN, $C_{1-3}$ alkyl, $C_{1-3}$ alkoxy, $C_{1-3}$ haloalkyl, and $C_{1-3}$ haloalkoxy. Representative heteroaryl groups include, for example, those shown below. Representative heteroaryls include, for example, imidazolyl, pyridinyl (also referred to aspyridyl), pyrazinyl, azetidinyl, thiazolyl, triazolyl, benzimidazolyl, benzothiazolyl, thiazolyl, thiazolidinyl, isothiazolyl, isothiazolidinyl, indolyl, quinolinyl, isoquinolinyl, azetidinyl, N-methylazetidinyl, pyrimidinyl, pyridazinyl, oxazolyl, oxazolidinyl, isoxazolyl, isoazolidinyl, benzimidazolyl, benzothiazolyl, benzoxazolyl, furyl, thienyl, triazolyl, benzothienyl diazapinyl, pyrryl, pyrrolinyl, pyrrolidinyl, pyrazolyl, pyrazolinyl, pyrazolidinyl, imidazoyl, imidazolinyl, imidazolidinyl and benzoxazolyl. The heteroaryl is unsubstituted or substituted with 1 to 3 substituents each independently selected from the group consisting of: H, $^{2}H$, halo, $C_{2-3}$ alkynyl, $C_{2-3}$ alkenyl, CN, $C_{1-3}$ alkyl, $C_{1-3}$ alkoxy, $C_{1-3}$ haloalkyl, $C_{1-3}$ haloalkoxy, $C_{3-7}$ cycloalkyl, $CONH_2$, $CONHC_{1-3}$ alkyl, $CONHC_{6-10}$ aryl, $SO_2NH_2$, $SO_2NHC_{1-3}$ alkyl, $SO_2NHC_{6-10}$ aryl and 4-7 membered heterocyclyl having 1 to 3 heteroatoms selected from N, O and S, said heterocyclyl optionally substituted one or two substituents each independently selected from the group consisting of: H, $^{2}H$, halo, CN, $C_{1-3}$ alkyl, $C_{1-3}$ alkoxy, $C_{1-3}$ haloalkyl, and $C_{1-3}$ haloalkoxy.

The term "$^{2}H$" refers to a heavy isotope of hydrogen that is also referred to as deuterium (D).

It is understood that the above definitions of organic groups are not intended to include impermissible substitution patterns (e.g., methyl substituted with five fluoro groups or a halogen atom substituted with another halogen atom).

The term "ligand" refers to a substance that is capable for forming a covalent, complex, electrostatic, hydrophobic, hydrophilic, lipophilic, polar, steric, and/or similar molecular interaction with another substance. A ligand may be a small molecule, a charged organic or inorganic moiety, a peptide, an oligopeptide, a DNA or RNA fragment, an immunoprotein, an antibody fragment, a polyclonal antibody, a monoclonal antibody, a humanized monoclonal antibody, and/or similar chemical entities. The ligand may, but not necessarily, carry a signaling group such as a radioactive, fluorescent or phosphorescent group so that when forming a molecular interaction with another substance, the combination may be detected. The ligand preferably may be a peptide, an antibody of any kind or an antibody fragment of any kind. A subset of ligand may include two ligands, the first of which interacts with another substance and the second of which carries a signaling group and interacts with the first ligand.

As used herein, the term "PKC" refers to protein kinase C. The PKC family of serine/threonine kinases is composed of at least ten isoforms, pivotal in various cellular differentiation processes with distinctive means of regulation. Depending on context, the term PKC can refer to the entire family of isoforms or a particular isoform. The PKC family includes conventional (classic) isoforms alpha, beta-1, beta-2, and gamma; novel isoforms delta, epsilon, eta, and theta; and atypical isoforms zeta and iota. As used herein, the term "protein kinase C inhibitor" or "PKC inhibitor" refers to a protein kinase C inhibitor that may be pan (multi-subtype) or selective to one or more PKC isozymes.

The term "inhibitor" refers to modulatory molecules or compounds that, e.g., partially or totally block activity, decrease, prevent, delay activation, inactivate, desensitize, or down regulate biological activity or expression of a protein, a kinase, or other biological structure, e.g., PKC or cMET. For example, inhibitors can reversibly, or irreversibly, bind to an enzyme in a competitively, uncompetitively, non-competitively, or a combination thereof.

The term "pharmaceutical composition" refers to an active agent formulated with one or more pharmaceutically acceptable carriers. Examples of pharmaceutical compositions include a parenteral solution, a tablet is employed herein to refer to those compounds, materials, compositions, and/or dosage forms which are, within the scope of sound medical judgment, suitable for use in contact with the tissues of human beings without excessive toxicity, irritation, allergic response, or other problem or complication commensurate with a reasonable benefit/risk ratio.

The phrase "pharmaceutically acceptable" is employed herein to refer to those compounds, materials, compositions, excipients and/or dosage forms which are, within the scope of sound medical judgment, suitable for use in contact with the tissues of human beings without excessive toxicity, irritation, allergic response, or other problem or complication commensurate with a reasonable benefit/risk ratio.

The terms "treat," "treating" or "treatment," as used herein, refers to methods of alleviating, abating or ameliorating a disease, e.g., a tumor, or condition, or symptoms, preventing appearance of additional symptoms, ameliorating the underlying causes of symptoms, inhibiting the disease or condition, arresting or reducing the development or progression of the disease or condition, relieving the disease or condition, causing regression of the disease or condition, relieving a condition caused by the disease or condition, or stopping the symptoms of the disease or condition. In various aspects, the presently described therapy can be used prophylactically for preventing a disease, e.g., metastatic disease, or condition, or symptoms.

The term "patient" refers to a human, especially but not necessarily a human who is under the care of a physician. For example, the patient can be a human suffering or diagnosed with cancer. As another example, the patient can be an individual diagnosed with a high risk of developing cancer, tumor, or metastatic disease. For example, the patient can have been previously diagnosed and treated for uveal melanoma and is now diagnosed with a high risk of recurrence or progression to metastatic disease.

The term "patient population" refers to a plurality of patients having one or more shared disease characteristic. For example, the patient population can correspond to patients suffering from a tumor of the same tissue type. As another example, a patient population can be a plurality of patients with a tumor of the same tissue type, which has a mutation in GNAQ or GNA11. The patient population can be patients having uveal melanoma. The patient population can be patients having metastatic uveal melanoma. A patient population can be 2 or more patients, for example, 2, 3, 4, 5, 6, 7, 8, 9, 10, 15, 20, 50, 100, 500, 1000, 2000, 5000, 7000, or more patients. In various aspects, patient population can be defined to provide a representative population suitable for evaluating the relative severity of a patient's disease. In some cases, patient populations can further be defined to include characteristics beyond disease characteristics, for example, demographic, phenotypic, or genotypic characteristics, with the goal of providing an even more accurate assessment and evaluation of patients. In some aspects, the patient population can alternatively refer to a "healthy population" or general population having patients that are both healthy and suffering from a disease.

The terms "administration" or "administer" refers to contacting a patient with the specified compound or composition to treating or preventing a disease or symptom thereof. In various examples, administering includes contacting the patient's tumor, or contacting the diseased tissue in which the tumor is located, with the specified compound or composition.

"Disease," as used herein, is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human to have a reduced duration and/or quality of life. A "proliferative disease" is a disease characterized by a malignant proliferation of cells. As an example, the disease can be a cancer in which protein kinase C mediates or otherwise plays a role in the pathogenesis of the cancer. As another example, the disease can be a tumor, such as a solid tumor, a metastatic tumor, or both. Examples of proliferative disease, generally, include pancreatic cancer, stomach cancer, colorectal cancer, cervical cancer, lung cancer, bladder cancer, liver cancer, breast cancer, head and neck cancer, eye cancer, and brain cancer, or a tumors thereof.

A patient "in need of treatment," as used herein, refers to a judgment made by a physician or other caregiver that a patient requires or will benefit from treatment. A patient "diagnosed with" a specified disease refers to a judgment made by a physician or other caregiver that a patient is afflicted with a disease. A patient "suffering from" a specified disease refers a patient afflicted with that disease, which can be evidenced based on disease progression or a judgment made by a physician or other caregiver that a patient is afflicted with a disease. Such judgments can be made based on a variety of factors within the realm of a physician's or caregiver's expertise. In various aspects, the presently described treatment is provided to a patient in need of treatment for, diagnosed with, or suffering from, a disease described herein.

As used herein, the term 'tumor' includes solid tumors, liquid tumors, or a combination thereof. For example, the tumor can be primary uveal melanoma, metastatic uveal melanoma, a tumor having one or more mutation in GNAQ or GNA11, a tumor other than uveal melanoma, or a metastatic tumor in the liver. As a further example, the tumor can be metastatic uveal melanoma in the liver, or a primary uveal melanoma having one or more mutation in GNAQ or GNA11. In various aspects, the tumor is a malignant (cancerous) solid tumor. In various aspects, the tumor is a liquid tumor.

As used herein, "mutation" can refer to one or more changes in a polynucleotide sequence. Mutations can arise in tumor cells or they can arise in cells prior to appearance or diagnosis of the tumor. Mutations can be acquired, or they can be germline (inherited) mutations. Mutations can represent a deviation from healthy functioning of the polynucleotide sequence and derived proteins. Mutations can be nucleotide substitutions, such as single nucleotide substitutions, insertions, or deletions. As an example, GNAQ and GNA11 mutations are typically activating mutations that lead to constitutive activation of the a subunit. Without being bound to a theory, it is believed that the constitutive activity results from a lack of the GTP-hydrolase activity in the mutant GNAQ or GNA11 protein. Activating mutations can also refer to mutations that result in a loss or decrease of GTP hydrolyzing activity of a Gα subunit. Mutations in GNAQ and GNA11 include a substitution of arginine in codon R183 or substitution of glutamine in codon Q209, or may be other mutations. In some aspects, mutations in GNAQ) and/or GNA11 can be selected from group comprising of: Q209P, Q209L, Q209H, Q209K, Q209Y, Q209R, Q209H, R183Q, R183, for example, GNAQ Q209 may be mutated to either P or L as well as to R or H; GNAQ R183 may be mutated to Q; GNA11 Q209 may be mutated to L as well as to P or K; GNAQ R183 may mutate to C or H. Genetic mutations can include any of the following: insertion mutations, substitution mutations, deletion mutations, gain of function mutations, loss of function mutations, and non-synonymous mutations. A gain of function mutation results in an altered gene product that possesses a new molecular function or a new pattern of gene expression. In contrast, a loss of function mutation produces an altered gene product that lacks the molecular function of the equivalent wild-type gene.

As used herein, the term "GINAQ" refers to Guanine Nucleotide-Binding Protein Alpha-Q gene that encodes the Gq alpha subunit (Gαq) and the term "GNA11" refers to Guanine Nucleotide-Binding Protein Alpha 11 genes that encodes the G11alpha subunit (Gα11) subunit. The term "GNAQ/11" refers to GNAQ and/or GNA11. The term encompasses nucleic acid and polymorphic variants, alleles, mutants, and fragments of GNAQ and GNA11. GNAQ and GNA11 sequences are well known in the art. Examples of human GNAQ sequences are available under the reference sequences NM_002072 in the NCBI nucleotide database (nucleotide sequence) and accession number NP_002063.2 (polypeptide sequence). Human GNAQ) has been localized to chromosome 9q21. Examples of human GNA11 sequences are available under the reference sequences NM_002067 in the NCBI nucleotide database (nucleotide sequence) and accession number NP_002058.2 (polypeptide sequence). Human GNA11 is localized to chromosome region 19p13.3.

As used herein, the term "mutational load" refers to the level, e.g., number, of an alteration (e.g., one or more alterations, e.g., one or more somatic alterations) per a preselected unit (e.g., per megabase) in a predetermined set of genes or all analyzed genes (e.g., in the coding regions of the predetermined set of genes). Mutation load can be measured, e.g., on a whole genome or exome basis, or on the basis of a subset of genome or exome. In certain aspects, the mutation load measured on the basis of a subset of genome or exome can be extrapolated to determine a whole genome or exome mutation load. The terms "mutation load," "mutational load," "mutation burden," and "mutational burden" are used interchangeably herein. In the context of a tumor, a mutational load is also referred to herein as "tumor mutational burden," "tumor mutation burden," or "TMB.

BAP1 refers to BRCA1-associated protein-1 gene (ubiquitin carboxy-terminal hydrolase; BAP1). The nucleic acid and amino acid sequences of BAP1 are known and publicly available (Genbank NM_004656.2, Genbank NP_004647.1). BAP1 has been functionally implicated in the DNA damage response as well as in the regulation of apoptosis, senescence and the cell cycle. Deletions and inactivating mutations in BAP1 have been previously associated with tumors of the breast and lung and, consistent with BAP1's role as tumor suppressor, restoration of BAP1 function has been shown to suppress cell growth and tumorigenicity in a BAP1-mutant lung cancer cell line.

SF3B1 refers to a gene that encodes Splicing Factor 3b Subunit 1. The nucleic acid and amino acid sequences of SF3B1 are known and publicly available (NM_012433.3, Genbank NP_036565.2). Subunit 1 of the splicing factor 3b protein complex plays a number of critical roles in the splicing mechanism of the cell. Mutations in SF3B1 affect the ability of a cell to convert pre-mRNA, which contains intronic sequence, into mature mRNA.

E1F1AX refers to a gene that encodes for the protein X-linked eukaryotic translation initiation factor 1A, which plays a role in protein synthesis. The nucleic acid and amino acid sequences of E1F1AX are known and publicly available (NM_001412.4, Genbank NP_001403.1). E1F1AX is commonly mutated in uveal melanoma.

TERT refers to either the gene encoding the enzyme Telomerase Reverse Transcriptase (TERT) or to the enzyme (i.e., protein) itself. TERT refers to the nucleoprotein, or enzyme, portion of telomerase. TERT genes have also been called "Ever Shorter Telomeres" or "EST" genes. Mutations in the promoter region of TERT have been associated with cancers including, but not limited to, thyroid cancer, bladder cancer and glioblastoma. The nucleic acid and amino acid sequences of TERT are known and publicly available (NM_198253.2, Genbank NP_937983.2).

NRAS or "neuroblastoma RAS viral oncogene homolog" refer to a small GTPase Ras family protein encoded on chromosome 1. The nucleic acid and amino acid sequences of NRAS are known and publicly available (NM_002524, Genbank NP_002515).

BRAF or "v-Raf murine sarcoma viral oncogene homolog B" refer to a Raf kinase family serine/threonine-specific protein kinase that interacts with AKT1; CRaf, HRAS, and YWHAB. The sequences of BRAF are well known in the art for a number of species, e.g., human BRAF (NM_004333, Genbank NP_004324). the NRAS and/or BRAF sequence variation(s) can be point mutations. In some aspects, a NRAS point mutation can be a point mutation resulting in one of the following amino acid residue changes: G12D; G12S; G13A; G13C; G13D; G12R; G13V; Q61H1; Q61K; Q61L; Q61R1; and Q61R2. In some aspects, a BRAF point mutation can be a point mutation resulting in one of the following amino acid residue changes: V600D TG/AT; V600E T/A; V600E TG/AA; and V600K GT/AA.

DETAILED DESCRIPTION

Embodiments of the invention provide, among other things, a combination therapy useful for treating metastatic uveal melanoma, tumors harboring GNAQ or GNA11 mutations, and other proliferative diseases (hereinafter target tumors). The GNAQ/11 tumor can be a primary GNAQ/11 tumor or a metastatic GNAQ/11 tumor. Examples of other proliferative diseases include diseases mediated by tissue abnormalities in tissue having one or more mutation in GNAQ or GNA11, which activate the PKC signaling pathway in such tissue. The combination therapy can be provided by a pharmaceutical product, a method of treatment, or a kit, and involves use of a protein kinase C inhibitor and a cMET inhibitor. Embodiments of the invention also provide methods and kits useful for selecting patients or directing a course of treatment. For example, embodiments of the present invention provide a way to identify whether to administer to a patient a combination of a protein kinase C inhibitor and a cMET inhibitor.

The present invention is based at least in part on the discovery that the antiproliferative activity of the present embodiments of PKC inhibitors, acting on PKC isoforms present in target tumors, is modulated by elevated presence of cMET. Functioning and downstream signaling of the various PKC isoforms is complex and can vary based on cellular environment. The present embodiments of PKC inhibitors are highly potent against both novel PKC isoforms delta (δ), epsilon (¿), eta (η), and theta (θ), and classical PKC isoforms alpha (α), beta-1 (βI), beta-2 (βII), and gamma (γ). Within these classes of PKC isoforms, the PKC inhibitors display greater activity against the novel PKC isoforms than displayed against the classical PKC isoforms. The present embodiments of PKC inhibitors are selective for PKC isoforms relative to off target kinases and other off target phosphotransferases and exhibit better therapeutic index and PKC activity compared with other known pan-PKC inhibitors and/or PKC inhibitors acting on the classical PKC isoforms.

It has been discovered that the anti-proliferative activity of the present embodiments of the PKC inhibitors is antagonized in target tumors exhibiting elevated presence of cMET. Moreover, cMET elevation in target tumors can vary, for example, when they are contacted with equivalent amounts of exogenous hepatocyte growth factor (HGF), the endogenous ligand for the extracellular cMET receptor. In particular, the anti-proliferative effect of IDE 196 upon each of uveal melanoma cell lines, 92.1, MM28 and MEL-202, is antagonized to a different degree even though each of the cell lines is experimentally stimulated by the same concentration of HGF. This antagonistic effect of cMET is most strongly observed in the MEL-202 and MM28 cell lines and is weaker in the 92.1 cell line. This correlates with the level of expression of cMET in these cell lines which is elevated in each of the MEL-202 or MM28 cell lines relative to the 92.1 cell line.

Figure 8A:
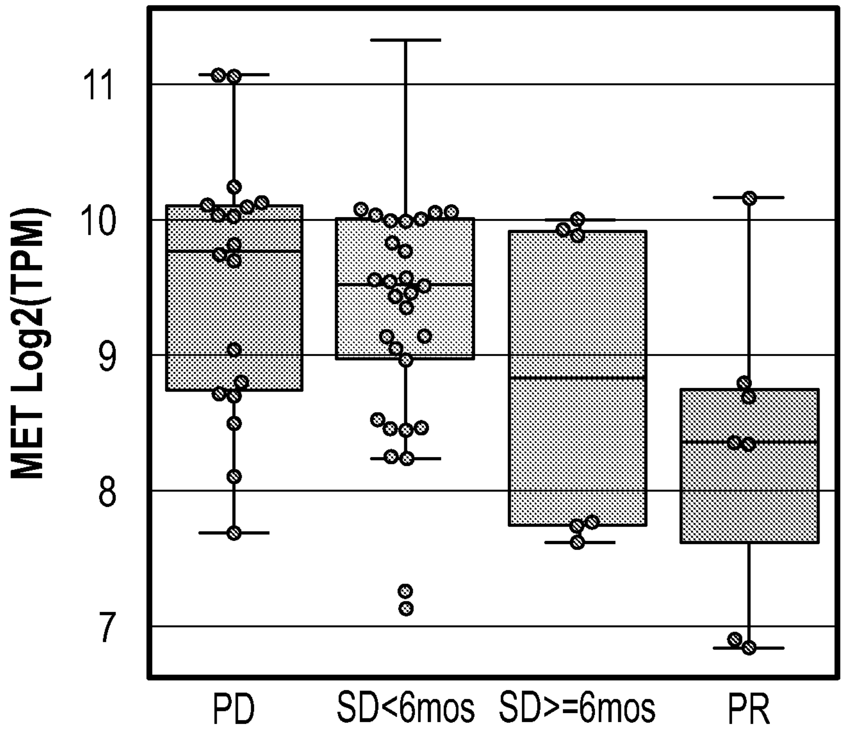
FIGS. 8A and 8B provides bar graphs illustrating cMET expression/MET activation (MET signature) across metastatic uveal melanoma patients enrolled in an IDE196 (Compound A) monotherapy trial (NCT02601378) grouped by response type. The patient groups include those having a clinical outcome determined to be progressive disease (metastatic uveal melanoma), those determined to have stable metastatic uveal melanoma for less than six months, those determined to have stable metastatic uveal melanoma for more than six months and those determined to have a partial response to treatment (i.e., ≥30% reduction in metastatic uveal melanoma tumor size by RESIST criteria).

Furthermore, data from archival metastatic uveal melanoma tissue from a human clinical trial evaluating IDE196 as monotherapy show that cMET expression and MET activation, as indicated by MET signature, can also vary in human tumors, and that elevated cMET expression and MET activation correlate generally to a poorer clinical response. These data are consistent with the observations from the in vitro cellular experiments that the elevated presence of cMET antagonizes antiproliferative activity of IDE196. With reference to Example 5 and FIGS. 8A and 8B, in this study, certain patients exhibited little or no amelioration of the proliferative target tumor when administered IDE 196 as monotherapy while other patients showed at least a partial response. In all patients, the metastatic uveal melanoma situs of the tumor was in the liver. Patients with little or no ameliorative response to IDE 196 exhibited higher tumor cMET expression or MET activation, whereas patients more responsive to IDE196 exhibited lower levels of tumor cMET expression or MET activation. These in vitro cellular data and in vivo human clinical data demonstrate that the level of cMET expression or MET activation, rather than the presence of HGF, determines the antagonism of the anti-proliferative effect of IDE 196 upon target tumors.

From these discoveries, it has been found that the combination of the present embodiments of the PKC inhibitor and a cMET inhibitor provides an advantageous treatment of patients having metastatic uveal melanoma and of patients having tumors harboring GNAQ or GNA11 mutations, including mutations activating the PKC signaling pathway. It is known to control cMET expression or cMET activation through use of cMET inhibitors. Significantly, however, cMET inhibitors, alone, do not affect uveal melanoma cell viability in any of the cell lines tested. Notably, the magnitude of synergy for the cMET inhibitor/PKC inhibitor combination correlates with the level of cMET expression of the target tumor cells. The greatest synergy is observed in the MEL-202 and MM28 cell lines treated with the combination of crizotinib or capmatinib (each, a cMET inhibitor) and IDE 196, while the combination of crizotinib or capmatinib and IDE196 shows a relative lack of synergistic effect when administered to the 92.1 cell line.

Use of such combination can further involve a method for patient selection and a criteria for determining whether to administer the PKC inhibitor as a combination therapy with a cMET inhibitor, or whether to administer the PKC inhibitor without a cMET inhibitor, such as a monotherapy or in combination with other therapeutic agents. Accordingly, in various aspects, the present invention solves the problems associated with treating difficult-to-treat proliferative diseases, such as metastatic uveal melanoma and/or tumors having a GNAQ or GNA11 mutation.

Generally, each additional therapeutic agent administered to a patient introduces risk of adverse effects and can reduce therapeutic index of the prescribed treatment. However, it is preferable for a therapy to improve therapeutic benefit while reducing risk. In various aspects, the present invention solves the problem of identifying which patients are likely to benefit from the combination, and which are not, thus offering a further advantage of providing treatment having an improved therapeutic index.

Reference will now be made in detail to certain aspects of the disclosed subject matter. While the disclosed subject matter will be described in conjunction with the enumerated claims, it will be understood that the exemplified subject matter is not intended to limit the claims to the disclosed subject matter.

Combination Therapy

The present invention provides, among other things, a combination therapy involving a protein kinase C inhibitor and a cMET inhibitor, which is useful for treating metastatic uveal melanoma, tumors having a GNAQ or GNA11 mutation ("GNAQ/11 tumor"), preferably a GNAQ or GNA11 mutation activating the PKC signaling pathway, and other proliferative diseases, such as diseases mediated by tissue abnormalities in tissue having one or more mutation in GNAQ or GNA11 which activate the PKC signaling pathway in such tissue. The GNAQ/11 tumor can be a primary GNAQ/11 tumor or a metastatic GNAQ/11 tumor. The combination therapy can be provided by a pharmaceutical product, a pharmaceutical composition, a method of treatment, or a kit, each of which can involve a protein kinase C inhibitor and a cMET inhibitor. For example, the combination therapy can involve treating a patient having metastatic uveal melanoma or having a GNAQ/11 tumor by simultaneously, or sequentially co-administering to the patient a cMET inhibitor and a protein kinase C inhibitor.

In various aspects, the protein kinase C inhibitor can have a structure represented by Formula II:

Formula II

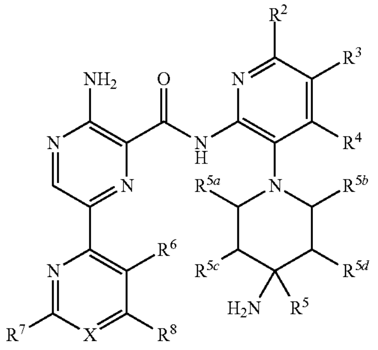

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$alkyl; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$alkyl; wherein $C_{1-3}$alkyl may optionally be substituted by one, two, three or more substituents, each independently selected from the group consisting of fluorine, hydroxyl and $C_{1-3}$alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$cycloalkyl and a 4-7 membered heterocyclyl having one, two or three heteroatoms each independently selected from the group consisting of N, O and S; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

In various aspects, the compound of Formula II can have one or more, or each, of the following: X is N; $R^2$, $R^3$ and $R^4$ are each independently H or halo; $R^5$ is H or $CH_3$; or $R^6$ and $R^7$ are each independently selected from H, halo, $C_{1-3}$ haloalkyl, $C_{1-3}$ haloalkoxy, $C_{3-7}$ cycloalkyl, morpholino, piperidinyl and piperazinyl. For example, each of $R^2$, $R^3$ and $R^4$ can be H. As another example, $R^6$ and $R^7$ is $C_{1-3}$ haloalkyl, $C_{1-3}$ haloalkoxy, $C_{3-7}$ cycloalkyl, morpholino, piperidinyl and piperazinyl, and one of $R^6$ and $R^7$ is H. In further various aspects, one of $R^6$ and $R^7$ is trifluoromethyl or trifluoromethoxy and one of $R^6$ and R is H. In yet further aspects, $R^{5a}$, $R^{5b}$, $R^{5c}$ and $R^{5d}$ are each H.

For example, the protein kinase C inhibitor can have the structure:

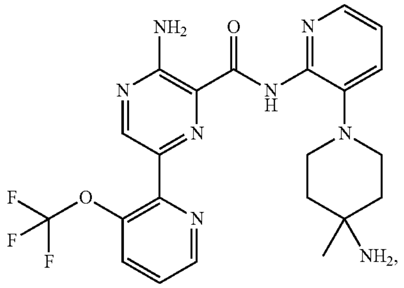

-continued

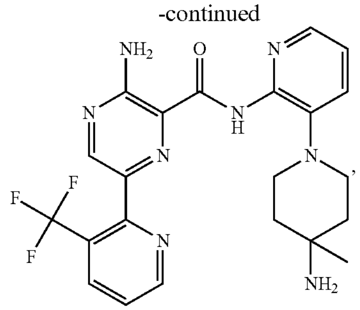

or

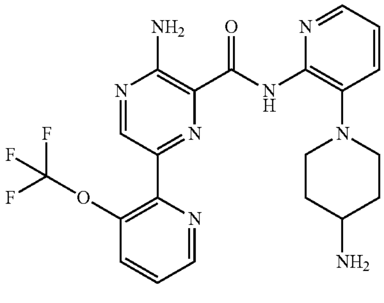

or a pharmaceutically acceptable salt thereof.

As further examples, the protein kinase C inhibitor can be: 3-amino-N-(3-(4-aminopiperidin-1-yl)pyridin-2-yl)-6-(3-(trifluoromethyl)pyridin-2-yl)pyrazine-2-carboxamide; 3-amino-N-(3-(4-aminopiperidin-1-yl)pyridin-2-yl)-6-(3-(trifluoromethoxy)pyridin-2-yl)pyrazine-2-carboxamide; 3-amino-N-(3-(4-amino-4-(methoxymethyl) piperidin-1-yl) pyridin-2-yl)-6-(3-(trifluoromethyl)pyridin-2-yl)pyrazine-2-carboxamide; 3-amino-N-(3-(4-amino-4-(hydroxymethyl) piperidin-1-yl)pyridin-2-yl)-6-(3-(trifluoromethyl)pyridin-2-yl)pyrazine-2-carboxamide; 3-amino-N-(3-(4-amino-4-(hydroxymethyl) piperidin-1-yl)pyridin-2-yl)-6-(3-(trifluoromethoxy)pyridin-2-yl)pyrazine-2-carboxamide; 3-amino-N-(3-(4-amino-4-methylpiperidin-1-yl)pyridin-2-yl)-6-(3-(trifluoromethyl)pyridin-2-yl)pyrazine-2-carboxamide; 3-amino-N-(3-(4-amino-4-methylpiperidin-1-yl)pyridin-2-yl)-6-(3-(trifluoromethoxy)pyridin-2-yl)pyrazine-2-carboxamide; 3-amino-N-(3-(4-amino-4-methylpiperidin-1-yl) pyridin-2-yl)-6-(4-methoxy-3-(trifluoromethyl)pyridin-2-yl)pyrazine-2-carboxamide; 3-amino-N-(3-(4-amino-4-ethylpiperidin-1-yl)pyridin-2-yl)-6-(3-(trifluoromethyl) pyridin-2-yl)pyrazine-2-carboxamide; 3-amino-N-(3-(4-amino-4-methylpiperidin-1-yl)pyridin-2-yl)-6-(3-chloropyridin-2-yl)pyrazine-2-carboxamide; 3-amino-N-(3-(4-amino-4-methylpiperidin-1-yl)pyridin-2-yl)-6-(3-fluoropyridin-2-yl)pyrazine-2-carboxamide; 3-amino-N-(3-(4-amino-4-methylpiperidin-1-yl)pyridin-2-yl)-6-(3-fluoro-4-methoxypyridin-2-yl)pyrazine-2-carboxamide; 3-amino-N-(3-(4-amino-4-(methoxymethyl) piperidin-1-yl)pyridin-2-yl)-6-(3-fluoropyridin-2-yl)pyrazine-2-carboxamide; 3-amino-N-(3-(4-amino-4-methylpiperidin-1-yl)pyridin-2-yl)-6-(3-cyanopyridin-2-yl)pyrazine-2-carboxamide; 3-amino-N-(3-(4-amino-4-ethylpiperidin-1-yl)pyridin-2-yl)-6-(3-(trifluoromethoxy)pyridin-2-yl)pyrazine-2-carboxamide; 3-amino-N-(3-(4-amino-4-methylpiperidin-1-yl) pyridin-2-yl)-6-(3-cyano-4-methoxypyridin-2-yl)pyrazine-2-carboxamide; 3-amino-N-(3-(4-amino-4-(methoxymethyl) piperidin-1-yl)pyridin-2-yl)-6-(3-(trifluoromethoxy)pyridin-2-yl)pyrazine-2-carboxamide; 3-amino-N-(3-(4-amino-4-(2-hydroxyethyl) piperidin-1-yl) pyridin-2-yl)-6-(3-(trifluoromethyl)pyridin-2-yl)pyrazine-2-carboxamide; 3-amino-N-(3-(4-amino-4-(2-hydroxyethyl) piperidin-1-yl)pyridin-2-yl)-6-(3-fluoropyridin-2-yl)

pyrazine-2-carboxamide; 3-amino-N-(3-(4-amino-4-methylpiperidin-1-yl)pyridin-2-yl)-6-(4-cyano-3-fluoropyridin-2-yl)pyrazine-2-carboxamide; 3-amino-N-(3-(4-amino-4-(2-methoxyethyl) piperidin-1-yl)pyridin-2-yl)-6-(3-(trifluoromethyl)pyridin-2-yl)pyrazine-2-carboxamide; (+) 3-amino-N-(3-((cis)-4-amino-3-fluoropiperidin-1-yl) pyridin-2-yl)-6-(3-(trifluoromethoxy)pyridin-2-yl)pyrazine-2-carboxamide; 3-amino-N-(3-(4-aminopiperidin-1-yl)pyridin-2-yl)-6-(3-fluoropyridin-2-yl)pyrazine-2-carboxamide; 3-amino-N-(3-((3 S,4R)-4-amino-3-fluoropiperidin-1-yl) pyridin-2-yl)-6-(3-(trifluoromethoxy)pyridin-2-yl)pyrazine-2-carboxamide; 3-amino-N-(3-(4-amino-4-ethylpiperidin-1-yl)pyridin-2-yl)-6-(3-fluoropyridin-2-yl)pyrazine-2-carboxamide; 3-amino-N-(3-(4-amino-4-methylpiperidin-1-yl)pyridin-2-yl)-6-(4-cyano-3-(trifluoromethyl)pyridin-2-yl)pyrazine-2-carboxamide; 3-amino-N-(3-(4-amino-4-methylpiperidin-1-yl)pyridin-2-yl)-6-(4-ethoxy-3-(trifluoromethyl)pyridin-2-yl)pyrazine-2-carboxamide; 3-amino-N-(3-(4-amino-4-methylpiperidin-1-yl)pyridin-2-yl)-6-(4-chloro-3-(trifluoromethyl)pyridin-2-yl)pyrazine-2-carboxamide; 3-amino-N-(3-(4-amino-4-methylpiperidin-1-yl)pyridin-2-yl)-6-(3-cyano-4-methoxypyridin-2-yl) pyrazine-2-carboxamide; 3-amino-N-(3-(4-aminopiperidin-1-yl)-6-methylpyridin-2-yl)-6-(3-(trifluoromethoxy) pyridin-2-yl)pyrazine-2-carboxamide; 3-amino-N-(3-(4-aminopiperidin-1-yl)-6-methylpyridin-2-yl)-6-(3-(trifluoromethyl)pyridin-2-yl)pyrazine-2-carboxamide; 3-amino-N-(3-(4-amino-3-methoxypiperidin-1-yl)pyridin-2-yl)-6-(3-(trifluoromethoxy)pyridin-2-yl)pyrazine-2-carboxamide; 3-amino-N-(3-(4-amino-4-methylpiperidin-1-yl) pyridin-2-yl)-6-(3-fluoro-4-methylpyridin-2-yl)pyrazine-2-carboxamide; 3-amino-N-(3-(4-amino-4-methylpiperidin-1-yl)pyridin-2-yl)-6-(4-ethoxy-3-fluoropyridin-2-yl)pyrazine-2-carboxamide; 3-amino-N-(3-(4-amino-4-methylpiperidin-1-yl)pyridin-2-yl)-6-(4-(hydroxymethyl)-3-(trifluoromethyl)pyridin-2-yl)pyrazine-2-carboxamide; and 3-amino-N-(3-(4-amino-4-methylpiperidin-1-yl)pyridin-2-yl)-6-(4-(methoxymethyl)-3-(trifluoromethyl)pyridin-2-yl) pyrazine-2-carboxamide; or a pharmaceutically acceptable salt thereof.

In various preferred aspects, the protein kinase C inhibitor can be 3-amino-N-(3-(4-amino-4-methylpiperidin-1-yl) pyridin-2-yl)-6-(3-(trifluoromethyl)pyridin-2-yl)pyrazine-2-carboxamide (Compound A), or a pharmaceutically acceptable salt thereof. The protein kinase C inhibitor can have the structure:

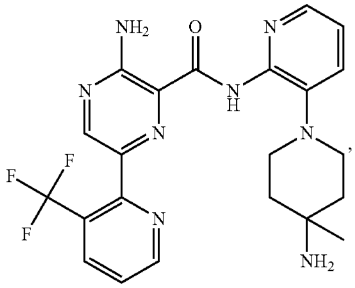

or a pharmaceutically acceptable salt thereof.

The presently described protein kinase C inhibitors represent only a subset of available protein kinase C inhibitors. The combination therapy described herein involves use of a protein kinase C inhibitor having significant potency against PKC isoforms and selectivity for the PKC family as compared to other kinases. Many existing kinase inhibitors are not particularly selective to their target kinome; yet, in some cases, that same cross-reactivity with other non-PKC kinases can be responsible for a biological benefit. For example, sotrastaurin is a PKC inhibitor, but also inhibits GSK-3 beta, which is involved a wide variety of diseases and can play a role in survival of malignant cells. Sotrastaurin is also a pan-selective PKC inhibitor which exhibits high potency across the entire family of PKC isoforms and greater inhibitory activity against classical PKC isoforms than it does against novel PKC isoforms. It has become recognized that differential inhibition of certain PKC isoforms provides differing biological effects, yet the divergent properties of each isoform are not fully understood in all biological systems. As an example of an isoform-specific PKC inhibitor, enzastaurin is selective for classical PKC isoforms, namely, the beta isoform, and it has been investigated as a cancer treatment based on this selectivity. In contrast, the present embodiments of PKC inhibitors are highly potent against novel and classic PKC isoforms and display greater activity against the novel isoforms compared with their activity against classic isoforms. Additional protein kinase C inhibitors are described in U.S. Pat. No. 9,845,309, which is incorporated by reference herewith in its entirety.

Without intending to limit to any particular theory of functioning, various oncogenic states in metastatic uveal melanoma, or arising from a mutation in GNAQ or GNA11, can result in various changes to intracellular DAG and/or $Ca^+$. For example, activated GNAQ or GNA11 can further activate PLC-B and can hydrolyze plasma membrane releasing various PKC signaling agents. The PKC family plays a role in controlling activation of various other enzymatic pathways, including the MAPK pathway, having an activation cascade through RAS, RAF, MEK, and then ERK. Inhibition of PKC can reduce downstream activation of MAPK kinases, resulting in reduced ERK phosphorylation. The anti-proliferative activity of the presently described PKC inhibitors may arise as a result of this reduced MAPK signaling and inhibition of ERK activity. Activation of PKC also phosphorylates MARCKS, which is a more proximal pharmacodynamic biomarker for PKC activation.

Various PKC inhibitors described herein are highly selective for inhibiting PKC family proteins, without having significant cross-reactivity of other non-PKC kinases. In various examples, the PKC inhibitors are more active against novel PKC isoforms over the classical PKC isoforms. While the various selective PKC inhibitors described herein are not thought to act upon the cMET pathway, it has been found that hepatocyte growth factor—the endogenous ligand for cMET—can trigger highly antagonistic effects on the presently described PKC compounds in certain tumor cells. This antagonism is discovered to be the result of competing downstream signaling arising as a result of elevated cMET concentration and use of the presently described PKC inhibitors. The nature of this downstream competition appears to be complex and does not simply correlate due to HGF levels. Such complexity may be due, in part, to the differential action of the various PKC isoforms on interkinome signaling and cMET trafficking. See, e.g., Kang, Protein Kinase C (PKC) Isozymes and Cancer, New Journal of Science, vol. 2014; also, Garg et al., Protein Kinase C And Cancer: What We Know And What We Do Not, Oncogene, vol. 33, 2014, 5225-5237; also, Kermorgant et al., PKC Controls HGF-Dependent C-Met Traffic, Signaling And Cell Migration, EMBO J. 2004 Sep. 29; 23 (19): 3721-3734, each of which is incorporated by reference herewith in its entirety.

The combination therapy described herein can involve use of the presently described protein kinase C inhibitor that highly active against one or more novel PKC isoforms, e.g., delta, epsilon, eta, or theta. In various aspects, the protein kinase C inhibitor can have an $IC_{50}$ of less than or about 5, 10, 15, 20, 25, 30, 35, 40, 45, 40, 50, 60, 70, 80, 90, or 100 nM for one or more, or each, of novel PKC isoforms delta, epsilon, eta, or theta.

In various aspects, the present embodiments of the protein kinase C inhibitor are more active against one or more of novel PKC isoforms delta, epsilon, eta, or theta relative to other PKC isoforms, e.g., relative to non-novel PKC isoforms alpha, beta 1, beta 2, gamma, zeta, and iota. In particular, the present embodiments of the protein kinase C inhibitor have a greater inhibitory activity against each of protein kinase C isoform delta, epsilon, eta, and theta than against classic protein kinase C isoform alpha, beta 1, beta 2, or gamma. As an example, the present embodiments of the protein kinase C inhibitor can exhibit at least a 1-fold, 2-fold, 3-fold, 4-fold, 5-fold, 10-fold, 20-fold, 30-fold, 40-fold, 50-fold, or 100-fold fold lower inhibitory activity against protein kinase C isoforms alpha, beta 1, beta 2, or gamma than against protein kinase C isoform delta, epsilon, eta, or theta. In further examples, the present embodiments of the protein kinase C inhibitor exhibits at least a 1-fold, 2-fold, 3-fold, 4-fold, 5-fold, 10-fold, 20-fold, 30-fold, 40-fold, 50-fold, or 100-fold fold lower inhibitory activity against protein kinase C isoform beta 1 than against protein kinase C isoform theta. As a yet further example, the present embodiments of the protein kinase C inhibitor can have an $IC_{50}$ of less than or about 5, 10, 15, 20, 25, 30, 35, 40, 45, 40, or 50 nM for one or more, or each, of novel PKC isoforms delta, epsilon, eta, or theta, and an $IC_{50}$ of greater than about 20, 25, 30, 35, 40, 45, 50, 60, 70, 80, 90, or 100 nM for one or more, or each, of classical PKC isoforms alpha, beta 1, beta 2, or gamma.

In additional aspects, the present embodiments of the protein kinase C inhibitor are selective for all PKC isoforms relative to other kinases outside the protein kinase C kinome. For example, the present embodiments of the protein kinase C inhibitor can have at least a 100-fold, 200-fold, 300-fold, 400-fold, 500-fold, 1000-fold, 2000-fold, 2500-fold, or 5000-fold lower inhibitory activity against a non-PKC kinase than against one or more, or each novel or classical protein kinase C isoform. As another example, the present embodiments of the PKC inhibitor can have at least a 100-fold, 200-fold, 300-fold, 400-fold, 500-fold, 1000-fold, 2000-fold, 2500-fold, or 5000-fold lower inhibitory activity against a PIM 2, GSK3B, or both, than against one or more, or each, novel or classical protein kinase C isoform. In a further aspect, the present embodiments of the protein kinase C inhibitor can have an $IC_{50}$ of greater than, or about, 1000, 2000, 3000, 4000, 5000, 6000, 7000, 8000, 9000, or 10,000 nM against PIM 2, GSK3β, PKC zeta, PKZ iota, or a combination thereof.

The cMET Inhibitor can be a small molecule inhibitor of cMET. The cMET inhibitor can be an inhibitor of intracellular ATP-cMET ligand-receptor binding. Examples of the cMET inhibitor include crizotinib, capmatinib, cabozantinib, tivantinib, or a combination thereof.

In various aspects, the cMET inhibitor also has activity as an ALK inhibitor, a RAS1 inhibitor, or both. For example, the cMET inhibitor can be crizotinib.

In various further aspects, the cMET inhibitor may have one of the following structures:

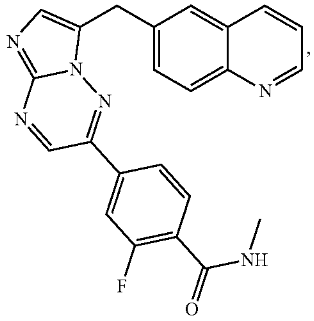

,

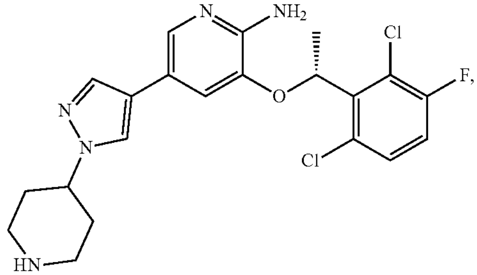

,

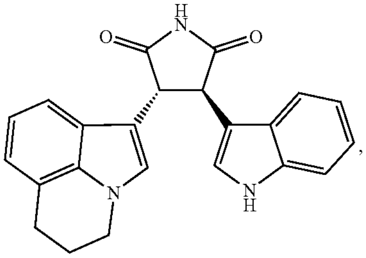

,

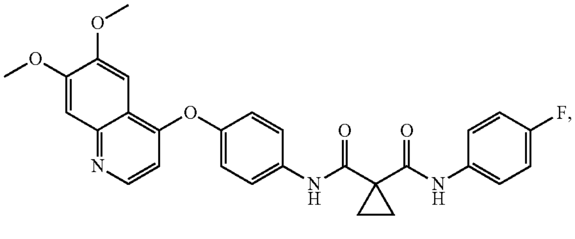

, or a pharmaceutically acceptable salt thereof.

For example, the cMET inhibitor can be:

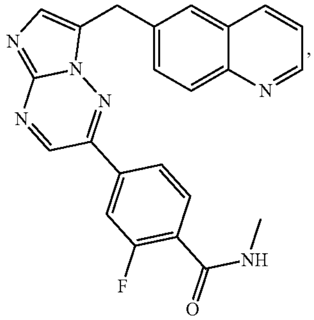 [SMILES: CNC(=O)c1ccc(-c2cnc3ncc(Cc4ccc5ncccc5c4)n3n2)cc1F]

, or a pharmaceutically acceptable salt thereof.

As another example, the cMET inhibitor can be:

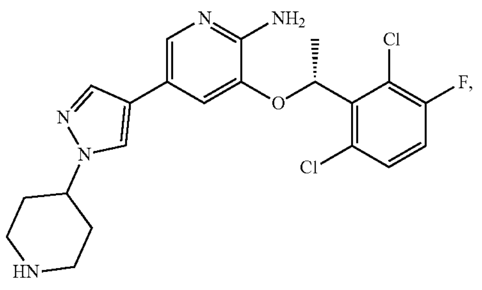 [SMILES: C[C@@H](Oc1cc(-c2cnn(C3CCNCC3)c2)cnc1N)c1c(Cl)ccc(F)c1Cl]

or a pharmaceutically acceptable salt thereof.

Method of Treatment

The present invention provides a method for treating a patient having metastatic uveal melanoma, or having a tumor having a GNAQ or GNA11 mutation ("GNAQ/11 tumor"), including in particular such a GNAQ or GNA11 mutation that activates the PKC signaling pathway, in each case by providing a combination therapy involving a cMET inhibitor and a PKC inhibitor. For example, the method can involve co-administering such as either simultaneously or sequentially administering to the patient the present embodiments of the protein kinase C inhibitor and the cMET inhibitor, including, in particular, one or more of crizotinib, capmatinib, cabozantinib, or tivantinib. The PKC inhibitor can be a compound according to Formula II, as set forth hereinabove. The term "co-administration" is intended to encompass the administration of two or more compounds described herein, e.g., a protein kinase C inhibitor and a cMET inhibitor, to a single patient so that the therapeutic benefits of each of the two or more compounds at least partially overlap.

The PKC inhibitor and the cMET inhibitor can be administered to the patient simultaneously as a single composition, simultaneously as separate compositions, or sequentially as separate compositions. For example, the PKC and cMET inhibitors may be formulated as a single combined composition, such as a tablet, according to the prescribing label regulations for each compound or according to pharmacokinetic and pharmacodynamic studies associated with simultaneous oral administration of the two compounds. Alternatively, a healthcare provider may instruct a patient to take two separate compositions according to label instruction associated with each of the protein kinase C inhibitor and the cMET inhibitor. In one approach, the healthcare provider may instruct a patient to take two separate compositions of a PKC inhibitor and a cMET inhibitor simultaneously or at approximately the same time, e.g., during the same patient care visit, or within 0.5, 1, 2, 3, 4, 5, 10, 15, 20, 30, 60. 120 or 180 minutes or otherwise provide instructions to take separate compositions within a time period indicated by the pharmacodynamic/pharmacokinetic profile, such as the half-lives of the two compositions. Use of the pharmacodynamic/pharmacokinetic profiles of the two inhibitors will enable the healthcare provider to assure that the patient has exposure to detectable amounts, and preferably clinically relevant amounts, of active pharmaceutical ingredient of each of the PKC inhibitor and the cMET inhibitor. In some examples, the PKC inhibitor may be administered before the cMET inhibitor, while in other examples the cMET inhibitor may be administered before the PKC inhibitor. Preferably, the co-administration, whether simultaneous or sequential, results in the combination of the two or more compounds providing an additive, more than additive, or preferably a synergistic benefit to the patient.

The simultaneous or sequential administration of separate doses of the PKC inhibitor and the cMET inhibitor preferably, but not necessarily, may follow the same route of administration. For example, co-administration can include simultaneous, or sequential administration of the protein kinase C inhibitor by an oral route or iv route and administration of the cMET inhibitor by a suppository or iv or ip route. The attending physician may determine the most appropriate route of administration for separate doses of the two inhibitors. Choice may depend upon several factors including the general health and condition of the patient, the ability of the patient to swallow, the ambulatory state of the patent as well as other physical and mental conditions of the patient that may be assessed according to the wisdom of the attending physician.

Administration of separate doses of the PKC and cMET inhibitors may follow a sequential procedures such that the later-administered compound is administered to the patient while the earlier-administered compound has an in vivo concentration of at least or about 0.9, 0.8, 0.7, 0.6, 0.5, 0.4, 0.3, 0.2, 0.1, 0.01, 0.001, 0.0001, or 0.00001 of its $C_{max}$ in the patient. Sequential administration of the later-administered compound may be accomplished prior to the $T_{max}$ of the earlier-administered compound, at about the in vivo $T_{max}$ of the earlier-administered compound, or within about 5×, 10×, 20×, 50×, 100×, or about 1000× the in vivo $T_{max}$ of the earlier-administered compound. The sequential administration of the later-administered compound may be accomplished within a half-life of the earlier-administered compound, at about one-half life of the earlier-administered compound, or within about 2, 3, 4, 5, 6, 7, 8, 9, or 10 half-lives of the earlier-administered compound. As a further example, the protein kinase C inhibitor can be administered to the patient at or within about 1, 2, 3, 4, 5, 6, 7, 8, 9, 10, 11, 21, 24, 36 42, or 48 hours following administration of crizotinib, which has a half-life of about 42 hours. As a yet further example, the protein kinase C inhibitor can be administered to the patient at or within about 0.5, 1, 2, 3, 4, 5, 6, 6.5, 7, 8, 9, 10, 11, 12 or, 13 hours following administration of capmatinib, which has a half-life of about 6.5 hours. In any event, the sequential administration preferably follows a protocol in which the administered PKC and cMET inhibitors provide an additive, more than additive, or synergistic effect, such as an anti-proliferative effect.

Patient Selection

The presently described methods of treating a patient can additionally involve a patient selection step, or a step for determining which course of treatment to provide to a patient. In various aspects, the method involves selecting a patient having metastatic uveal melanoma, or having a tumor having a GNAQ or GNA11 mutation ("GNAQ/11 tumor"), preferably a GNAQ/11 tumor having a mutation that activates the PKC signaling pathway. The GNAQ/11 tumor can be a primary GNAQ/11 tumor or a metastatic GNAQ/11 tumor. Selecting the patient can represent a selection from among a population of patients or can represent selecting a patient at a point of time, or disease state, over the individual patient's course of treatment or disease progression. Thus, patient selection can identify not only which patients should receive the presently described combination therapy, but also when the patients should receive it. In various aspects, patient selection provides the advantage of an improved therapeutic index, for example, by reducing risk, or increasing benefit, to a given patient or patient population.

For example, the present invention provides method of patient selection and treatment, comprising selecting a patient having metastatic uveal melanoma or having a tumor having a GNAQ or GNA11 mutation ("GNAQ/11 tumor"), preferably a GNAQ/11 tumor having a mutation that activates the PKC signaling pathway, and co-administering to the patient a cMET inhibitor and a protein kinase C inhibitor represented by Formula II, as described hereinabove. The GNAQ/11 tumor can be a primary GNAQ/11 tumor or a metastatic GNAQ/11 tumor.

As an example, the method can involve selecting a patient with metastatic uveal melanoma having an elevated cMET presence determined by a biopsy of the uveal melanoma; and co-administering to the patient a cMET inhibitor and the protein kinase C inhibitor represented by Formula II. In yet further examples, the method involves selecting a patient with a tumor with a GNAQ or GNA11 mutation ("GNAQ/11 tumor") having an elevated cMET presence determined by a biopsy of the GNAQ/11 tumor; and co-administering to the patient a cMET inhibitor and the protein kinase C inhibitor represented by Formula II. The GNAQ/11 tumor can be a primary GNAQ/11 tumor or a metastatic GNAQ/11 tumor. As such, the patient selection can comprise each of (i) selecting a patient having metastatic uveal melanoma or a patient having a GNAQ/11 tumor and (ii) selecting a patient having elevated cMET presence determined by a biopsy of the metastatic uveal melanoma or the GNAQ/11 tumor, respectively.

Selection steps can also serve to identify which patients are likely to benefit from the combination therapy and which are not. For example, the selection step can identify which patients should receive the protein kinase C inhibitor as a combination therapy together with the cMET inhibitor, and which patients should receive the protein kinase C inhibitor without a cMET inhibitor, including for example a PKC inhibitor alone or with another combination agent. The selection step can also identify when a given patient should receive the combination therapy or when he or she should receive monotherapy. As such, the selection steps can also serve to identify a course of treatment for a patient.

As a further example, the present invention also provides a method of treating a patient having metastatic uveal melanoma or having a tumor with a GNAQ or GNA11 mutation ("GNAQ/11 tumor"), the method comprising:

assessing cMET presence, in a biopsy of the metastatic uveal melanoma or the GNAQ/11 tumor;

if the cMET presence is elevated in the metastatic uveal melanoma or the GNAQ/11 tumor, then co-administering to the patient a cMET inhibitor and a protein kinase C inhibitor; and if cMET presence is not elevated in the metastatic uveal melanoma or the GNAQ/11 tumor, then administering to the patient the protein kinase C inhibitor without the cMET inhibitor, wherein the protein kinase C inhibitor is represented by Formula II, as described hereinabove.

Assessing cMET Presence cMET is a receptor tyrosine kinase involved in a number of signaling pathways, including the MAPK pathway and PI3K pathway. The natural, endogenous ligand for this receptor is hepatocyte growth factor (HGF). It has been found, however, that when HGF is experimentally added to uveal melanoma cell lines to stimulate cMET expression, only some cell lines exhibit antagonism of the anti-proliferative effect of the PKC inhibitor of Formula II. Even though the concentration of HGF in such experiments is maintained at the same level for all cell lines, it has been discovered that some cell lines had elevated cMET presence while other cell lines did not. Hence, although it is not a limitation of the invention, it is theorized that the complex machinery managing cMET and PKC pathways and ligand/messenger intersections rather than HGF are the significant factors in determining whether or not elevated cMET presence occurs. The present invention is based at least in part on this discovery, that elevated cMET presence corresponds to a tumor subtype that can be advantageously treated with the presently described combination of a protein kinase C inhibitor and a cMET inhibitor.

In various aspects, the present invention provides method of treating a patient having metastatic uveal melanoma, or a tumor with a GNAQ or GNA11 mutation ("GNAQ/11 tumor"), by co-administering a cMET inhibitor and a PKC inhibitor to the patient having an elevated cMET presence as determined by a biopsy of the metastatic uveal melanoma or the GNAQ/11 tumor. The method can involve determining that cMET presence is elevated in a patient's biopsy, for example, to select which patient should receive the combination therapy or to confirm that the combination therapy is suitable in the patient.

For example, the present invention provides method of treating a patient having metastatic uveal melanoma. The method comprises determining the presence of an elevated cMET presence in a biopsy of the metastatic uveal melanoma; and co-administering to the patient a cMET inhibitor and a protein kinase C inhibitor represented by Formula II, as described hereinabove.

As another example, the present invention provides method of treating a patient having a tumor with a GNAQ or GNA11 mutation ("GNAQ/11 tumor"), preferably a GNAQ/11 tumor having a mutation that activates the PKC signaling pathway. The method comprises determining the presence of an elevated cMET presence in a biopsy of the GNAQ/11 tumor; and co-administering to the patient a cMET inhibitor and a protein kinase C inhibitor represented by Formula II, as described hereinabove. The GNAQ/11 tumor can be a primary GNAQ/11 tumor or a metastatic GNAQ/11 tumor.

The term "presence" as used herein refers, qualitatively or quantitatively, to an amount, e.g., concentration or number, of cMET in a given tumor, tissue, whole cell, cell lysate, cell fraction, or cell homogenate. Presence can be determined directly, e.g., by measuring the cMET protein itself such as via IHC, immunoassay or flow cytometry, or indirectly, e.g., by measuring expression levels of cMET via RNA-seq other transcriptome profiling. It is envisaged that, in some examples, presence will refer to cMET mRNA expression levels, or presence will refer to cMET protein levels, or in yet further examples, cMET mRNA expression levels may be used as a proxy for cMET protein levels due to the correlation between mRNA expression and protein presence. Presence can be described in an absolute sense, e.g., in terms of molar concentration, ng/ml, number, density per cell, or expression number, RNA expression level or it can be described in a relative sense comparative to a baseline, such as a calibration standard. For example, "presence" determined by RNA expression level may be compared to RNA expression of a stable "housekeeping gene" also present in the normal and/or melanoma cells of the biopsy and/or present in normal (non-melanoma) cells of a similar type taken from another location within the patient. For example, "presence" determined by cMET protein level may be compared to a baseline cMET protein level taken from healthy tissue of the same type taken from the patient or from similar patients or from a primary uveal melanoma cell culture exhibiting low cMET protein level, or a standard baseline cMET protein level established from a patient population.

More particular aspects for assessing cMET presence can be practiced through techniques such as ELISA, western blotting, IHC—F, IHC—P, immunocytochemistry, immunofluorescence, flow cytometry, mass cytometry, immunoprecipitation. Such techniques can involve use of an anti-cMET antibody. Anti-cMET antibodies suitable for use in ELISA, IHC, immunoprecipitation, western blot, flow cytometry, immunofluorescence, and other techniques are available at Thermo Fisher Scientific (Waltham, MA). The expression level of cMET RNA can be assessed using a cMET RNA-seq transcriptome technique, Nanostring, quantitative PCR or other similar method which would measure the relative levels of cMET mRNA. Such a technique is described in Example 5 below.

When described in unspecified, but relative, terms, cMET presence can be understood as relative to a typical baseline level determined by a pathologist, physician, or other healthcare provider having familiarity or training in understanding cMET levels in the patient population having a tumor of the same tissue type. In various further examples, the baseline can be defined by a reference sample, a reference value, a prior patient state, or a standard. Additionally, cMET presence can be determined based on tissue, whole cells, or the lysate, fraction, or homogenate thereof. In each case, where a relative cMET is described, it is in a comparison between cMET assessments of the same type of sample. For example, cMET is typically located in a transmembrane state, having both an extracellular and intracellular portion, or it can be entirely intracellular, or it can be extracellular, such as in case of a cell lysate. In some samples, cMET may be present as a mixture of such states, but one state will typically be apparent as most relevant for measurement. In the various aspects, presence of cMET may involve determining transmembrane cMET, intracellular cMET, extracellular cMET, or a combination thereof. Unless otherwise indicated, cMET presence in tissue or whole cells refers to transmembrane cMET, i.e., which functions as a cell surface receptor, and cMET presence in a lysate refers to extracellular cMET.

The term "elevated" in the context of cMET presence, refers to an cMET presence greater than baseline. For example, cMET presence can be elevated relative to any, or all, of a healthy state, a prior patient state, a reference sample, a reference value, or a standard. In some cases, elevated cMET can be determined by the opinion or diagnosis of a pathologist, physician, or other healthcare provider having familiarity or training in understanding cMET levels in the patient population having a tumor of the same tissue type.

Assessing cMET presence in the patient's metastatic uveal melanoma, or in the patient's GNAQ/11 tumor, is typically achieved by assessing cMET presence in a biopsy obtained from such patient's metastatic uveal melanoma or GNAQ/11 tumor, respectively. The cMET levels in the biopsy can be assessed by performing measurements on the biopsy itself, or simply by referring to information or a report indicating levels of cMET presence, e.g., cMET expression levels, RNA copy number or cMET concentration, in the biopsy.

The level of cMET presence can be determined any number of ways, including by applying conventional biochemical techniques. While cMET presence as used herein can correspond to total cMET, various techniques used for determining total cMET do not necessarily require direct measurement of total cMET concentration. For example, certain techniques permit measuring RNA expression levels, modified forms of cMET, or biomarkers, in order to determine total cMET concentration.

In various aspects, the method further involves taking obtaining, e.g., extracting or taking, the biopsy from the patient. For example, the biopsy can be obtained by surgical resection, by needle biopsy, such as core needle biopsy, or other methods or approaches known in the art. The biopsy typically can be a solid tumor biopsy. The cells of the biopsy can be isolated, cultured, lysed, fractionated, or homogenized, or a combination thereof. The method can involve taking a single biopsy or taking multiple biopsies. For example, the method can involve obtaining multiple biopsies, or obtaining information about cMET presence in multiple biopsies, taken at separate points of time. Taking multiple biopsies over time can be useful for determining how a patient's disease has progressed and can serve to identify when combination therapy is suitable for a given patient.

In various aspects, assessing cMET presence as a protein or as RNA transcriptome involves contacting the biopsy material with a combination of a ligand specific to cMET and a reporter ligand (labeled ligand) that interacts with the ligand specific for cMET. As used herein, ligand refers to a compound or biological molecule that has a binding interaction with cMET. For example, the ligand can be an antibody specific to cMET or may be an RNA sequence that selectively binds with cMET RNA. Also, the term cMET presence in the context of this section means the cMET protein and/or cMET RNA. The content of the discussion about assessing cMET presence will indicate whether a protein or RNA is being assessed. The ligand can also be a small molecule that binds to cMET. The ligand or antibody can be conjugated to a label or a second ligand capable of associating with the primary ligand may carry a label. Examples of labels include chromogenic, fluorescent, radiologic, or isotopic labels. Anti-cMET antibodies are commercially available from Thermo Fisher Scientific (Waltham, MA) in conjugated, labeled form, and also unconjugated form, which can be labeled using conventional labeling techniques prior to use or can be detected with commercially available reporter ligands. Antibodies can be detected by direct labeling of the antibodies themselves, for example, with radioactive labels, fluorescent labels, hapten labels such as, biotin, or an enzyme such as horse radish peroxidase, alkaline phosphatase, or by use of a second antibody for the primary antibody. Alternatively, an unlabeled primary antibody, specific to cMET, is used in conjunction with a labeled secondary antibody specific for the primary antibody. Alternatively, cMET RNA expression can be measured in the biopsy using RNA-seq, Nanostring, quantitative PCR or other similar method which would measure the relative levels of cMET mRNA. Thresholds and cutoffs of RNA expression are obtained from low and high expressing cMET tissues to determine whether a particular uveal melanoma tissue has high or low cMET RNA expression.

The anti-cMET antibody can be specific to the phosphorylated form of cMET, specific to the unphosphorylated form of cMET, or it can be non-specific regarding phosphorylated or unphosphorylated cMET. The antibody can be specific to human cMET. Because the phosphorylated, unphosphorylated and total cMET proteins are correlated, each will correspondingly yield the appropriate concentration of elevated cMET presence.

In various aspects, cMET presence can be determined from a biopsy prepared in the form of tissue sections, which may be fixed and paraffin-embedded, or which may be frozen. Such tissue sections can be contacted with a labeled antibody to assess presence of cMET in the tissue. When determining relative cMET presence, the tissue sections can be compared to a tissue section from a healthy tissue of the same type from which the biopsy was derived, in either the same patient or a representative patient. The tissue sections can also be compared to a tissue section from an earlier biopsy obtained from the same tumor. For example, cMET presence can be assessed by obtaining an initial biopsy from the metastatic uveal melanoma or the GNAQ/11 tumor of the patient and preparing a first tissue section therefrom; obtaining a subsequent biopsy from the metastatic uveal melanoma or the GNAQ/11 tumor of same site in the patient and preparing a second tissue section therefrom; contacting a labeled cMET antibody with the first tissue section; contacting a labeled cMET antibody with the second tissue section; and determining elevated cMET presence in the second tissue section compared to the first tissue section.

The biopsy preparations can be compared, or scored, according to cMET presence. Such scoring system can be devised relative to earlier levels of cMET in the same tumor in the same patient, relative to cMET levels based on reference samples, or using values that represent a range of cMET levels expected in the given patient population. In this manner, elevated cMET presence can be determined. The scoring system can be based, for example, on a scale of 0 to 4, wherein a score of 0 corresponds to no expression of cMET in the tissue, wherein a score of 1 may correspond to cMET expression in the healthy tissue, wherein tissue exhibiting elevated cMET corresponds to a score of 2 or higher, or a score of 3 or 4. For example, the tissue sections can be evaluated using IHC (immunohistochemistry technique), scored on a scale of 0 to 3 or 4, wherein a score of 0 corresponds to no expression of cMET in the tissue, while a score of 1 may correspond to cMET presence in healthy tissue of the type from which the tumor is derived, and scores of 2, or 3 or 4 corresponds to reference samples having increased cMET presence. In some examples, a score of 1 may refer to a standard cMET level derived from a uveal melanoma tumor in which the presently described combination therapy did not have a synergistic anti-proliferative effect, i.e., a low cMET score. In contrast, a score of 2 or 3 or 4 may refer to a standard cMET level derived from a uveal melanoma tumor in which the combination did exhibit a synergistic anti-proliferative effect, as determined by a Bliss, HSA, or Loewe Synergism/Antagonism model. Other immunoassay techniques are equally applicable and can employ similar scoring systems. Such immunoassay techniques are described in Example 6 of the Experimental Section herein, generally and in particular are preferred approaches for determining the presence of elevated cMET according to each of the various aspects, embodiments and sub-embodiments of the present invention. See also the immunohistochemistry techniques described in Wikipedia at en.wikipedia.org/wiki/immunohistochemistry (2020); and the references cited therein such as J. A. Ramos-Vara, "Technical Aspects of Immunohistochemistry, *Veterinary Pathology,* 42 (4); 405-426 (2005). RNA transcriptome techniques may be used alternatively to determine cMET presence. Such techniques are described in Example 5 of the Experimental Section herein, generally and in particular are preferred approaches for determining the presence of elevated cMET according to each of the various aspects, embodiments and sub-embodiments of the present invention.

As another example, cMET presence can be determined from tumor cells obtained by a biopsy. Tumor cells from the biopsy can be optionally isolated, cultured, lysed, fractionated, or homogenized, or a combination thereof. The cells, or the lysate, fraction, or homogenate thereof, can be contacted with a labeled antibody to assess presence of cMET in the cells. When determining relative cMET presence, the tested cells, lysate, fraction, or homogenate, can be compared to a cell sample from a healthy cells of the same type from which the biopsy was derived, in either the same patient or a representative patient. The cells can also be compared to cells from an earlier biopsy obtained from the same tumor. In other examples, the cells are compared to a reference cell that may be a healthy cell or a primary uveal melanoma cell (e.g., a cell line that does not contain elevated cMET). For example, assessing cMET presence with respect to reference cells can involve first obtaining the biopsy from the metastatic uveal melanoma or GNAQ/11 tumor of the patient and preparing a cell preparation therefrom in the form of a cell isolate, lysate, homogenate, fraction, or a combination thereof. Next, reference cells such as but not limited to 92.1 uveal melanoma cells or healthy cells of the same tissue type as the biopsy are obtained and prepared in the same form the biopsy cell preparation. A labeled cMET antibody used to assess the level of cMET in the biopsy cell preparation and in the reference cell preparation. The levels of cMET are compared to determine whether the biopsy cell preparation contains a level of cMET greater to significantly greater than the cMET level in the reference cell preparation. An IHC technique as cited above may be used to determine this assessment.

In various examples, the cMET presence is elevated in the biopsy by at least or about 25%, 50%, 75%, 100%, 125%, 150%, 200%, 300%, 400%, 500%, 1000%, 2500%, or at least or about 5000% relative to a predetermined level. The predetermined level can correspond to the cMET presence in a healthy uveal cell or healthy cell of the type from which the biopsy is derived in the same patient, relative to an average cMET presence in healthy uveal cells or healthy cells of the type from which the biopsy is derived in the same patient population, relative to a cMET presence in a non-metastatic uveal melanoma cell or non-metastatic GNAQ/11 tumor cell of the type from which the biopsy is derived in the same patient or patient population, relative to an average cMET presence in a non-metastatic uveal melanoma cell or non-metastatic GNAQ/11 tumor cell of the type from which the biopsy is derived in the same patient population, relative to a prior assessed level of cMET presence in an earlier biopsy of the same cell type from the same patient.

Tumors

The presently described methods can involve treating, or selecting, a patient having a proliferative disease, such as metastatic uveal melanoma, or a tumor having a genetic mutation in GNAQ or GNA11 (a "GNAQ/11 tumor"), preferably a GNAQ or GNA11 mutation activating the PKC signaling pathway. The GNAQ/11 tumor can be a primary GNAQ/11 tumor or a metastatic GNAQ/11 tumor. For example, the patient can have metastatic uveal melanoma as determined or diagnosed by a physician, or other healthcare provider, having experience or training in identifying metastatic uveal melanoma. As another example, the patient can have a GNAQ/11 tumor, as determined based on assessing a biopsy from the patient. The GNAQ/11 tumor can be a primary GNAQ/11 tumor or a metastatic GNAQ/11 tumor.

The assessment of a patient biopsy can include DNA sequencing (e.g., next generation sequencing (NGS)) analysis of a solid tumor, or of a liquid biopsy (e.g., a blood biopsy) detecting cell free circulating tumor DNA (cfDNA) or detecting DNA in circulating tumor cells (CTC).

The GNAQ/11 tumor can include one or more of a number of mutations, including a substitution mutation, an insertion mutation, and/or a deletion mutation. In some aspects, the GNAQ or GNA11 mutation is a gain of function mutation. In some aspects, the GNAQ or GNA11 mutation activates the PKC signaling pathway. In various aspects, the GNAQ or GNA11 mutation can be the substitution of glutamine in codon 209 (Q209) and/or a substitution of arginine in codon 183 (R183). The GNAQ or GNA11 mutation can be a substitution other than glutamine in codon 209 (Q209), other than a substitution of arginine in codon 183 (R183), or other than both. In some aspects, the GNAQ mutation is one of Q209P, Q209L, Q209H, Q209K, or Q209Y, or the GNA11 mutation is one of Q209P, Q209L, Q209K or Q209H. In further aspects, the GNAQ mutation can be R183Q, or the GNA11 mutation can be R183C or R183H. In yet further examples, the GINAQ or GNA11 mutation is at one or more of R256, L279, R166, A168, R210, R213, R166, A231, A342, D333, G171, R147, R73, T47, E191, E221, R149, T175, T379, T85, A86, E163, D195, E319, E191, E280, E49, P293, R300, R338, R60, D155, D205, D321, 1226, R37, or V240. In further examples, the GNAQ/11 tumor can comprise one or more of a Q209P, Q209L, Q209H, Q209K, Q209Y, or R183Q mutation in GNAQ, or the GNAQ/11 tumor can comprise one or more of a Q209P, Q209L, Q209H, or Q209K mutation in GNA11. Additional examples of mutations in GNAQ or GNA11 are described in WO 2020/146355, which is incorporated by reference herewith in its entirety.

In various aspects, the GNAQ/11 tumor is primary uveal melanoma or metastatic uveal melanoma.

In various aspects, the GNAQ/11 tumor can be a non-uveal tumor, for example a pancreatic tumor, stomach tumor, colorectal tumor, uterine tumor, cervical tumor, bladder tumor, hepatocellular carcinoma, head and neck tumor, prostate tumor, breast tumor, lung adenocarcinoma, or cutaneous melanoma. In other aspects, the tumor is a tumor of the central nervous system, such as a glioblastoma. In further aspects, the GNAQ/11 tumor is a non-uveal tumor, a non-melanocytic tumor, or a non-uveal, non-melanocytic tumor. In some aspects, the tumor is a carcinoma. For example, the tumor can be a pancreatic adenocarcinoma, stomach adenocarcinoma, cervical carcinoma, and lung adenocarcinoma. In various aspects, the aforementioned tumors can be metastatic, or they can be non-metastatic. In some aspects, the tumor is a non-metastatic, non-uveal tumor. For example, the tumor can be other than metastatic uveal melanoma. In yet further examples, the tumor is a metastatic tumor.

For example, the GNAQ/11 tumor can be a solid tumor that is metastasized to a secondary site, such as the liver. As another example, the GNAQ/11 tumor can be metastatic uveal melanoma that is metastasized to the liver. In further aspects, the GNAQ/11 tumor is at high risk of recurring, or metastasizing, e.g., as determined by a gene expression profile such as DecisionDx® as available from Castle Biosciences (Friendswood, TX). In some aspects, the method involves selecting a patient having a high risk of uveal melanoma recurrence or metastasis, e.g., as determined by a pathologist, physician, or other healthcare provider having familiarity or training in understanding risk of recurrence or metastasis of the type of tumor, such as uveal melanoma or a GNAQ/11 tumor.

In various aspects, the GNAQ/11 tumor is metastatic and metastasized to a secondary site that has an HGF concentration of from about 0.1 ng/ml to about 1,000 ng/ml. In another example, the patient can have metastatic uveal melanoma that is metastasized to, or at risk of metastasizing to, a secondary site having an HGF concentration of from about 0.1 ng/ml to about 1,000 ng/ml. Such HGF concentrations can be, for example, 0.1 ng/ml to about 500 ng/ml, 1 ng/ml to about 500 ng/ml, 1 ng/ml to about 100 ng/ml, 1.5 ng/ml to about 100 ng/ml, 3 ng/ml to about 100 ng/ml, 5 ng/ml to about 100 ng/ml, 7 ng/ml to about 100 ng/ml, 10 ng/ml to about 100 ng/ml, 15 ng/ml to about 100 ng/ml, 20 ng/ml to about 100 ng/ml, 1 ng/ml to about 30 ng/ml, 1.5 ng/ml to about 30 ng/ml, 3 ng/ml to about 30 ng/ml, 5 ng/ml to about 30 ng/ml, 7 ng/ml to about 30 ng/ml, 10 ng/ml to about 30 ng/ml, 15 ng/ml to about 30 ng/ml, 20 ng/ml to about 30 ng/ml, 1 ng/ml to about 16 ng/ml, 1.5 ng/ml to about 16 ng/ml, 3 ng/ml to about 16 ng/ml, 5 ng/ml to about 16 ng/ml, 7 ng/ml to about 16 ng/ml, or 10 ng/ml to about 16 ng/ml. For example, the HGF concentration can be about, or at least, 0.5, 1.0, 1.5, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 50.0, 60.0, 70.0, 80.0, 90.0, or about or at least 100.0 ng/ml. In some aspects, the metastatic uveal melanoma or the GNAQ/11 tumor can be a metastatic tumor with a situs in the liver—i.e., a liver metastasis of a prior primary tumor, e.g., histologically originating from another tissue.

In another aspects, the GNAQ/11 tumor can lack one or more activating mutations in BRAF, KRAS, or EGRE, or the GNAQ/11 tumor can have a low load of mutations in one or more of BAP1, SF3β1, E1F1AX, TERT, BRAF, CDKN2A, NRAS, KRAS, or EGRF.

Assessing Genetic Mutation

Aspects of the present invention can involve assessing whether a patient, tumor, or biopsy, exhibits a genetic mutation in GNAQ or GNA11. Such an assessment may involve identifying GNAQ or GNA11 mutations in the patient, for example in a solid tumor biopsy, or in a liquid biopsy (e.g., blood biopsy), for example by identifying circulating cell free tumor DNA (cfDNA) or DNA in circulating tumor cells (CTC's) in the patient, which can be acquired for example by obtaining a liquid sample from the patient. The liquid sample can be a hematologic sample. Genetic mutation can also be assessed from the patient's solid tumor, which would typically involve obtaining a tissue biopsy from the tumor.

Determining whether a patient, tumor, or biopsy has a specific mutation, for example, a GNAQ or GNA11 genetic mutation, can include collecting and/or analyzing a patient sample. Patient samples of interest include, for example, carcinoma tissue, cancer tissue, solid tumor tissue, tumor tissue, body tissue, blood, serum, plasma, or body fluid, for example, circulating blood containing tumor DNA, obtained from the patient. Patient samples used in a method described herein can also include tissue samples such as, but not limited to, gastrointestinal, mucosal, submucosal, intestinal, esophageal, ileal, rectal, cervical, colonic, epidermal, lung, thymus, pancreatic, stomach, rectal, cutaneous, subcutaneous, or lymphatic samples. Samples may also include cellular samples, for examples, cutaneous cell samples. The presence of a genetic mutation of interest in a sample from a patient may be determined using various assays. For example, in various methods, a genetic mutation may be determined by nucleotide analysis, for example, genetic sequencing, Southern blotting, FISH, high-throughput sequencing, phage display, shotgun sequencing, PCR, or RT-PCR. Genetic mutation can also be determined by analyzing mRNA, protein levels, or nucleotide levels, or performing dynamic allele-specific hybridization techniques. Suitable techniques for assessing genetic mutation are described in WO 2020/146355, which is incorporated by reference herewith in its entirety.

Assessing HGF

According to yet further aspects of the invention, the method can involve assessing hepatocyte growth factor (HGF) levels in the patient's tumor, a biopsy of the tumor, or in non-tumor tissue in which the tumor is located. Some types of tumors cells can secret HGF which can trigger cMET antagonistic activity against the presently described protein kinase C inhibitor in certain types of tumors. In some aspects, HGF is secreted by the tumor cells, while in other aspects, the HGF is secreted by tumor tissue, or non-tumor tissue, in which the tumor cells are located. Such assessments of HGF can be performed, for example, by enzyme-linked immunosorbent assay (ELISA). For example, an HGF ELISA kit is available from Thermo Fisher Scientific (Waltham, MA).

In various aspects, the patient has a metastatic uveal melanoma, or a GNAQ/11 tumor, having an HGF concentration in the biopsy of about 0.1 ng/ml to about 1,000 ng/ml. The biopsy can be a tissue biopsy or a surgical resection, or a combination of both. In some aspects, the method further involves selecting a patient having metastatic uveal melanoma, or a GNAQ/11 tumor, that has an HGF concentration of about 0.1 ng/ml to about 1,000 ng/ml as determined by assessing a biopsy of the metastatic uveal melanoma, or the GNAQ/11 tumor. Such HGF concentrations can be, for example, 0.1 ng/ml to about 500 ng/ml, 1 ng/ml to about 500 ng/ml, 1 ng/ml to about 100 ng/ml, 1.5 ng/ml to about 100 ng/ml, 3 ng/ml to about 100 ng/ml, 5 ng/ml to about 100 ng/ml, 7 ng/ml to about 100 ng/ml, 10 ng/ml to about 100 ng/ml, 15 ng/ml to about 100 ng/ml, 20 ng/ml to about 100 ng/ml, 1 ng/ml to about 30 ng/ml, 1.5 ng/ml to about 30 ng/ml, 3 ng/ml to about 30 ng/ml, 5 ng/ml to about 30 ng/ml, 7 ng/ml to about 30 ng/ml, 10 ng/ml to about 30 ng/ml, 15 ng/ml to about 30 ng/ml, 20 ng/ml to about 30 ng/ml, 1 ng/ml to about 16 ng/ml, 1.5 ng/ml to about 16 ng/ml, 3 ng/ml to about 16 ng/ml, 5 ng/ml to about 16 ng/ml, 7 ng/ml to about 16 ng/ml, or 10 ng/ml to about 16 ng/ml. For example, the HGF concentration can be about, or at least, 0.5, 1.0, 1.5, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 50.0, 60.0, 70.0, 80.0, 90.0, or about or at least 100.0 ng/ml.

Pharmaceutical Product

Aspects of the present invention further provide a pharmaceutical product comprising a protein kinase C inhibitor, a cMET inhibitor, and a pharmaceutically acceptable carrier.

The pharmaceutical product can include one or more pharmaceutical compositions, in which the protein kinase C inhibitor and the cMET inhibitor can be formulated together or separately. For example, the pharmaceutical product can include a single pharmaceutical composition which comprises the protein kinase C inhibitor, the cMET inhibitor, and a pharmaceutically acceptable carrier. In such examples, the pharmaceutical product can be represented by a single dosage form comprising the protein kinase C inhibitor, the cMET inhibitor, and a pharmaceutically acceptable carrier.

In further examples, the pharmaceutical product can contain a first pharmaceutical composition comprises the protein kinase C inhibitor, and a second pharmaceutical composition comprising the cMET inhibitor, each independently having a pharmaceutically acceptable carrier.

The pharmaceutical product can include "fixed combinations" and "non-fixed combinations" of two or more active ingredients, such as the protein kinase C inhibitor and the cMET inhibitor. The term "fixed combination" means that the active ingredients, e.g., the protein kinase C inhibitor and the cMET inhibitor, are formulated as a single pharmaceutical composition. For example, a fixed combination can have the protein kinase C inhibitor and the cMET inhibitor in the same unit dosage form (e.g., capsule, tablet, or sachet). The terms "non-fixed combination" refers to two or more active ingredients, e.g., the protein kinase C inhibitor and the cMET inhibitor, that are formulated independently as separate pharmaceutical compositions, and which can be administered to the patient separately. In various aspects, each active ingredient of a non-fixed combination is administered within a time period that allows the protein kinase C inhibitor and the cMET inhibitor to show a cooperative effect, e.g., an additive, more than additive, or synergistic effect. A non-fixed combination can also include use of a single agent together with one or more fixed combination products, where each independent formulation has distinct amounts of the active ingredients contained therein. It should thus be understood that the pharmaceutical products includes examples where the active ingredients, e.g., the protein kinase C inhibitor and the cMET inhibitor, will be administered as entirely separate pharmaceutical dosage forms. In various examples, the protein kinase C inhibitor and the cMET inhibitor can each be in independent pharmaceutical compositions that are sold independently of each other.

The independent parts of the pharmaceutical product can be administered simultaneously or chronologically staggered, that is the individual parts of the pharmaceutical product can each be administered at the same, or different, time points and at the same, or different, time intervals between administration of any given component. For example, the time intervals for the dosing can be chosen such that the effect on the treated disease with the combined use of the protein kinase C inhibitor and the cMET inhibitor is larger/greater than the effect obtained by use of only one of the protein kinase C inhibitor or the cMET inhibitor.

In various aspects, the pharmaceutical product comprises a protein kinase C inhibitor, a cMET inhibitor, and a pharmaceutically acceptable carrier, wherein the protein kinase C inhibitor is represented by Formula II, as described hereinabove.

In various aspects, the pharmaceutical product includes the protein kinase C inhibitor and the cMET inhibitor formulated together in a single unit dosage form comprising one or more pharmaceutically acceptable carrier.

In further aspects, the pharmaceutical product includes the protein kinase C inhibitor and the cMET inhibitor formulated into two separate unit dosage forms, each having an independently selected pharmaceutically acceptable carrier.

The pharmaceutical product can include one or more pharmaceutically acceptable carrier. The pharmaceutically acceptable carrier can be a carrier is useful in preparing a pharmaceutical composition that is generally safe, non-toxic and neither biologically nor otherwise undesirable. For example, the carrier can be acceptable for human pharmaceutical use. A product or composition containing a pharmaceutically acceptable carrier can include one or more of such carriers. Examples of pharmaceutically acceptable carriers include solid carriers, solvents, non-solvent liquid carriers, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, combinations thereof, or other carriers. (See, Remington's Pharmaceutical Sciences, 18th Ed. Mack Printing Company, 1990, pp. 1289-1329). Some examples of materials which can serve as pharmaceutically acceptable carriers include: (1) sugars, such as lactose, glucose, and sucrose; (2) starches, such as corn starch, potato starch, and substituted or unsubstituted (3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen free water; (17) isotonic saline; (18) Ringer's solution; (19) ethyl alcohol; (20) phosphate buffer solutions; and (21) other non-toxic compatible substances employed in pharmaceutical formulations.

It can be appreciated that the various disclosed methods, pharmaceutical product, and kit may include the PKC inhibitor and the cMET inhibitor as part of a pharmaceutical composition. Such composition, for example, may be administering as a dosage unit form. A pharmaceutical composition should be formulated to be compatible with its intended route of administration. It will be appreciated that the presently described compounds and compositions may be administered by various administration routes, for example, orally or parenterally or rectally or vaginally. Administration can be via injection, for example subcutaneous, intrapancreatic, intravenous, intramuscular, intraperitoneal, intrathecal, intraperitoneal, intraocular, or intrasternal injection. Further examples include infusion techniques, inhalation spray, sublingual, dermal, rectal, or ophthalmic administration, e.g., in the form of eye drops.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

Solid dosage forms for oral administration may include capsules, tablets, pills, powders, and granules. In such solid dosage forms, the active agent may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:

(1) fillers or extenders, such as starches, cyclodextrins, lactose, sucrose, glucose, mannitol, and/or silicic acid;
(2) binders, such as, for example, carboxymethylcellulose, alginates, gelatin, polyvinyl pyrrolidone, sucrose, and/or acacia;
(3) humectants, such as glycerol;
(4) disintegrating agents, such as agar-agar, calcium carbonate, potato or tapioca starch, alginic acid, certain silicates, and sodium carbonate;
(5) solution retarding agents, such as paraffin;
(6) absorption accelerators, such as quaternary ammonium compounds;
(7) wetting agents, such as, for example, acetyl alcohol and glycerol monostearate; (8) absorbents, such as kaolin and bentonite clay;
(9) lubricants, such a talc, calcium stearate, magnesium stearate, solid polyethylene glycols, sodium lauryl sulfate, and mixtures thereof; and
(10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents. Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The active agent can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. Examples lipids are phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N. W., p. 33 et seq. (1976).

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof. Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane. A compound useful for application of methods of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The pharmaceutical compounds and compositions may be "systemically" or "peripherally" administered meaning administration such that it enters the patient's system in a manner such that it is subject to metabolism and other like processes, for example, subcutaneous administration. The phrase "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound useful for practice of methods of the invention, it is desirable to slow the absorption of the compound from subcutaneous or intramuscular injection. For example, delayed absorption of a parenterally administered drug form is accomplished by dissolving or suspending the drug in an oil vehicle.

In various aspects, the presently described compounds can be in the form of pharmaceutically acceptable salts. Such salts can be acid or metal salts, e.g., alkali or alkali earth salts. Salts can be prepared in situ during the final isolation and purification of the compound by separately reacting the base or acid functions in the compound with a suitable organic or inorganic acid or base, respectively. Representative salts include, but are not limited to, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalene-sulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of compound of the present disclosure by reacting carboxylic acid moieties with a suitable base such as the hydroxide, carbonate or bicarbonate of a pharmaceutically acceptable metal cation or with ammonia, or an organic primary, secondary or TERTiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethyl-amine, trimethylamine, triethylamine, ethylamine, and the like. Other representative organic amines useful for the formation of base addition salts include diethylamine, ethylenediamine, ethanolamine, diethanolamine, piperazine and the like.

The present disclosure also provides a kit comprising the protein kinase C inhibitor, the cMET inhibitor, and instructions for using the protein kinase C inhibitor and the cMET inhibitor together in a combination therapy. In other aspects, the kit can include a pharmaceutical composition comprising the protein kinase C inhibitor and a pharmaceutically acceptable carrier, together with a probe, or reference standard, for assessing cMET presence. Such kit may further contain a cMET inhibitor. For example, the kit can include the presently described pharmaceutical product, the protein kinase C inhibitor and the cMET inhibitor, together with instructions for their use in combination therapy, or together with instructions for assessing cMET presence.

For example, the kit can comprise a protein kinase C inhibitor and a cMET inhibitor, which are formulated together, or separately, into one or more pharmaceutical compositions, each of which comprises a pharmaceutically acceptable carrier. The kit can further comprise instructions for using the protein kinase C inhibitor and the cMET inhibitor together in a combination therapy. The protein kinase C inhibitor is represented by Formula II, as described hereinabove.

The present disclosure also provides a kit having a probe or a reference standard for assessing cMET presence. The probe can be labeled antibody for cMET. The reference standard for assessing cMET presence can comprise an amount of cMET, e.g., as derived from normal uveal cells.

For example, the kit can comprise a pharmaceutical composition comprising a protein kinase C inhibitor and a pharmaceutically acceptable carrier, and a probe, or reference standard, for assessing cMET presence. The protein kinase C inhibitor can be represented by Formula II, as described hereinabove.

The present disclosure also provides various uses of the pharmaceutical products, kits, or compositions described herein, such as use of the combination of a protein kinase C inhibitor and a cMET inhibitor for the preparation of a medicament for treating, preventing, or otherwise alleviating a symptom of a proliferative disease described herein, such as metastatic uveal melanoma or a tumor having a mutation in GNAQ or GNA11. The invention also provides use of the pharmaceutical product, kit, or various described compositions for treating, preventing, or alleviating a symptom of a proliferative disease described herein, such as metastatic uveal melanoma or a tumor having a mutation in GNAQ or GNA11. For example, use of a pharmaceutical product, kit, or composition comprising a protein kinase C inhibitor and a cMET inhibitor, for reducing proliferation, reducing growth, or reducing disease progression, of metastatic uveal melanoma or a tumor having a mutation in GNAQ or GNA11.

The present invention also provides the combination of a protein kinase C inhibitor and a cMET inhibitor, e.g., as a pharmaceutical product, kit, or composition, for treating a proliferative disease described herein, such as metastatic uveal melanoma or a tumor having a mutation in GNAQ or GNA11.

Dosing

The presently described compounds and their pharmaceutical compositions can be administered according to the methods described herein through use of various forms, depending on the disorder to be treated and the age, condition, and body weight of the patient, as is well known in the art. As is consistent, recommended and required by medical authorities and the governmental registration authority for pharmaceuticals, administration is ultimately provided under the guidance and prescription of an attending physician whose wisdom, experience and knowledge control patient treatment.

The compounds can be formulated in a form suitable for the intended mode of administration. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route or other similar transmucosal route, they may be formulated as drops or ointments.

Although the dosage can vary depending on the symptoms, age and body weight of the patient, the gender of the patient, the nature and severity of the disorder to be treated or prevented, the route of administration and the form of the drug, in general, a daily dosage of from 0.0001 to 2000 mg, preferably 0.001 to 1000 mg, more preferably 0.001 to 500 mg, especially more preferably 0.001 to 250 mg, most preferably 0.001 to 150 mg of the compound is recommended for an adult human patient, and this may be administered in a single dose or in divided doses. Alternatively, a daily dose can be given according to body weight such as 1 nanogram/kg (ng/kg) to 200 mg/kg, preferably 10 ng/kg to 100 mg/kg, more preferably 10 ng/kg to 10 mg/kg, most preferably 10 ng/kg to 1 mg/kg. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

Actual dosage levels of the compound(s) useful for application of methods of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound useful for application of methods of the invention in a pharmaceutically acceptable mixture will vary depending on several factors, including the dosage of the compound to be administered, the pharmacokinetic characteristics of the compound(s) employed, and the route of administration.

In general, the compositions useful for application of methods of this invention may be provided in an aqueous solution containing about 0.1-10% w/v of a compound disclosed herein, among other substances, for parenteral administration. Typical dose ranges are those given above and may preferably be from about 0.001 to about 500 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

The protein kinase C inhibitor can be administered, or present in the pharmaceutical composition, product, or kit, at a dose of about 1, 25, 50, 100, 150, 200, 250, 300, 400, 450, 500, 600, 700, or 800 mg. The protein kinase C inhibitor can be administered once, twice, or three times per day, or once every two days. For example, the protein kinase C inhibitor can be administered twice a day ("βID").

In various aspects, the protein kinase C inhibitor is administered according to a dosing regimen comprising a dosing cycle comprising a first dosing series, followed by a second dosing series, wherein: (a) the first dosing series comprises a dose of about 200 mg βID of compound (I), or a pharmaceutically acceptable salt thereof, and (b) the second dosing series comprises a dose of about 400 mg βID of compound (I), or a pharmaceutically acceptable salt thereof. In various examples, the length of the first dosing series is 5 to 10 days, and the length of the second dosing series is 18 to 23 days; and the length of first dosing cycle comprising first dosing series and second dosing series is 28 days. Additional example dosages and dosing regimens are described in In various aspects, the protein kinase C inhibitor can be 3-amino-N-(3-(4-amino-4-methylpiperidin-1-yl)pyridin-2-yl)-6-(3-(trifluoromethyl)pyridin-2-yl)pyrazine-2-carboxamide administered at a dose of about 50 mg βID, 100 mg βID, 150 mg βID, 200 mg βID, 250 mg βID, 300 mg βID, 350 mg βID, or 400 mg βID.

The cMET inhibitor can be administered, or present in the pharmaceutical composition, product, or kit, at a dose of about 1, 10, 50, 100, 200, 300, 400, 500, 600, 700, or 800 mg. The cMET inhibitor can be administered once, twice, or three times per day, or every two days. For example, the cMET inhibitor can be administered at 200, 250, 300, 350, or 400 mg twice per day. As a further example, the cMET inhibitor can be capmatinib administered at 400 mg orally twice per day. As another example, the cMET inhibitor can be crizotinib administered at 200 mg, or 250 mg, orally twice per day.

Unless otherwise specified, the weight or dosage referred to herein for a particular compound of the disclosure (e.g., Compound A) is the weight or dosage of the compound itself, not that of a salt thereof, which can be different to achieve the intended therapeutic effect. In various aspects of the pharmaceutical products and compositions described herein, the protein kinase C inhibitor and the cMET inhibitor can be present at a relative weight ratio of about 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or about 1:10.

In various aspects, the patient has metastatic uveal melanoma or a GNAQ/11 tumor, and the protein kinase C inhibitor is administered in an amount that when taken together with the cMET inhibitor provides a therapeutic benefit greater than that achieved by either compound alone at the same amounts. Such therapeutic benefit may be more than additive compared to that which is achieved by either compound alone at the same amounts. In some aspects, use of the combination achieves a therapeutic benefit whereas use of either compound alone provides no therapeutic benefit.

The presently described methods, pharmaceutical products, and kits, can provide various therapeutic benefits in a patient having metastatic uveal melanoma or having a GNAQ/11 tumor. For example, in various aspects, co-administration of the PKC inhibitor and the cMET inhibitor can be effective to reduce cell proliferation, or reduce growth, of a GNAQ/11 tumor in a patient. In various further aspects, co-administration of the PKC inhibitor and the cMET inhibitor can be effective to reduce cell proliferation, reduce growth, or reduce progression of, metastatic uveal melanoma. In a further example, the presently described combination therapy can be effective to treat metastatic disease or prevent metastatic disease progression.

For example, where the patient has a GNAQ/11 tumor, the protein kinase C inhibitor can be administered in an amount that when taken together with the cMET inhibitor reduces proliferation, growth, or metathesis of the GNAQ/11 tumor, whereas the protein kinase C inhibitor administered at the same amount alone does not reduce proliferation, growth, or metathesis of the GNAQ/11 tumor in the patient. Further, where the patient has metastatic uveal melanoma, the protein kinase C inhibitor can be administered in an amount that when taken together with the cMET inhibitor reduces proliferation, growth, or metathesis of the metastatic uveal melanoma, whereas the protein kinase C inhibitor administered at the same amount alone does not reduce proliferation, growth, or metathesis of the metastatic uveal melanoma in the patient. In another example, the patient has GNAQ/11 tumor, and the cMET inhibitor is administered in an amount that when taken together with the protein kinase C inhibitor reduces proliferation, growth, or metathesis of the GNAQ/11 tumor, whereas the cMET inhibitor administered at the same amount alone does not reduce proliferation, growth, or metathesis of the GNAQ/11 tumor in the patient. In a yet further example, the patient has metastatic uveal melanoma, and the cMET inhibitor is administered in an amount that when taken together with the protein kinase C inhibitor reduces proliferation, growth, or metathesis of the metastatic uveal melanoma, whereas the cMET inhibitor administered at the same amount alone does not reduce proliferation, growth, or metathesis of the metastatic uveal melanoma in the patient.

In various aspects, the protein kinase C inhibitor, the cMET inhibitor, or both, are administered to the patient without activating BRAF, KRAS, ERK, GSK3-beta, PIM 2, or EGRF.

In various further aspects, the presently described co-administered PKC inhibitor and cMET inhibitor are provided to the patient in therapeutically effective amounts to treat, prevent, or ameliorate a symptom of, the disease. The terms "effective amount" or "therapeutically effective amount," as used herein, refer to an amount of a compound described herein, e.g., Compound (A) or a pharmaceutical composition comprising a compound described herein, being administered in an amount sufficient to treat the disease. An appropriate "effective" amount in any individual case may be determined using techniques, such as a dose escalation study. In connection with the administration of the drug, an "effective amount" indicates an amount that results in a beneficial effect for patients, such as an improvement of symptoms, a cure, a reduction in disease load, reduction in tumor mass or cell numbers, extension of life, improvement in quality of life, or other effect generally recognized as positive by medical doctors familiar with treating the particular type of disease or condition. A combination product, e.g., a fixed combination dosage form comprising two or more compounds, has an effective amount corresponding to an amount of the total combined formulation, and each individual component also has an effective amount corresponding to the individual component, used alone or in the combination.

EXAMPLES

The following examples are illustrative and are not intended to limit the scope or content of the disclosure in any way.

Active Agents

Crizotinib can be obtained from Sigma-Aldrich (St. Louis, MO). Capmatinib can be obtained from Novartis International AG (Basel, Switzerland). Compound A, which corresponds to 3-amino-N-(3-(4-amino-4-methylpiperidin-1-yl)pyridin-2-yl)-6-(3-(trifluoromethyl)pyridin-2-yl)pyrazine-2-carboxamide, can be obtained from IDEAYA Biosciences (South San Francisco, CA). Compound A is depicted at ¶0073 and has the structure

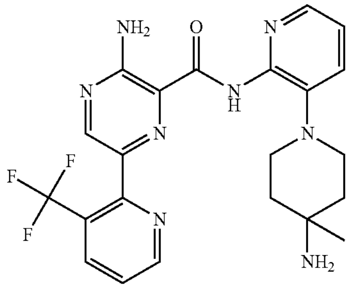 [SMILES: CC1(N)CCN(c2cccnc2NC(=O)c2nc(-c3ncccc3C(F)(F)F)cnc2N)CC1]

Cell Lines

MEL-202 cells and 92.1 cells can be purchased from Sigma-Aldrich (St. Louis, MO). MM28 cells can be obtained from the American Type Culture Collection (ATCC) (Manassas, VA) (Accession No. CRL-3295).

The 92.1 cell line is derived from a primary uveal melanoma, the MEL-202 cell line is derived from a uveal melanoma that recurred in the eye after prior irradiation, and MM28 is derived from metastatic uveal melanoma cells. Each tested cell line corresponds to a GNAQ/11 tumor, i.e., each has one or more mutation in GNAQ or GNA11.

Primary uveal melanoma cell lines, MEL-202 and 92.1 cells, were maintained in 10% FBS/RPMI media and MM28 cells, derived from a metastatic uveal melanoma liver tumor, were maintained in 20% FBS/RPMI media in a humidified incubator at 37° C. with 5% $CO_2$.

Cell viability measurements: For all experiments, cell viability was measured using the Cell Titer-Glo Luminescent Cell Viability Assay kit (Promega) on day 3 for MEL-202 and 92.1 cells, and at day 5 for MM28 cells. Luminescence was read using a plate reader (TECAN). Average luminescence of cells treated with DMSO was set to 100% and the % viable cells were calculated accordingly. Synergy/antagonism was analyzed using Combenefit software. Single agent HGF or crizotinib graphs were analyzed using GraphPad. Interactions between various combinations were evaluated using Bliss, HSA, and Loewe synergy/antagonism models. Uveal melanoma cells (92.1, MEL-202, and MM28) were treated in quadruplicate with a matrix of hepatocyte growth factor (HGF) and Compound A, each at various titrations, to determine their synergy, additivity, or antagonism using Bliss, HSA, and Loewe models. Cell viability was measured by CTG three days/five days after treatment.

Examples 1 and 2

IDE 196-HGF Combination and IDE 196-cMET Inhibitor Combination

Treatment conditions for IDE196-HGF combination: MEL-202, MM28 and 92.1 cells were seeded 24 h before treatment at 2500-5000 cells/well in 10% RPMI media in white 96-well with clear bottom plates. After 24 hrs, the media was changed to 2% FBS/RPMI media. Further, the cell lines were screened for sensitivity to the PKC inhibitor, IDE196 alone or in combination with Hepatocyte growth factor (HGF) (Peprotech); at increasing doses according to Table 1 using a TECAN digital dispenser.

TABLE 1

| MEL-202, 92.1 & MM28 | |
|---|---|
| HGF (ng/ml) in DMSO | IDE 196 nM (Compound A) in DMSO |
| 0.14 | 0.64 |
| 0.41 | 3.2 |
| 1.23 | 16 |
| 3.70 | 80 |
| 11.11 | 400 |
| 33.33 | 2000 |
| 100.00 | 10000 |

Treatment conditions for IDE196-MET Inhibitor combination: MEL-202, MM28 and 92.1 cells were seeded 24 h before treatment at 2500-5000 cells/well in white 96-well with clear bottom plates. After 24 hrs, the media was changed to 2% FBS/RPMI media containing 1.23 ng/ml HGF. Crizotinib or Capmatinib and IDE196 were immediately dispensed using a TECAN digital dispenser at increasing doses according to Table 2.

TABLE 2

| MEL-202, 92.1, MM28 | |
|---|---|
| Crizotinib/ Capmatinib (nM) | IDE196 (nM) |
| DMSO | DMSO |
| 13.72 | 0.64 |
| 41.15 | 3.20 |
| 123.46 | 16.00 |
| 370.37 | 80.00 |
| 1111.11 | 400.00 |
| 3333.33 | 2000.00 |
| 10000.00 | 10000.00 |

Pharmacodynamic Assessment

For all experiments, cells were seeded 24 h before treatment at 2.5×10^6 cells in 10 $cm^2$ tissue culture plates in 10% RPMI media. For IDE196-HGF combinations, cells were treated with the IDE196 and HGF combinations in 2% RPMI media for 2 hrs according to Table 3. For IDE196-MET inhibitor experiments, 24 h after seeding, the media was replaced with the appropriate inhibitor combinations in 2% RPMI media in the presence of 1.23-3.7 ng/ml HGF for 2 h, according to Table 4.

For all experiments, cells were washed with ice cold PBS and protein lysates were prepared by lysing cells in a RIPA buffer containing protease and phosphatase inhibitors. Protein samples (15 ug/well) were separated on 4-20% Bis-Tris SDS gels and electroblotted to nitrocellulose membranes using iBlot (Invitrogen). The membranes were incubated for 1b in Superblock buffer at RT, followed by overnight incubation with primary antibody at 4° C. The primary antibodies Phospho-Met (Tyr1234/1235) (3077S), cMET (3148S), Phospho-Akt (Ser473) (4060S), Akt (pan) (2920S), Phospho-MARCKS (Ser159/163) (11992S), MARCKS (5607S), PKCδ (9616S), Phospho-p44/42 MAPK (ERK1/2) (Thr202/Tyr204) (4377S), pRAS40 were obtained from Cell Signaling. Total ERK (ab184699) and PKC delta (phospho S299) (ab133456) antibodies were from Abcam. After three washes in PBST, the membrane was incubated with HRP-conjugated secondary antibody for 1 h at RT, washed thrice in PBST, and detected using enhanced chemiluminescence (Biorad Chemidoc XRS).

TABLE 3

| MEL-202 & MM28 | | 92.1 | |
|---|---|---|---|
| HGF (ng/ml) in DMSO | IDE 196 (Compound A) (nM) in DMSO | HGF (ng/ml) in DMSO | IDE 196 (Compound A) (nM) in DMSO |
| | 16 | | 16 |
| | 80 | | 80 |
| | 400 | | 400 |
| | 2000 | | 2000 |
| 1.23 | | 1.23 | |
| 3.7 | | 3.7 | |
| 11.11 | | 11.11 | |
| 33.33 | | 1.23 | 26 |
| 1.23 | 16 | 11.11 | 26 |
| 3.7 | 80 | 1.23 | 400 |
| 11.11 | 400 | 11.11 | 400 |
| 33.33 | 2000 | | |

TABLE 4

| MEL-202 | | | 92.1 | | | MM28 | | |
|---|---|---|---|---|---|---|---|---|
| HGF | crizotinib | IDE196 | HGF | crizotinib | IDE196 | HGF | crizotinib | IDE196 |
| – | DMSO | DMSO | – | DMSO | DMSO | + | DMSO | DMSO |
| + | DMSO | DMSO | + | DMSO | DMSO | + | 370 nM | |
| + | 123 nM | | + | 370 nM | | + | 1 uM | |
| + | 370 nM | | + | 1 uM | | + | 3 uM | |
| + | 1 uM | | + | 3 uM | | + | | 400 nM |
| + | | 16 nM | + | | 16 nM | + | | 2 uM |
| + | | 80 nM | + | | 80 nM | + | 370 nM | 80 nM |
| + | | 400 nM | + | | 400 nM | + | 1 uM | 400 nM |
| + | | 2 uM | + | | 2 uM | + | 3 uM | 2 uM |
| + | 123 nM | 16 nM | + | 123 nM | 16 nM | | | |
| + | 370 nM | 80 nM | + | 370 nM | 80 nM | | | |
| + | 1 uM | 400 nM | + | 1 uM | 400 nM | | | |

Example 3

Elevated cMET Presence in Uveal Melanoma Cells

Cells were seeded 24 h before treatment at 2.5×10^6 cells in 10 $cm^2$ tissue culture plates in 10% RPMI media. For all experiments, cells were washed with ice cold PBS and protein lysates were prepared by lysing cells in a RIPA buffer containing protease and phosphatase inhibitors. Protein samples (15 ug/well) were separated on 4-20% Bis-Tris SDS gels and electroblotted to nitrocellulose membranes using iBlot (Invitrogen). The membranes were incubated for 1b in Superblock buffer at RT, followed by overnight incubation with primary antibody at 4° C. The primary antibodies Phospho-Met (Tyr1234/1235) (3077S) and Met (3148S) were used. After three washes in PBST, the membrane was incubated with HRP-conjugated secondary antibody for 1 h at RT, washed thrice in PBST, and detected using enhanced chemiluminescence (Biorad Chemidoc XRS). Cell lines MM28 and MEL-202 produced high levels of cMET while cell line 92.1 produced a low level of cMET. These results are shown as Western Blot graphs, FIG. 4.

Example 4

RESULTS OF IDE196-cMET INHIBITOR COMBINATIONS

Cell preparations described above were cultured as described for assessment of cell viability in response to IDE 196-cMET inhibitor combination following HGF cell culture exposure.

Results for IDE196 Sensitivity Relative to Exogenous HGF Dosing

Figure 2A:
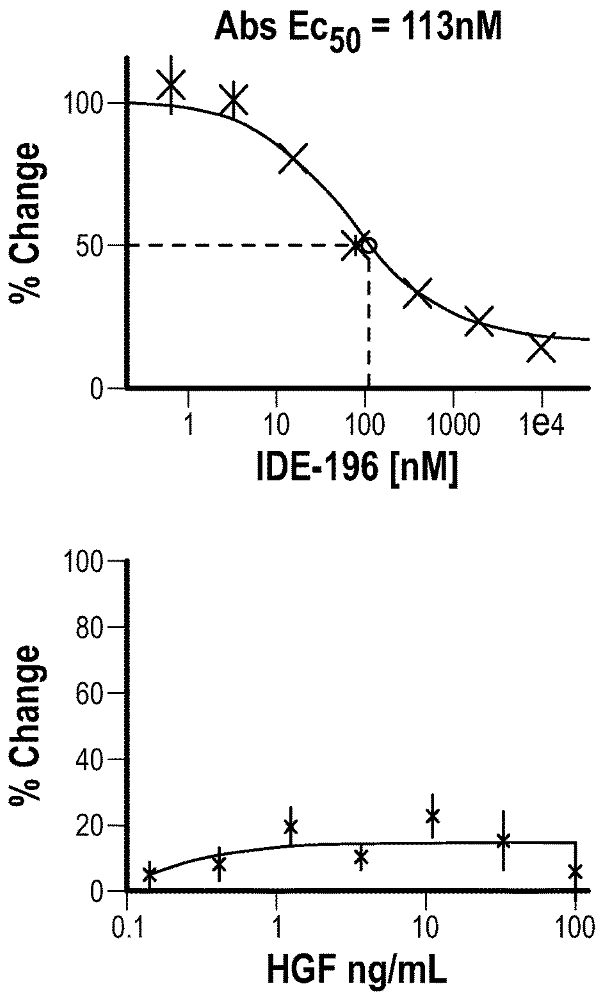
FIG. 2A provides charts illustrating the antagonistic effect of HGF on IDE 196 (Compound A) in 92.1 primary uveal melanoma cells.
Figure 2A:
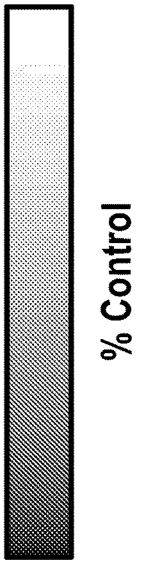
Figure 2A:
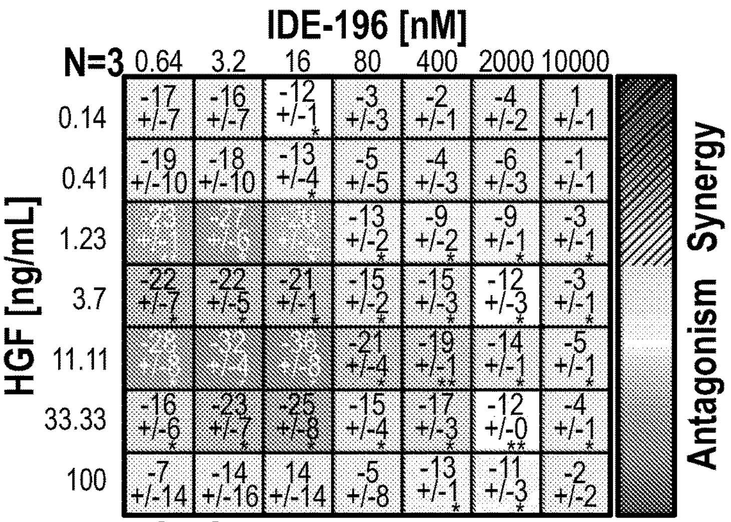
Figure 2A:
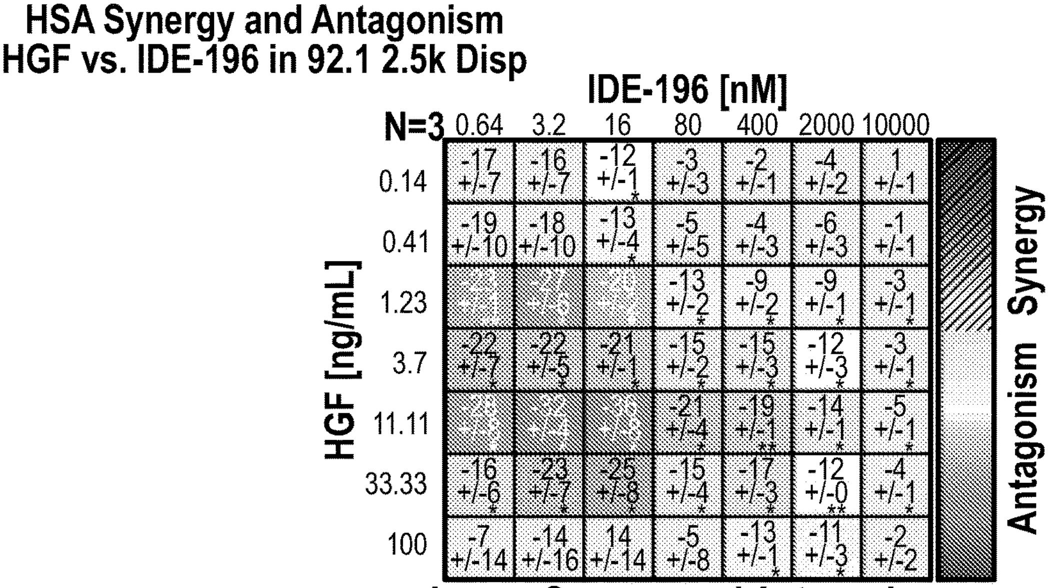
Figure 2A:
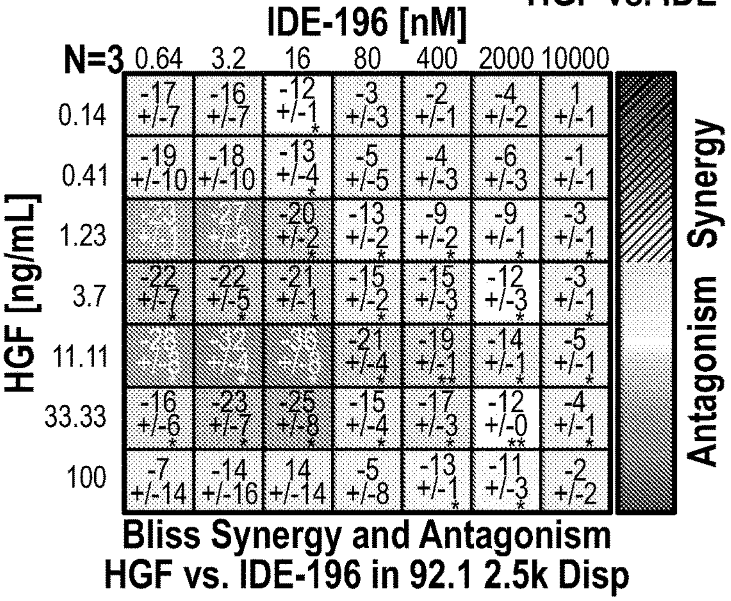
Figure 2A:
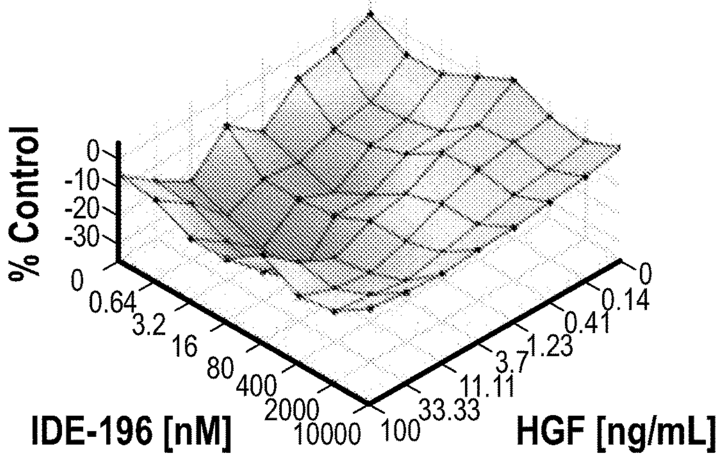
Figure 2A:
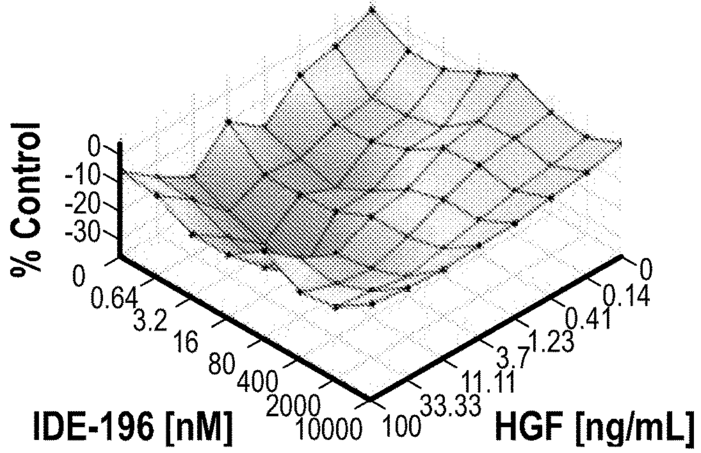
Figure 2A:
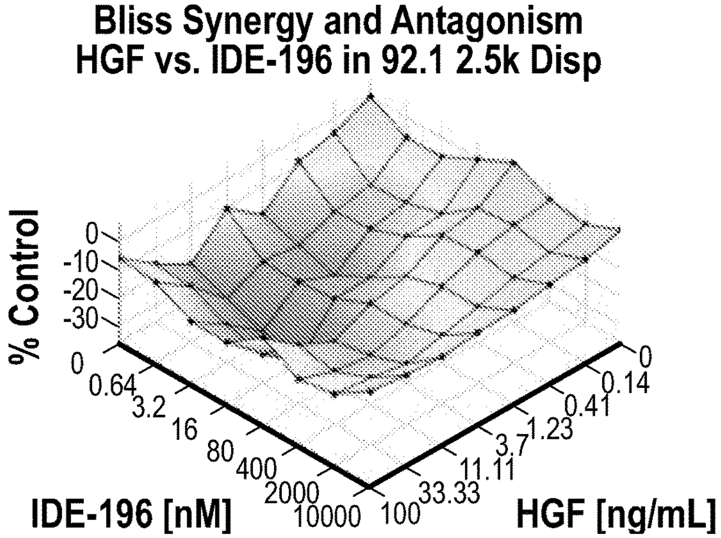
Figure 2A:
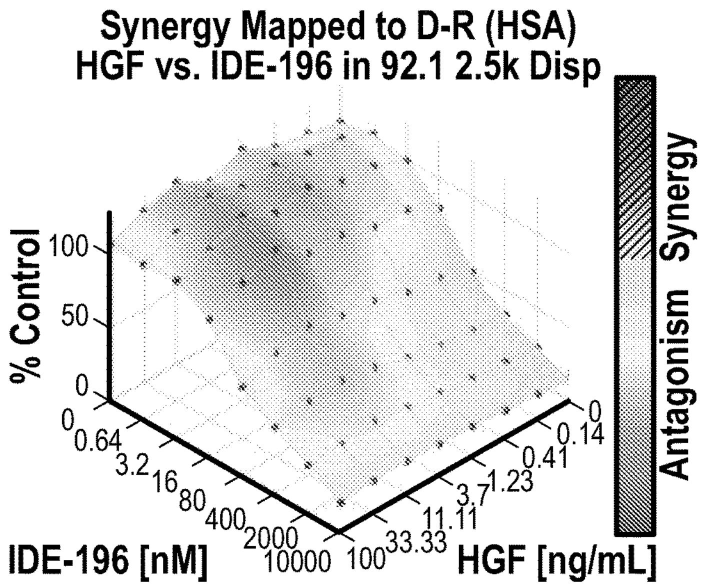
Figure 2A:
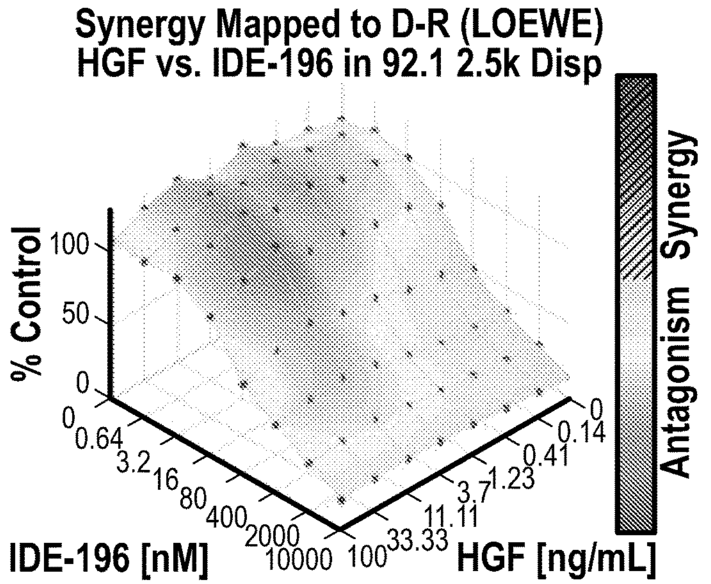
Figure 2A:
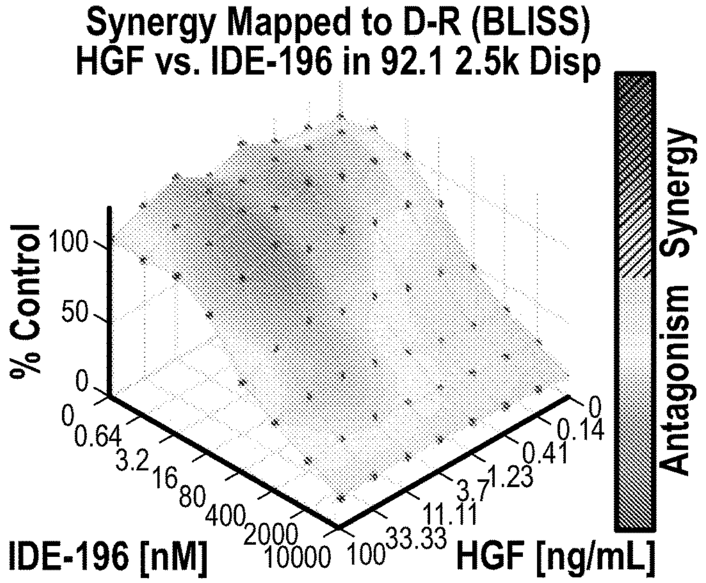
Figure 3A:
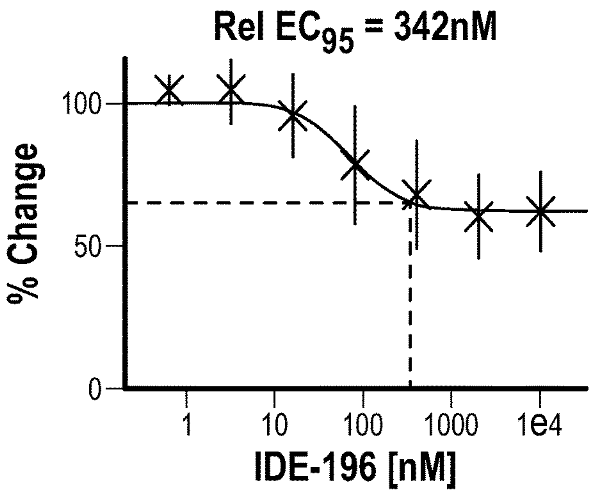
FIG. 3A provides charts illustrating the antagonistic effect of HGF on IDE 196 (Compound A) in MM28 metastatic uveal melanoma cells.
Figure 3A:
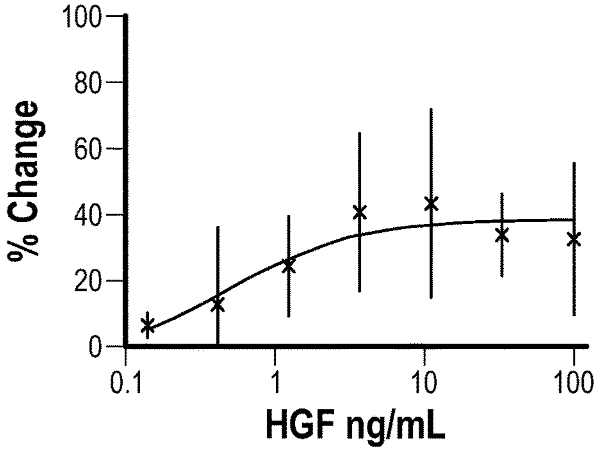
Figure 3A:
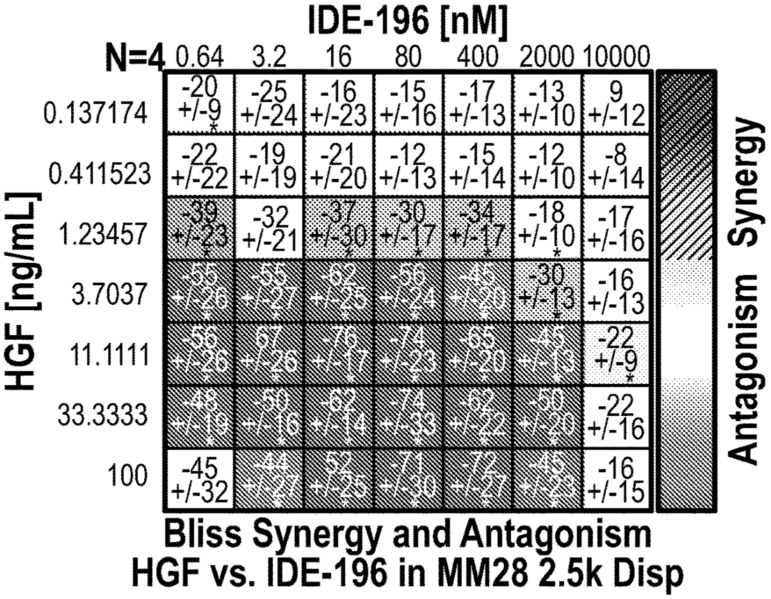
Figure 3A:
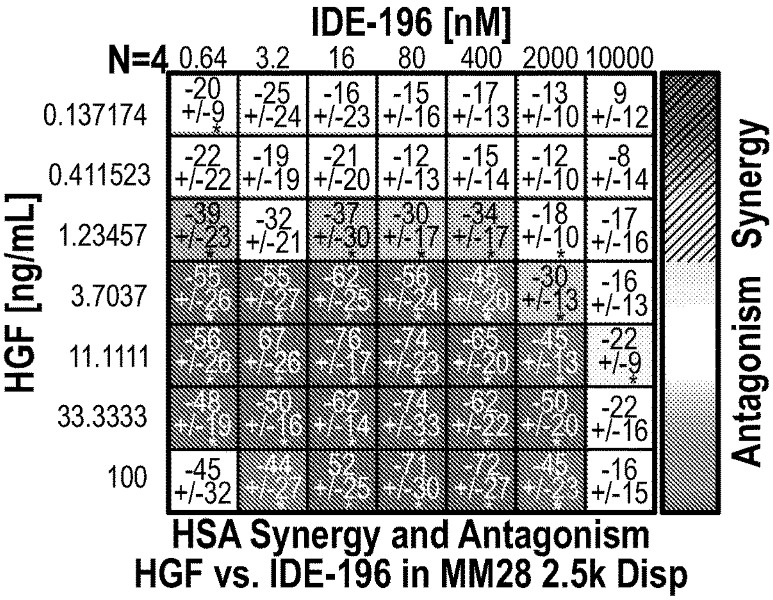
Figure 3A:
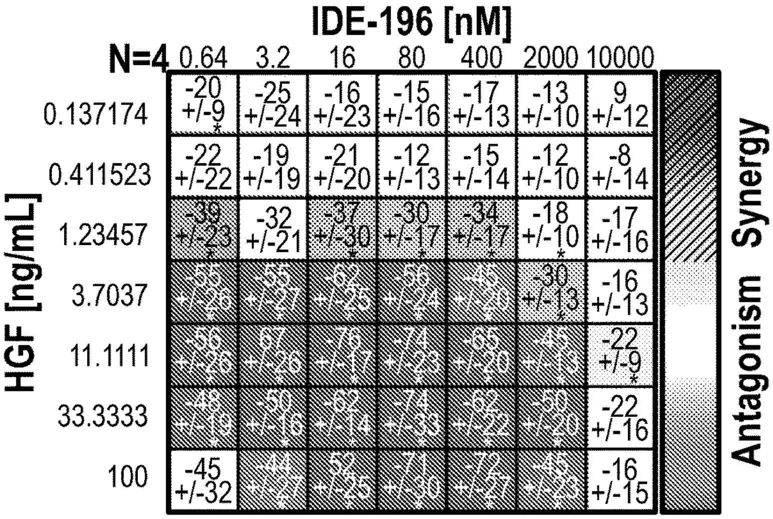
Figure 3A:
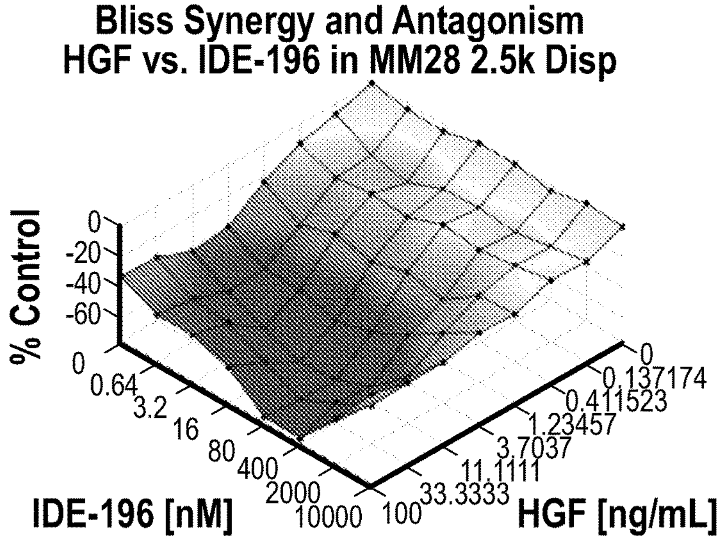
Figure 3A:
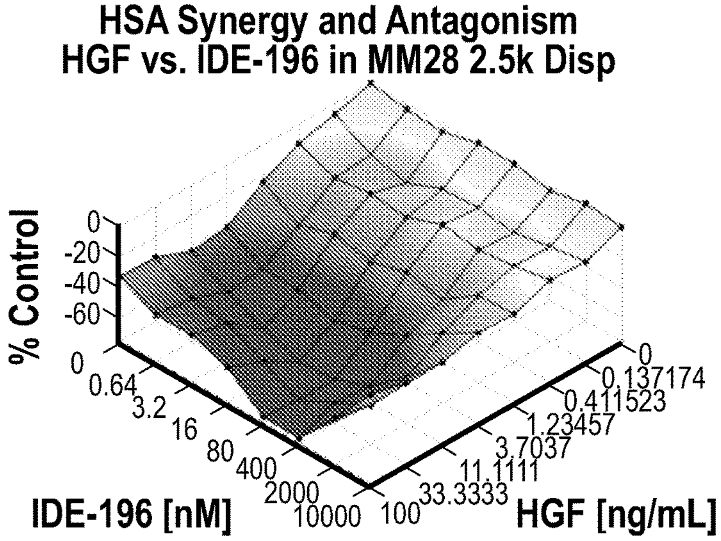
Figure 3A:
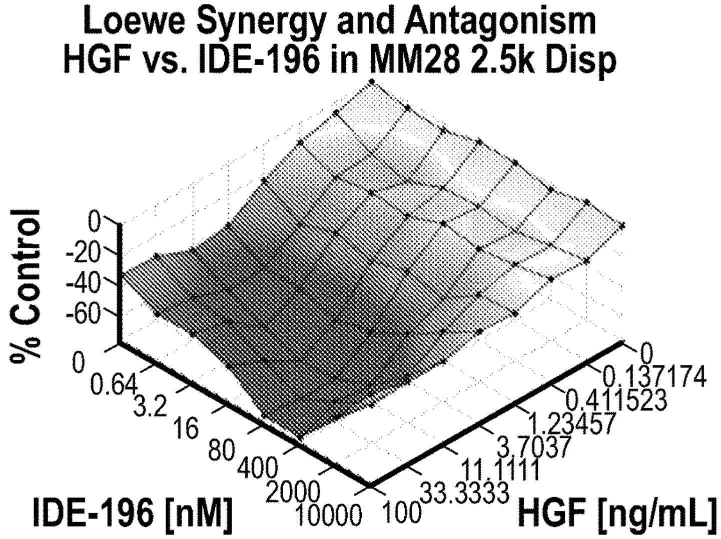
Figure 3A:
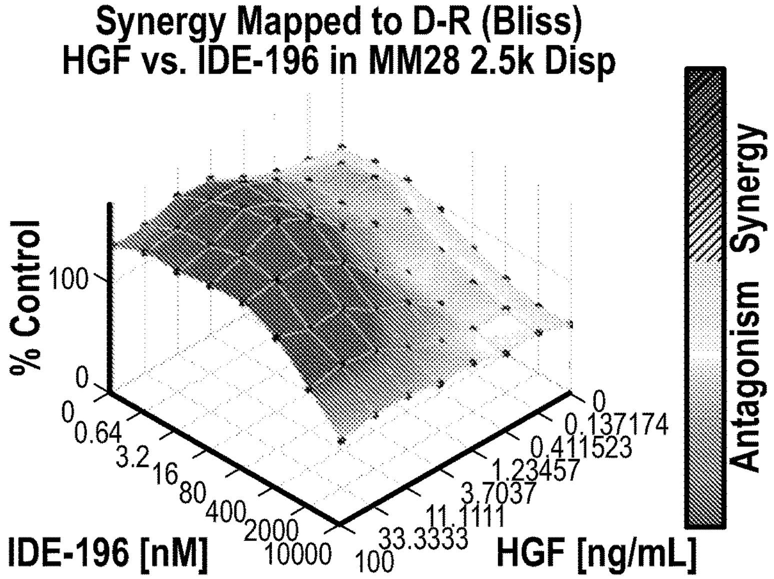
Figure 3A:
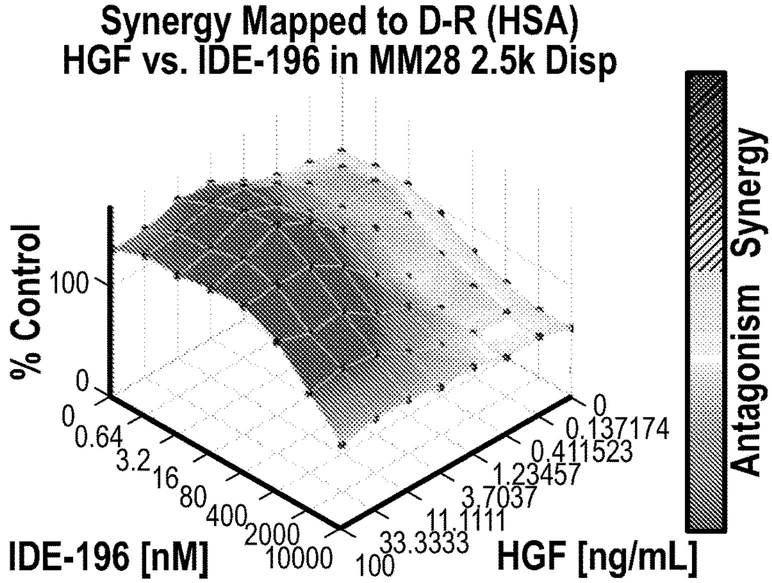
Figure 3A:
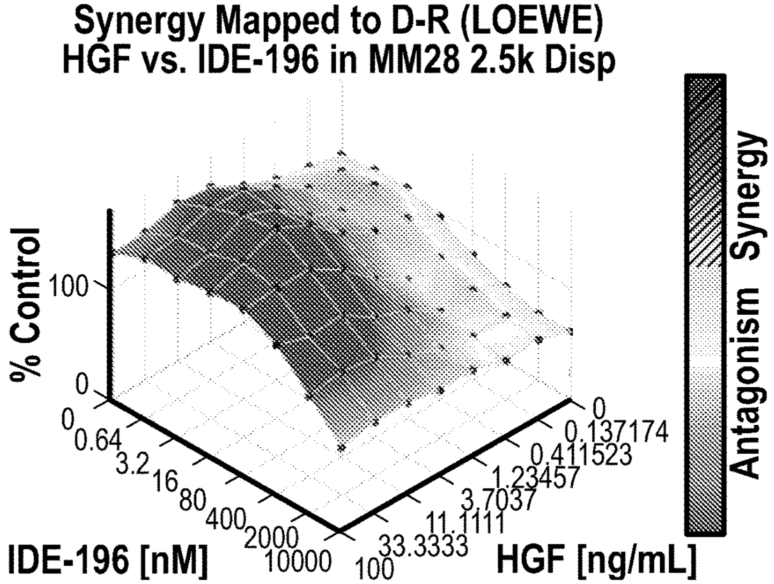
Figure 4:
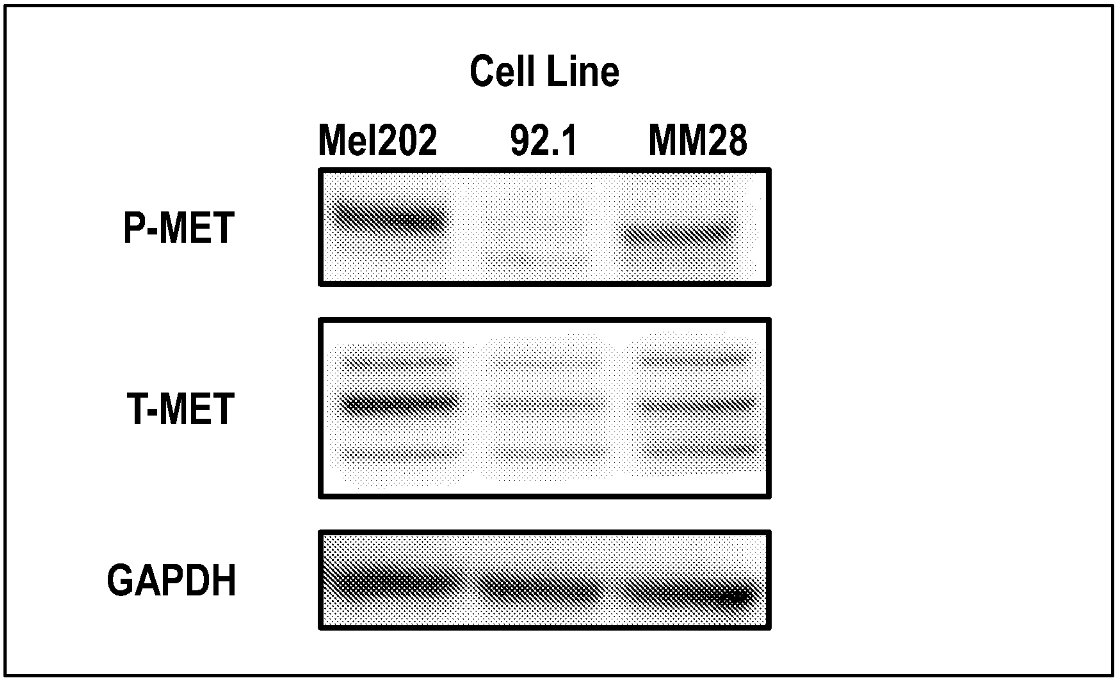
FIG. 4 provides a western blot comparing the relative presence of cMET in MEL-202, 92.1, and MM28 uveal melanoma cell lines. T-MET corresponds to total cMET concentration and P-MET corresponds to phosphorylated cMET concentration. GAPDH is a reference standard.

Cell viability: To evaluate IDE196 sensitivity in the presence of HGF, we assessed cell viability changes in MEL-202, 92.1 and MM28 cells, at different combinations of IDE196 and HGF. In MEL-202, 92.1 and MM28, there was a dose dependent inhibition of cell viability in response to IDE196 with an EC50=250 nM, 113 nM and 342 nM respectively (N=3, FIGS. 1A, 2A & 3A). Exposure of these cell lines to exogeneous HGF increased cell viability significantly in MEL-202 and MM28 cells but not in 92.1 cells. This is attributed to the higher expression of cMET in MEL-202 and MM28 cells, compared to 92.1 cells (FIG. 4). Combination results showed that there was high antagonism of IDE196 induced growth inhibition at concentrations at or above 3.7 ng/mL HGF across all concentrations of IDE196 in MEL-202 and MM28 cells (FIGS. 1A & 3A). In 92.1 cells, only modest antagonism was observed from 1.23 to 33.33 ng/ml of HGF (FIG. 2A). The results were consistent using HSA, Loewe and Bliss algorithms that were included in the combenefit analysis.

Figure 1B:
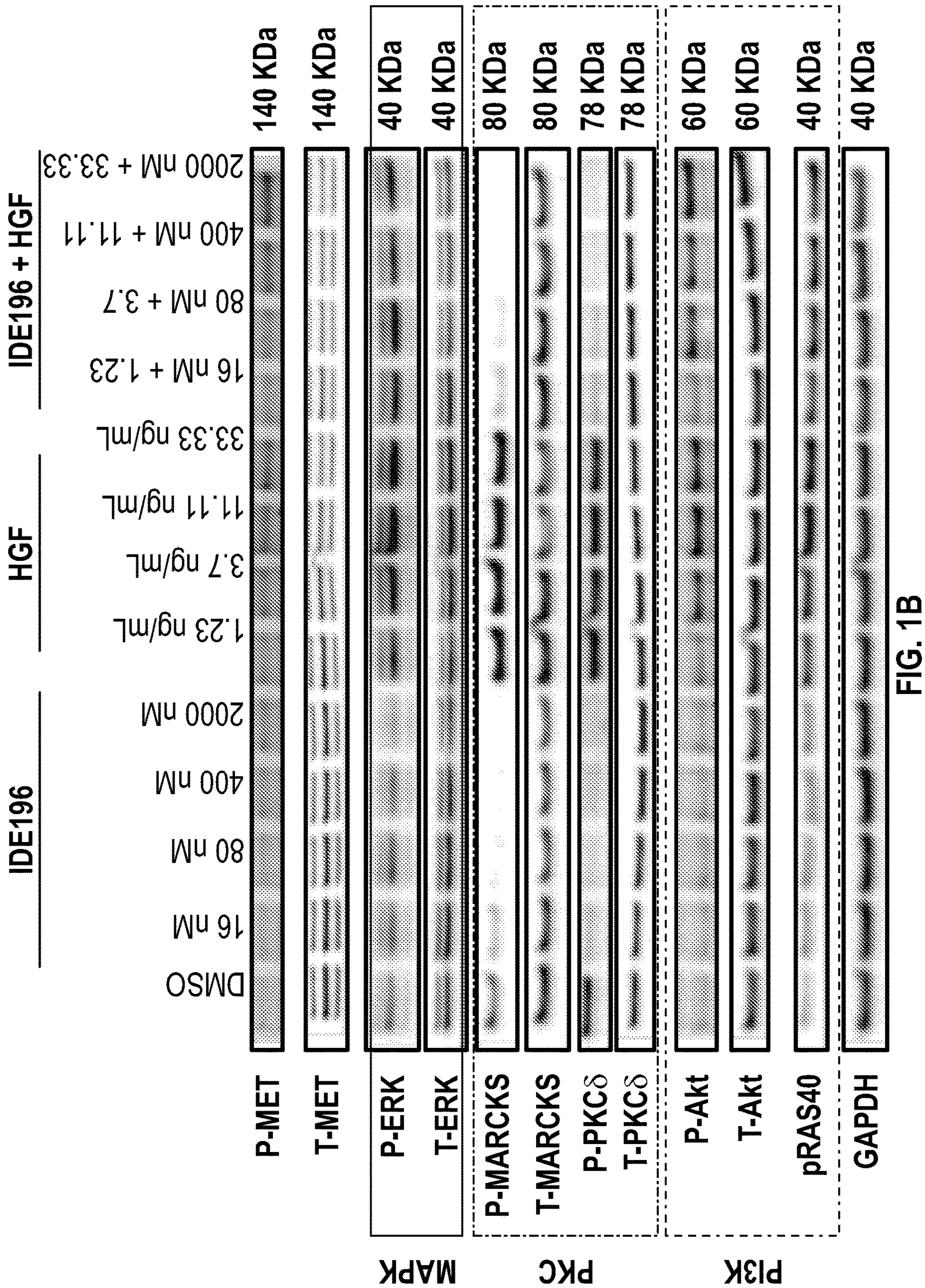
FIG. 1B provides western blots illustrating the pharmacodynamic effects of IDE 196 (Compound A) and HGF, separately and together, in MEL-202 primary uveal melanoma cell lines.
Figure 2B:
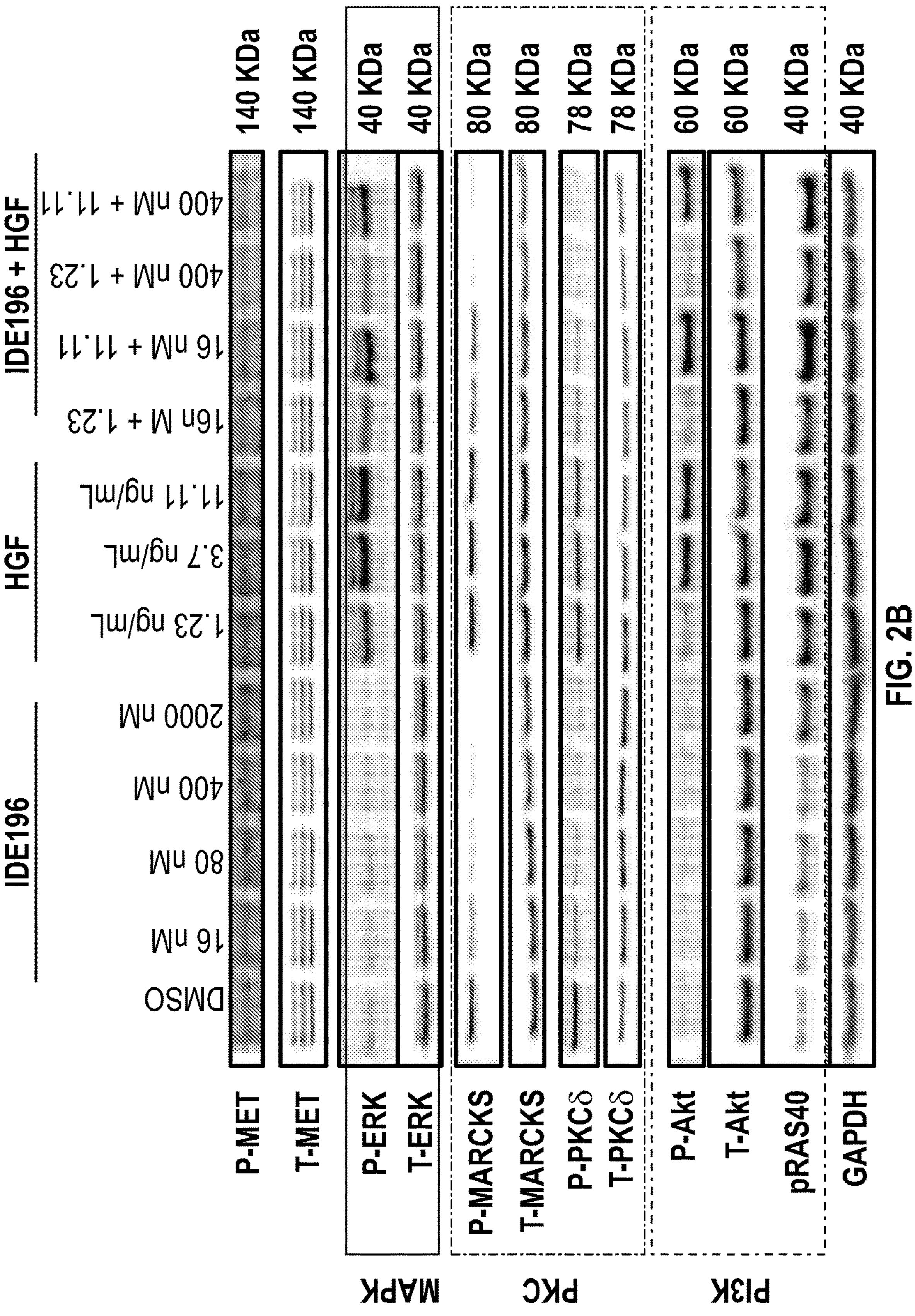
FIG. 2B provides western blots illustrating the pharmacodynamic effects of IDE 196 (Compound A) and HGF, separately and together, in 92.1 primary uveal melanoma cell lines.
Figure 3B:
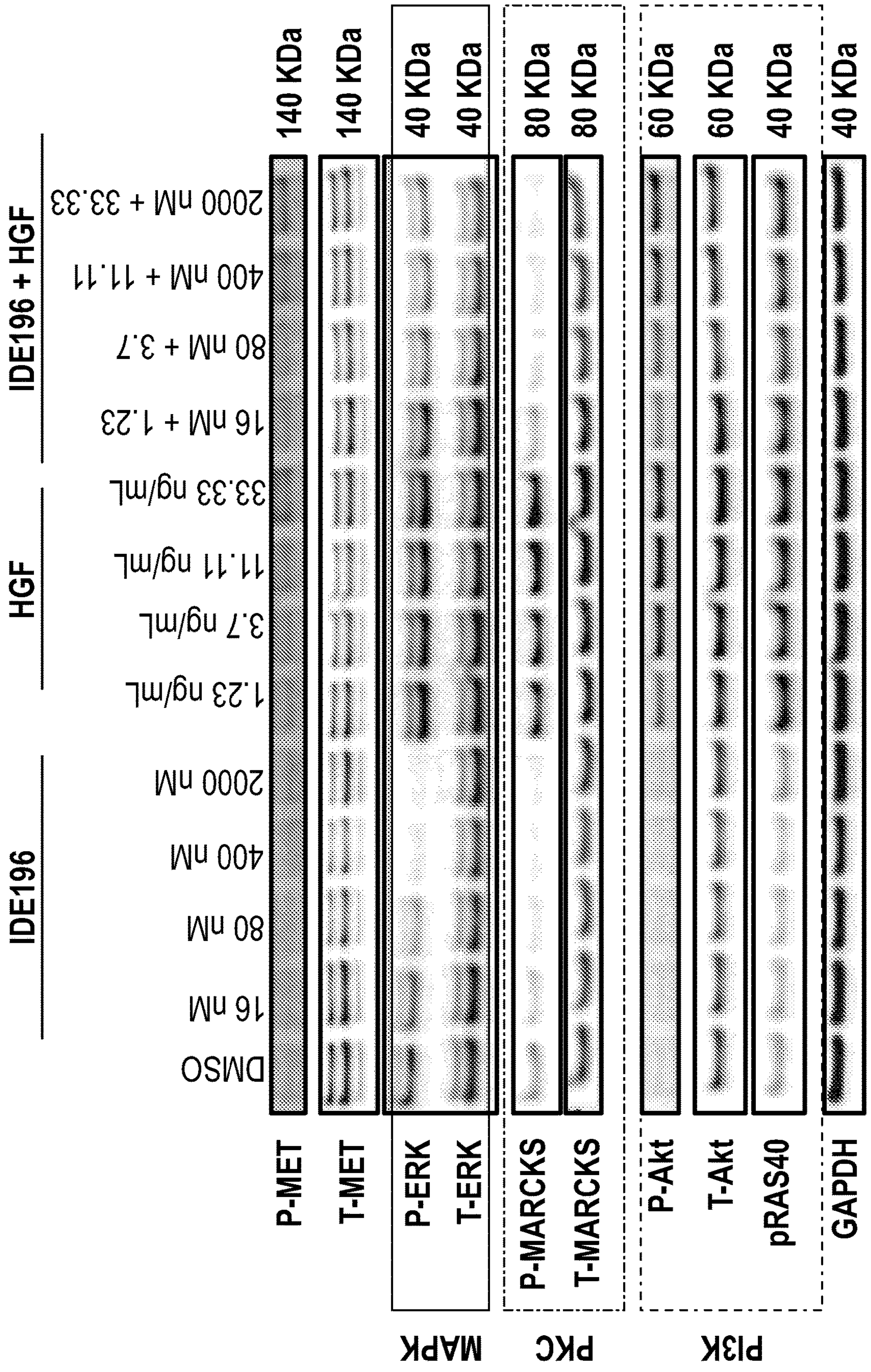
FIG. 3B provides western blots illustrating the pharmacodynamic effects of IDE 196 (Compound A) and HGF, separately and together, in MM28 metastatic uveal melanoma cell lines.

PD analysis: cMET was activated by high concentrations of HGF in all three cells lines and was not decreased by IDE196 in the presence of HGF (FIGS. 1B, 2B and 3B). A dose-dependent decrease in pMARCKS and pPKC-delta was observed after IDE196 treatment alone. The addition of HGF did not significantly change pMARCKS and pPKC-delta alone or in combination with IDE196. In the absence of HGF, pERK was inhibited by IDE196 only at doses above 400 nM in all three cell lines. The addition of HGF induced pERK (MAPK signaling) and pAKT and pPRAS40 (PI3K signaling) in a dose-dependent manner in all three lines and this was not inhibited by the addition of IDE196 in the combination treatments. These results demonstrate that HGF activates cMET and promotes MAPK and PI3K signaling in these cell lines and that this activation makes these cells less sensitive to IDE196.

As illustrated by FIGS. 1A and 1B, HGF strongly antagonizes the effect of IDE196 on the viability of MEL-202 uveal melanoma cells. FIG. 1A shows the cytotoxic effects of IDE196 and HGF individually and in combination on the cell viability of MEL-202 cells (N=3). FIG. 1B shows PD analysis showing the effects of drug and HGF treatment on analytes of cMET, MAPK, PI3K and PKC signaling pathways. These data show that cMET, experimentally induced by exogeneous HGF, activates cMET and the MAPK and P13K signaling pathways, and strongly antagonizes IDE 196 antiproliferation activity in MEL-202 cells.

As illustrated by FIGS. 2A and 2B, HGF modestly antagonizes the effect of IDE196 on the viability of 92.1 uveal melanoma cells. FIG. 2A shows the cytotoxic effects of IDE196 and HGF individually and in combination on the cell viability of 92.1 cells (N=3). FIG. 2B shows a PD analysis showing the effects of drug and HGF treatment on analytes of cMET, MAPK, PI3K and PKC signaling pathways. These data show that exogenous HGF does not activate cMET and MAPK and PI3K signaling pathways and only modestly antagonizes IDE 196 antiproliferation activity in 92.1 uveal melanoma cells. The more modest antagonism observed in this cell line is attributed to the relatively lower expression of cMET in the 92.1 cell line compared to MEL-202 and MM28 cell lines (FIG. 4).

As illustrated by FIGS. 3A and 3B, HGF strongly antagonizes the effect of IDE196 on the viability of MM28 uveal melanoma cells. FIG. 3A shows the cytotoxic effects of IDE196 and HGF individually and in combination on the cell viability of MM28 cells (N=3). FIG. 3B shows PD analysis showing the effects of drug and HGF treatment on analytes of cMET, MAPK, PI3K and PKC signaling pathways. These data show that cMET, experimentally induced by exogenous HGF, activates cMET, MAPK and PI3K signaling pathways, and strongly antagonizes IDE196 antiproliferation activity in MM28 cells.

As illustrated by FIG. 4, the total and phospho-MET expression in Uveal melanoma cell lines is shown on the Western Blots. The faint lines for P-MET and T-MET for cell line 92.1 shows that cell line 92.1 has a much lower expression of cMET relative to the other cell lines. Elevated cMET presence is shown in MEL-202 and MM28 cells relative to 92.1 cells. These MEL-202 and MM28 cell lines having elevated cMET presence correlate to the data in Example 1 exhibiting an observed greater antagonistic effect on IDE 196 (Compound A) in the presence of HGF. The MEL-202 and MM28 cells show both increased total cMET concentration (T-MET). Because p-MET or activated cMET is correlated with total cMET concentration, determination of total cMET provides an assessment of the degree of elevated cMET presence that is involved with the PKC pathway.

In summary, these synergy/antagonism models show that MEL-202 and MM28 cells exhibit an unexpectedly greater antagonistic effect on IDE 196 (Compound A) in comparison to 92.1 cells-even when treated at the same concentration of HGF. Further, this greater antagonistic effect persists in MEL-202 and MM28 cells and maintains their viability, even at elevated dosages of IDE 196 (Compound A). Thus, the results show that HGF activates cMET, MAPK and PI3K signaling which is not inhibited by IDE 196 (Compound A) in MM28 or MEL-202 cells. MAPK lies downstream of both PKC and cMET. Thus, cMET counteracts the effect of IDE 196 (Compound A) on MAPK signaling. Both MM28 and MEL-202 cells show similar signaling profiles in response to IDE 196 (Compound A), and HGF, despite differing cell viability profiles in response to the same agents.

In particular, HGF exhibited a relatively flat dose response curve in 92.1 cells compared to MEL-202 and MM28 cells. The response of IDE 196 (Compound A) on viability of 92.1 cells was relatively flat across HGF titrations; whereas in MEL-202 and MM28 cells, the greater antagonistic of HGF rose sharply at HGF concentrations that can be physiologically relevant for certain tumors. These results show that Compound A can provide a strong anti-proliferative effect even in the presence of HGF in 92.1 cells, with or without dose shifting. Yet, for MEL-202 and MM28, these results show that the strongly antagonistic effect of cMET stimulated by HGF cannot be meaningfully overcome by dose shifting to higher dosages of PKC inhibitor, particularly at higher concentrations of HGF.

Physiological concentrations of HGF in the liver can range from 0.3 ng/ml (normal liver) to 1-16 ng/ml, or higher, in liver diseases. Moreover, certain uveal melanoma cells may mutate to secrete HGF. As such, the stimulatory effect HGF represents a relevant effect in tumors that have metastasized to HGF rich tissues, particularly the liver, and also a relevant effect in other tumors, such as those that can secrete HGF. Moreover, the differing antagonistic effect on IDE 196 (Compound A) in different cell lines indicates a need for different therapeutic approaches depending on the relative presence of cMET, which may vary by the kind of tumor cells being treated.

The IDE196 (Compound A)—cMET Inhibitor Combination

Figure 5A:
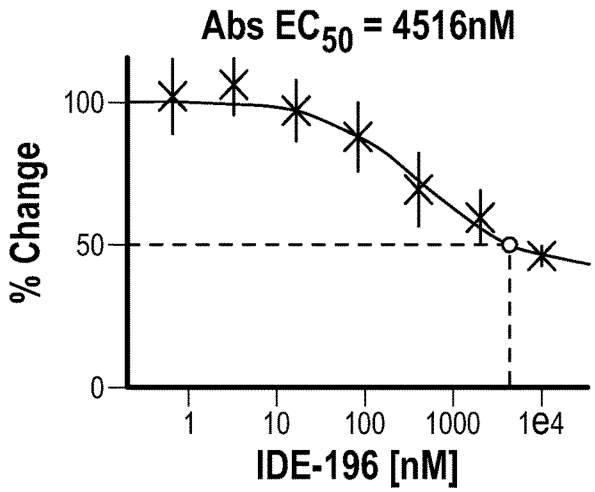
FIG. 5A provides charts illustrating the effect of a PKC inhibitor, e.g., IDE 196 (Compound A) and a cMET inhibitor (crizotinib, which is also abbreviated in the figures as "crizo") on the viability of MEL-202 primary uveal melanoma cells in the presence of HGF.
Figure 5A:
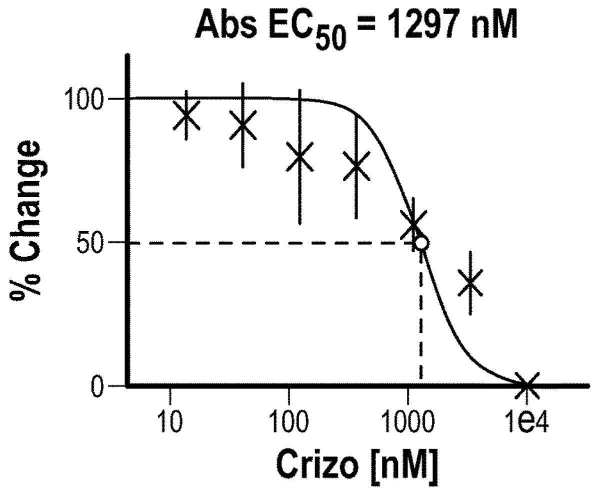
Figure 5A:
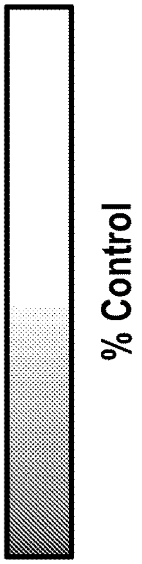
Figure 5A:
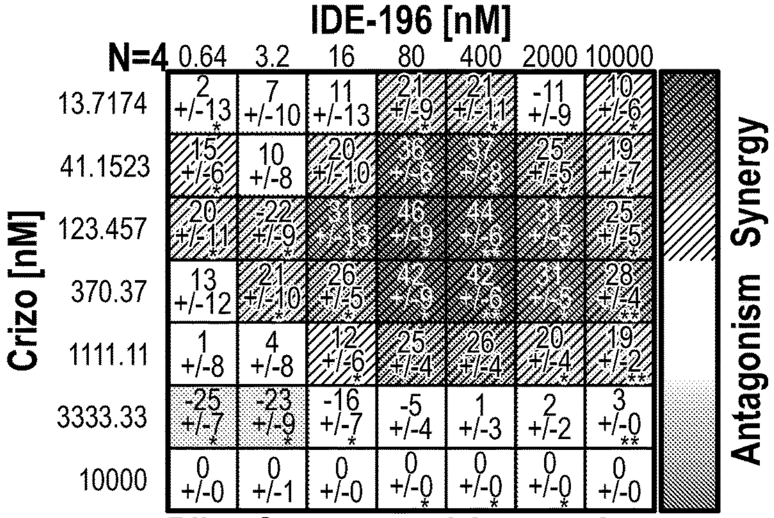
Figure 5A:
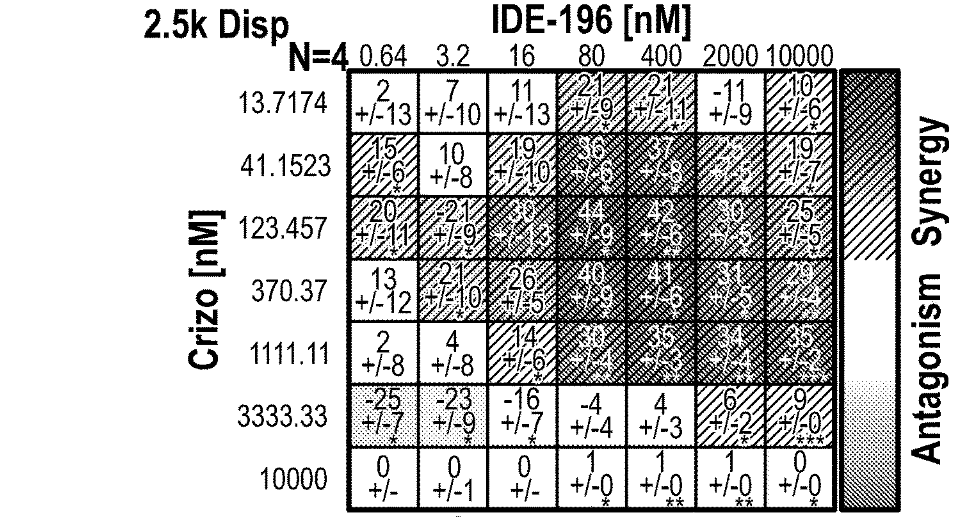
Figure 5A:
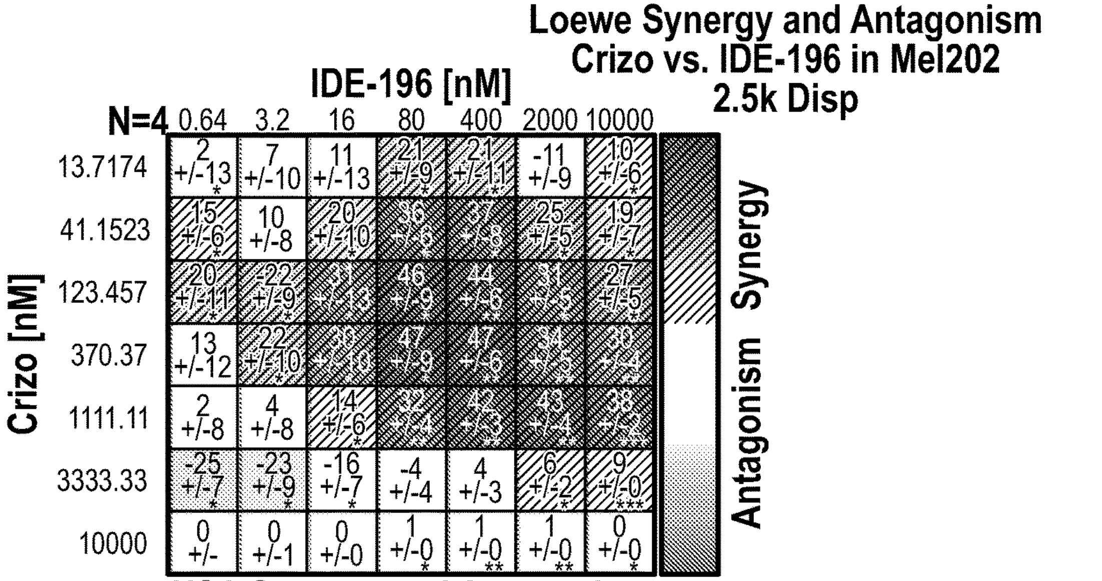
Figure 5A:
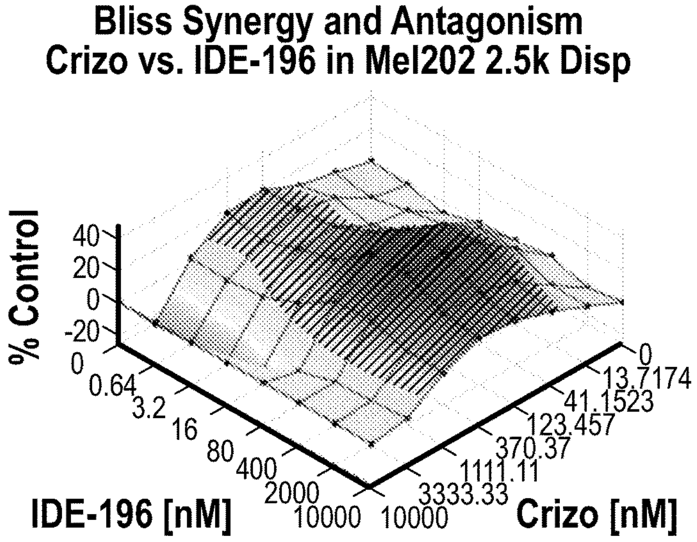
Figure 5A:
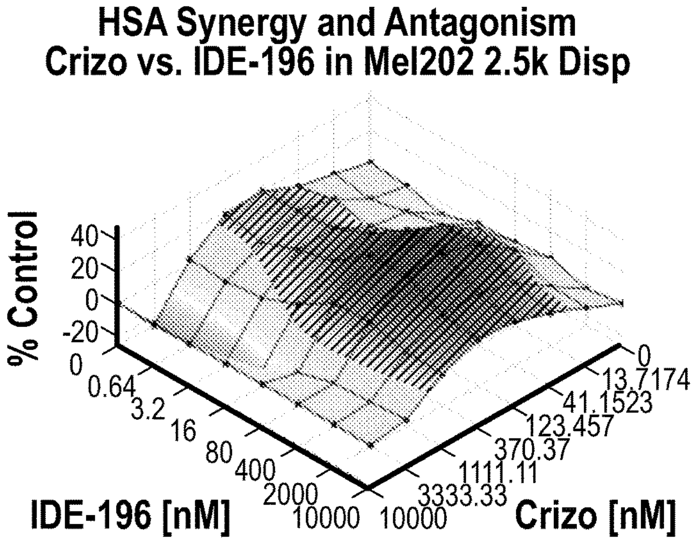
Figure 5A:
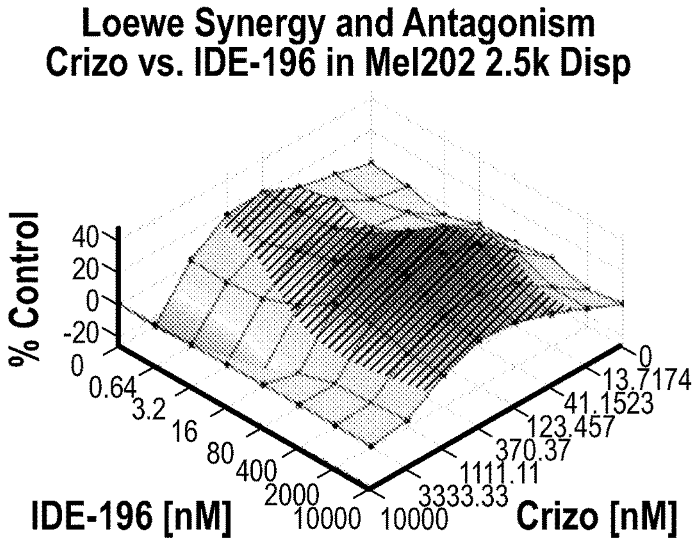
Figure 5A:
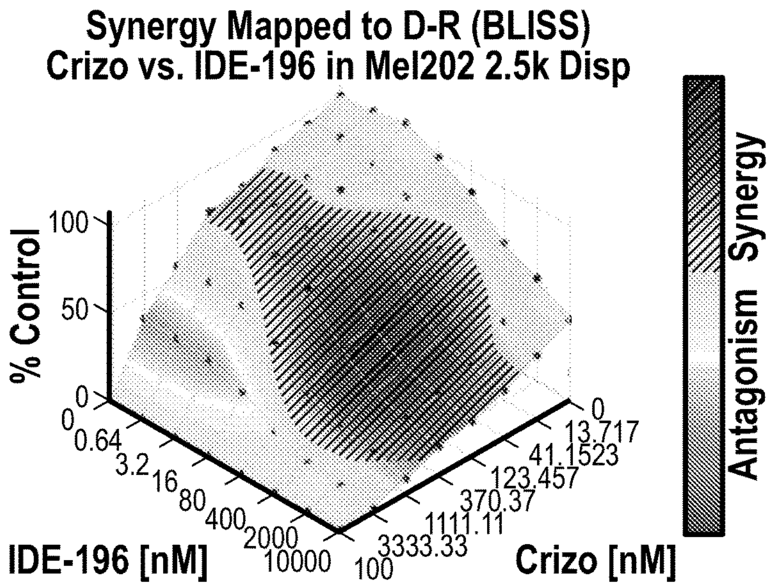
Figure 5A:
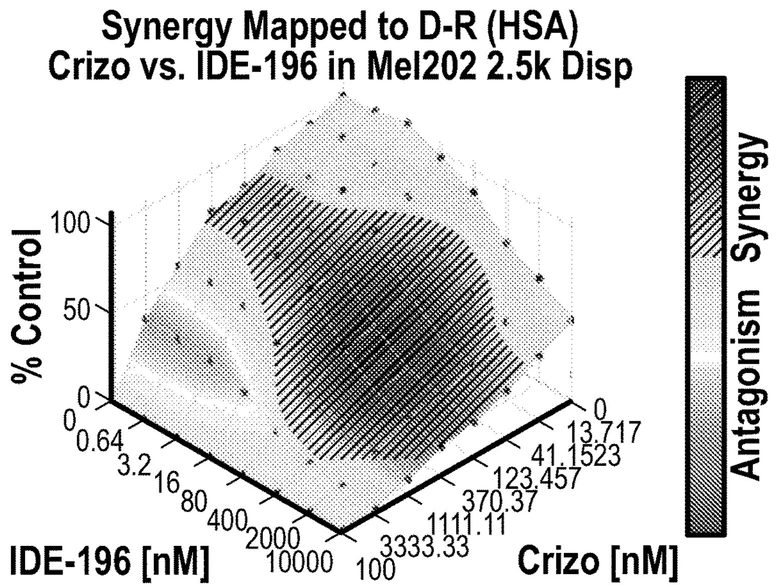
Figure 5A:
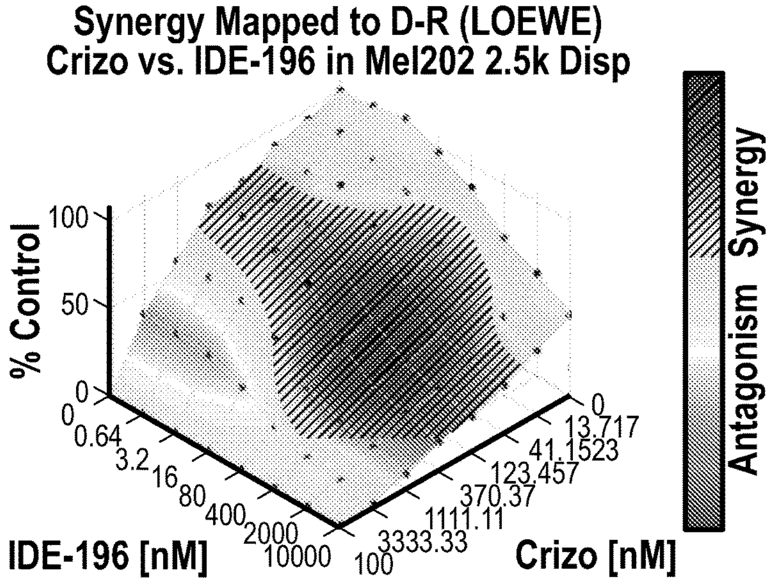
Figure 5B:
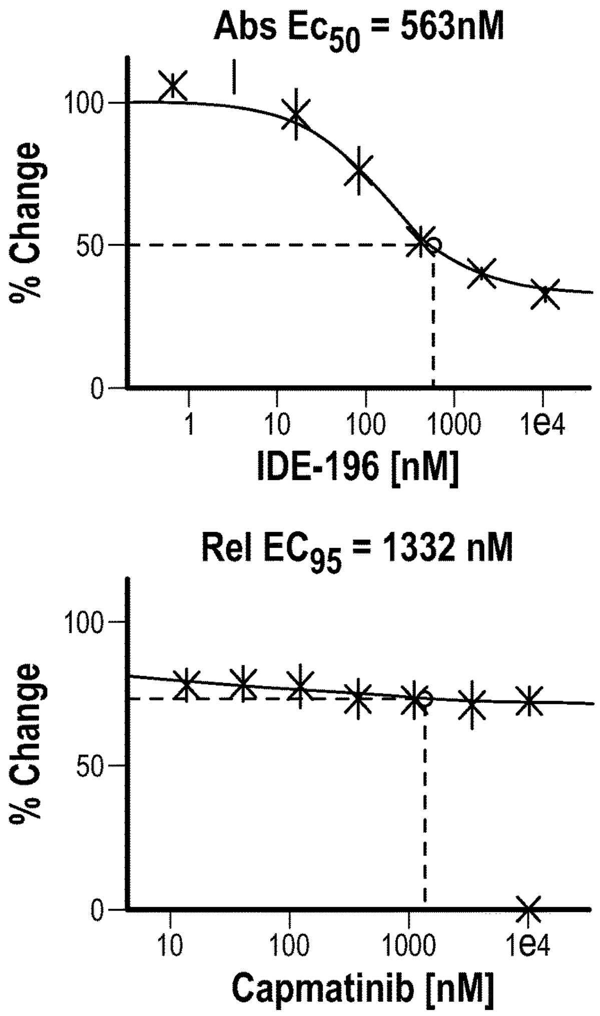
FIG. 5B provides charts illustrating the effect of a PKC inhibitor, e.g., IDE 196 (Compound A) and a cMET inhibitor (capmatinib, which is also abbreviated in the figures as "cap") on the viability of MEL-202 primary uveal melanoma cells in the presence of HGF.
Figure 5B:
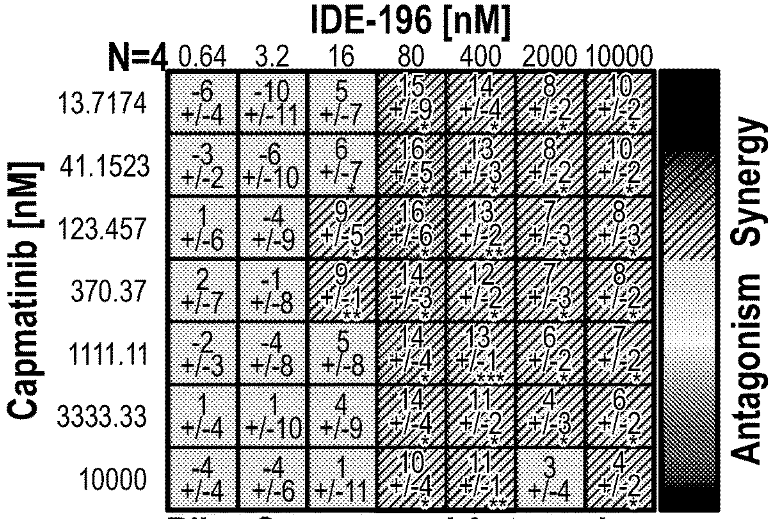
Figure 5B:
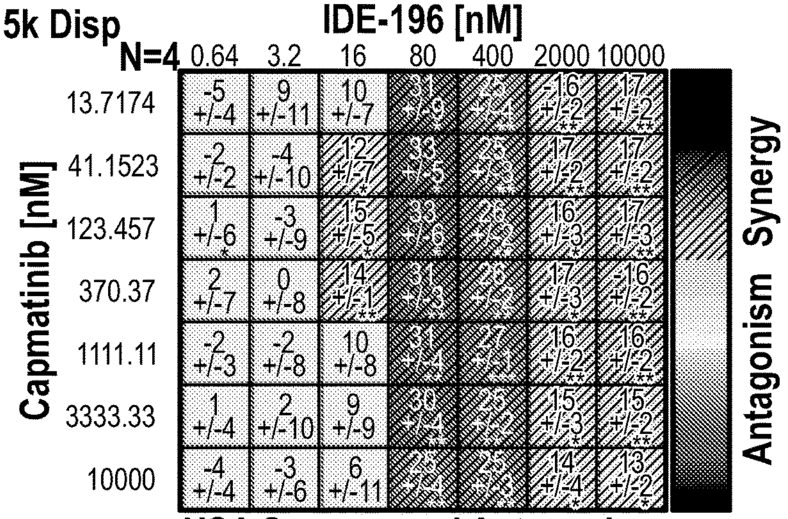
Figure 5B:
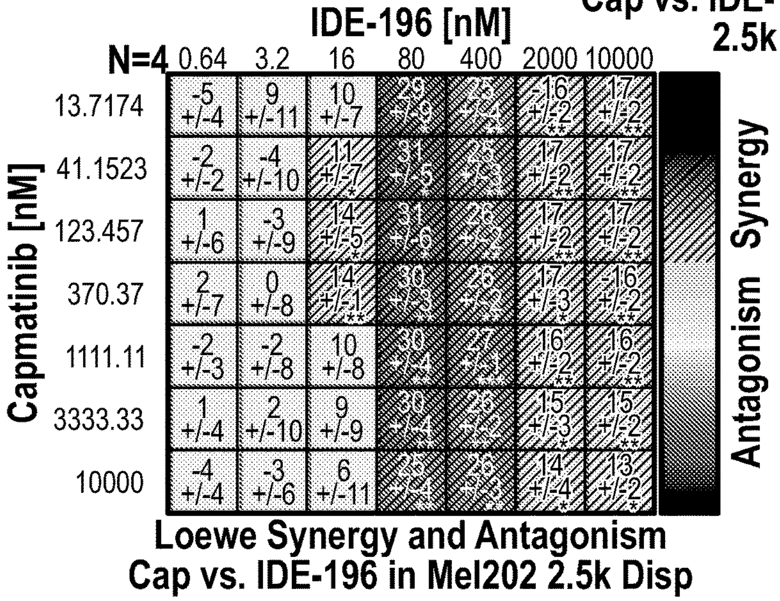
Figure 5B:
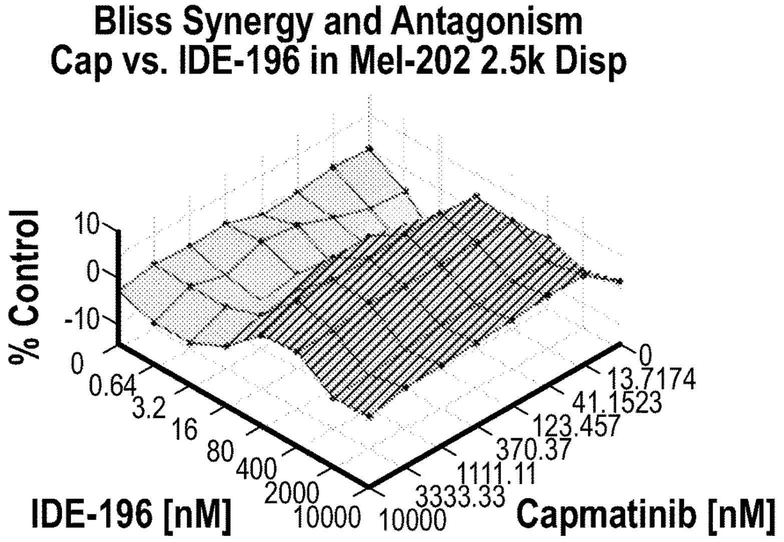
Figure 5B:
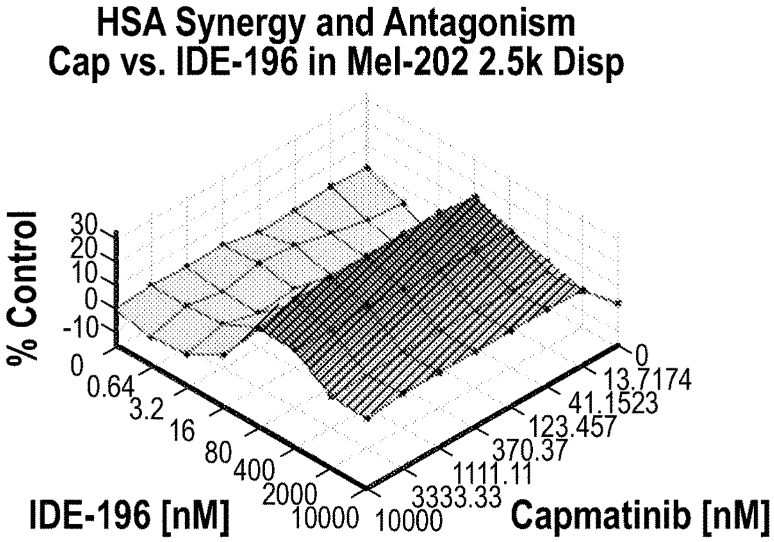
Figure 5B:
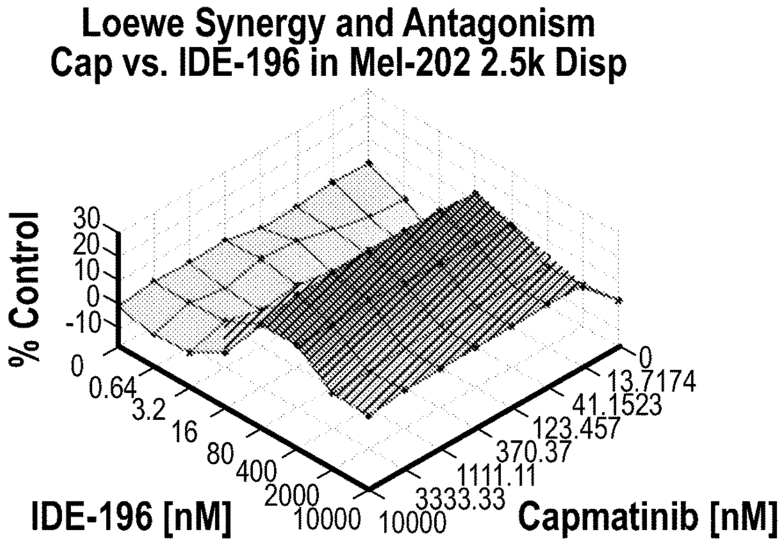
Figure 5B:
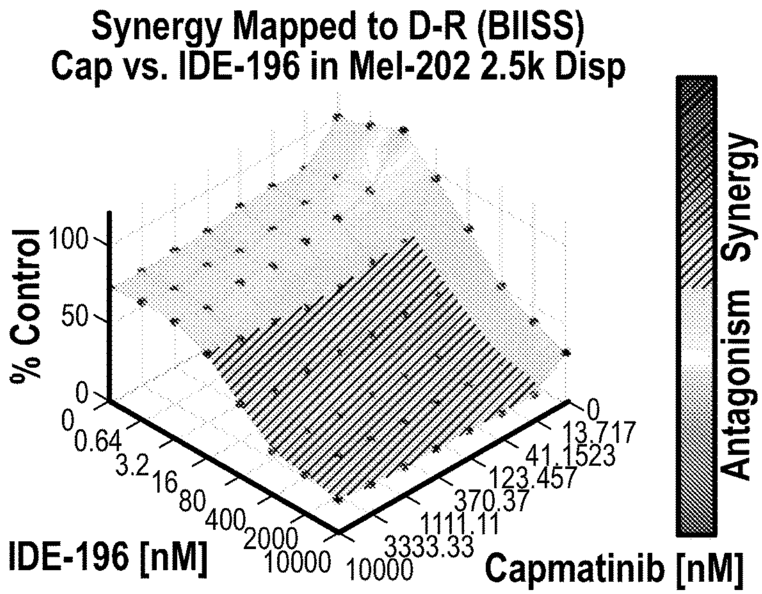
Figure 5B:
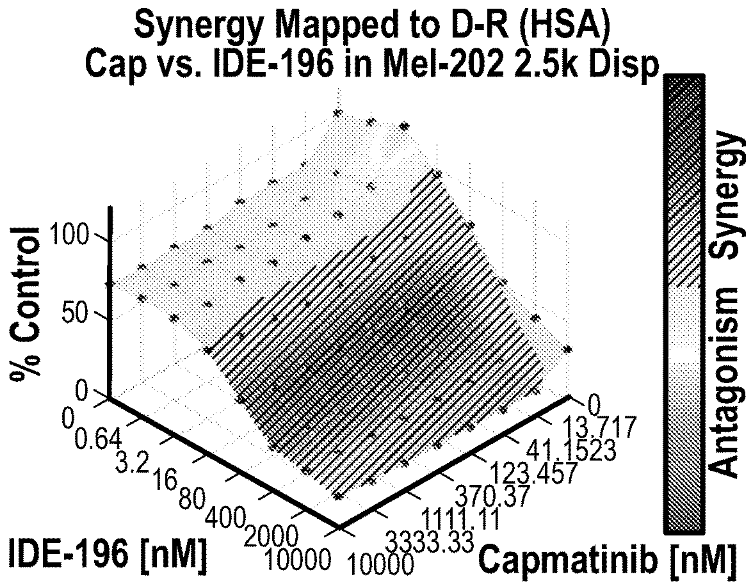
Figure 5B:
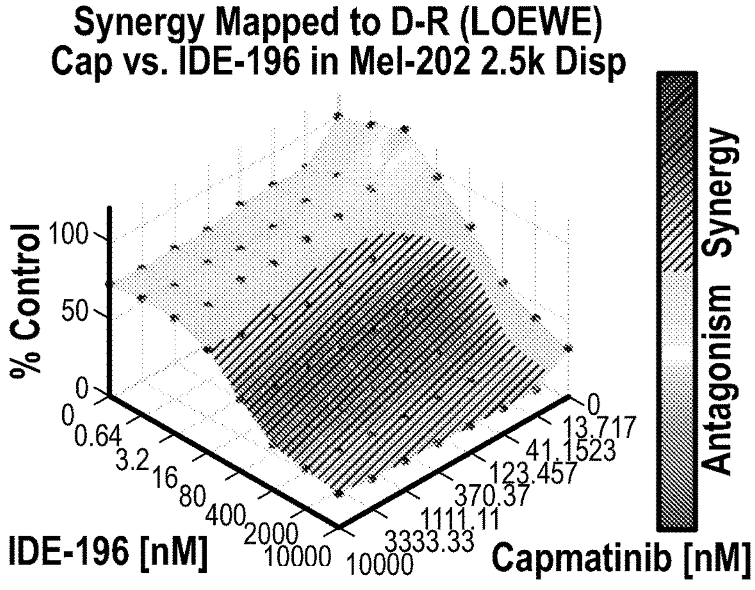
Figure 6A:
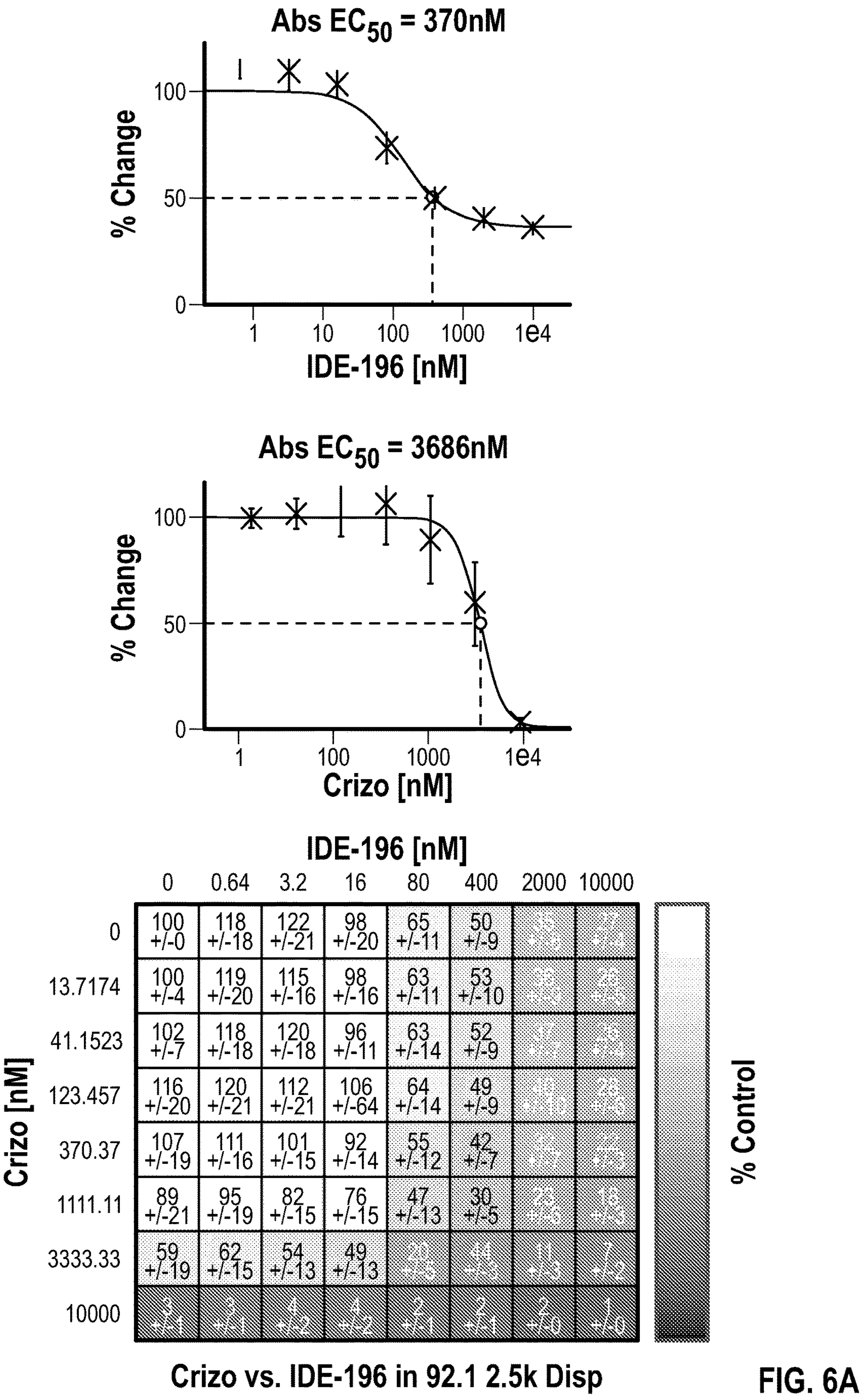
FIG. 6A provides charts illustrating the effect of a PKC inhibitor, e.g., IDE 196 (Compound A) and a cMET inhibitor (crizotinib) on the viability of 92.1 primary uveal melanoma cells in the presence of HGF.
Figure 6A:
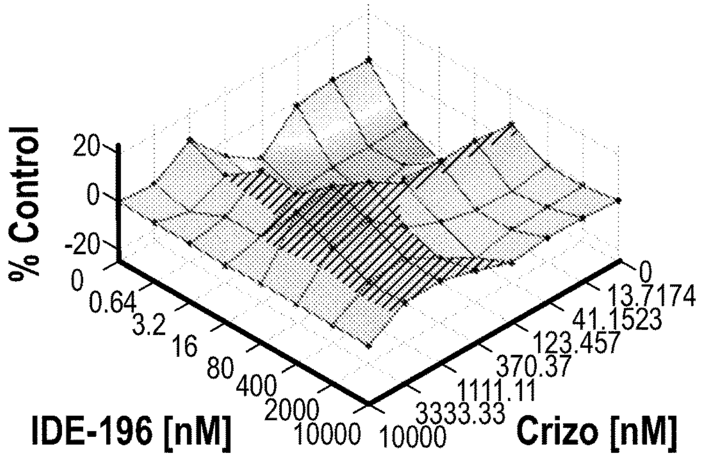
Figure 6A:
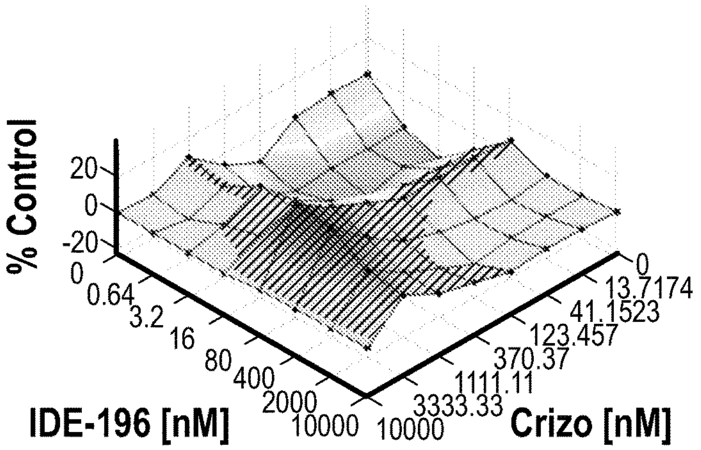
Figure 6A:
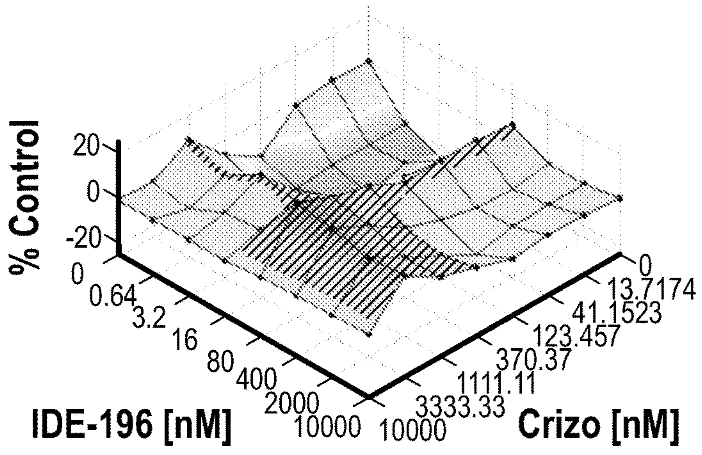
Figure 6A:
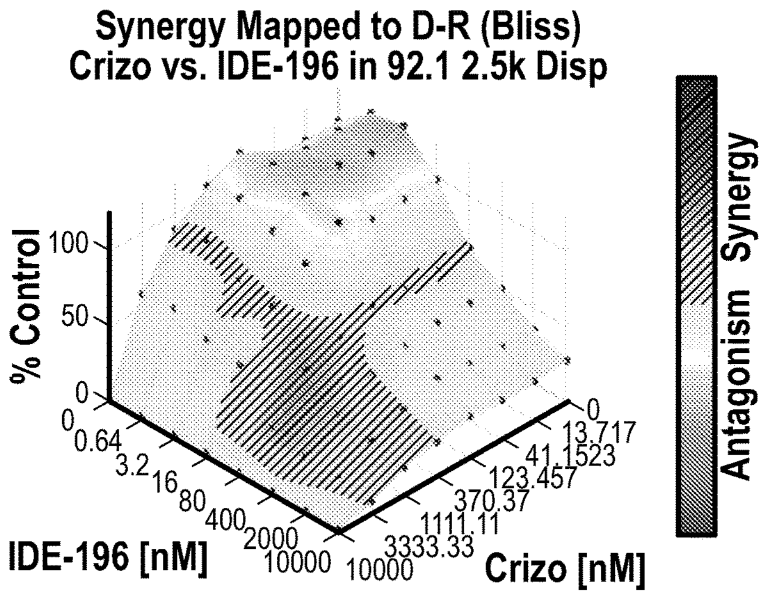
Figure 6A:
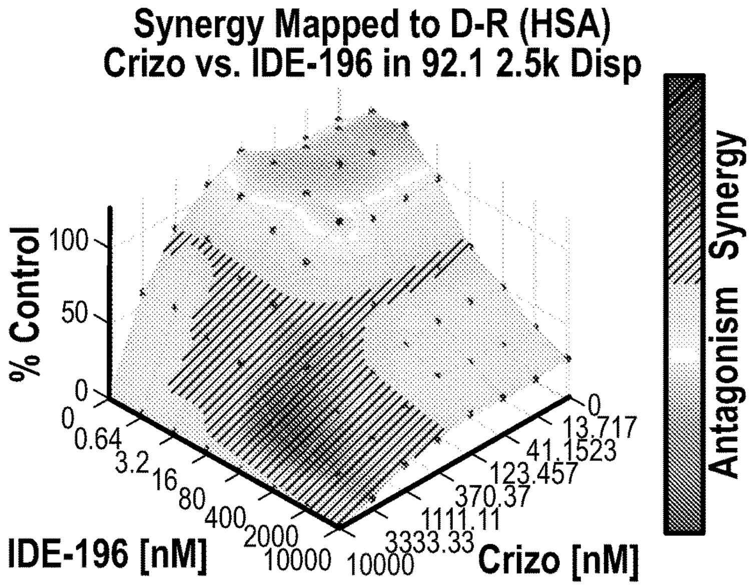
Figure 6A:
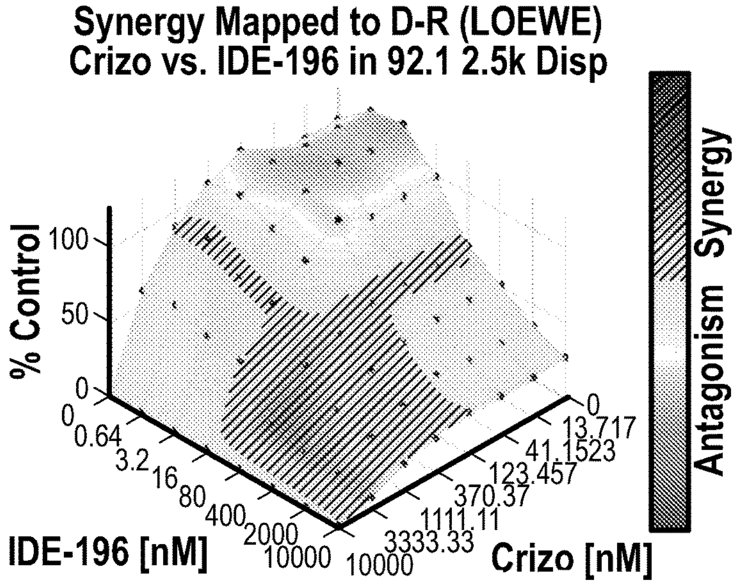
Figure 6B:
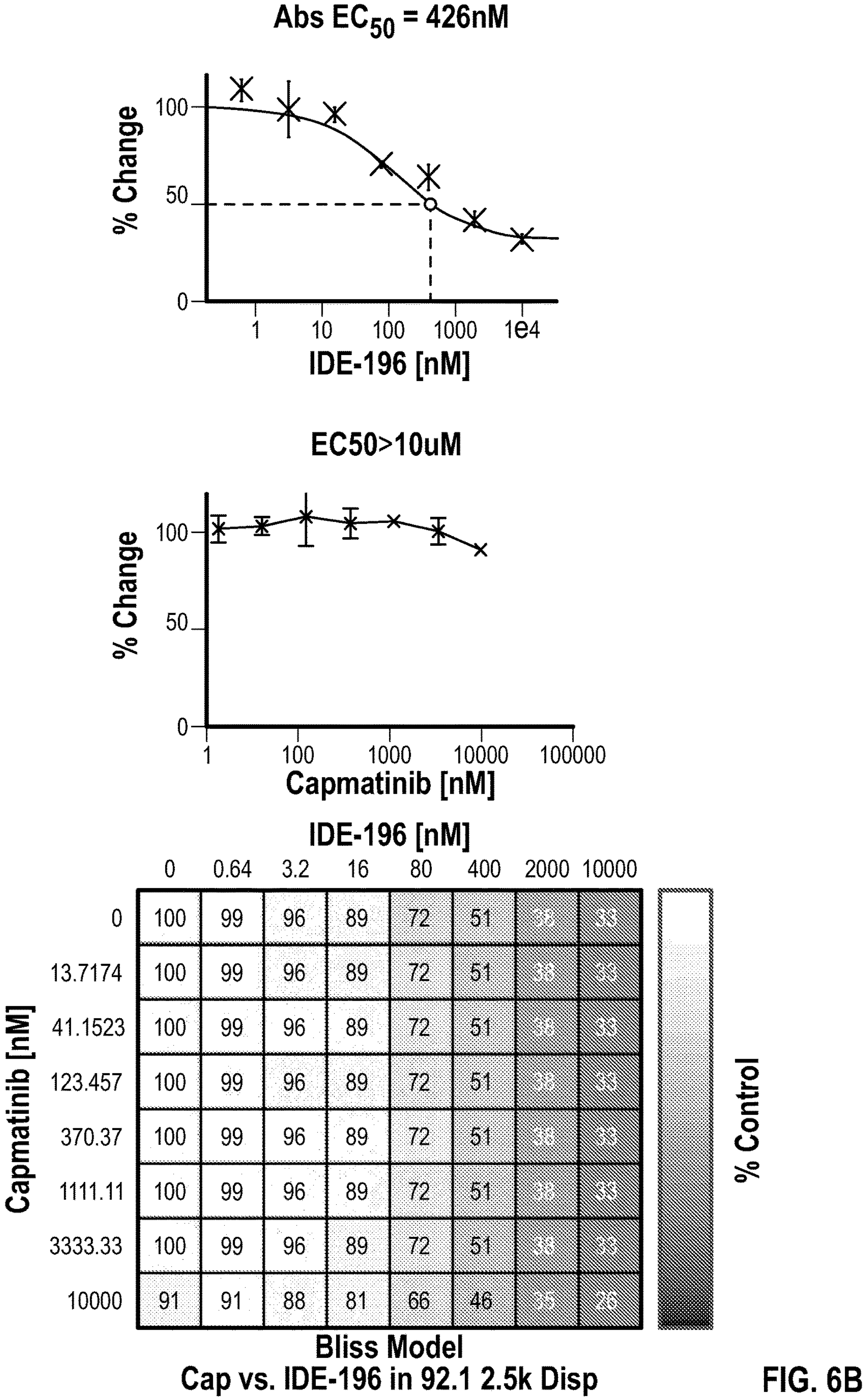
FIG. 6B provides charts illustrating the effect of a PKC inhibitor, e.g., IDE 196 (Compound A) and a cMET inhibitor (capmatinib) on the viability of 92.1 primary uveal melanoma cells in the presence of HGF.
Figure 6B:
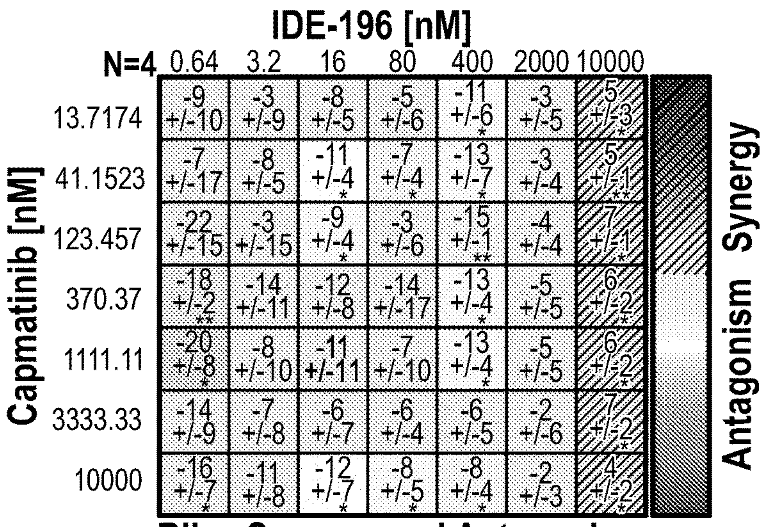
Figure 6B:
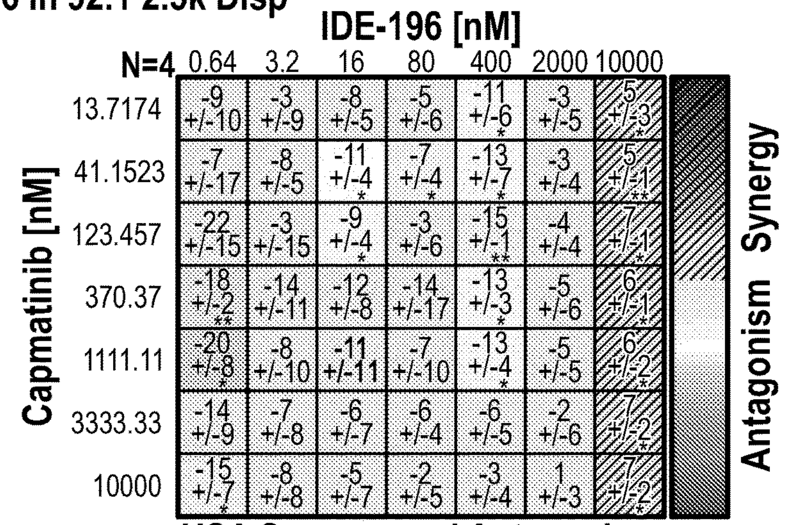
Figure 6B:
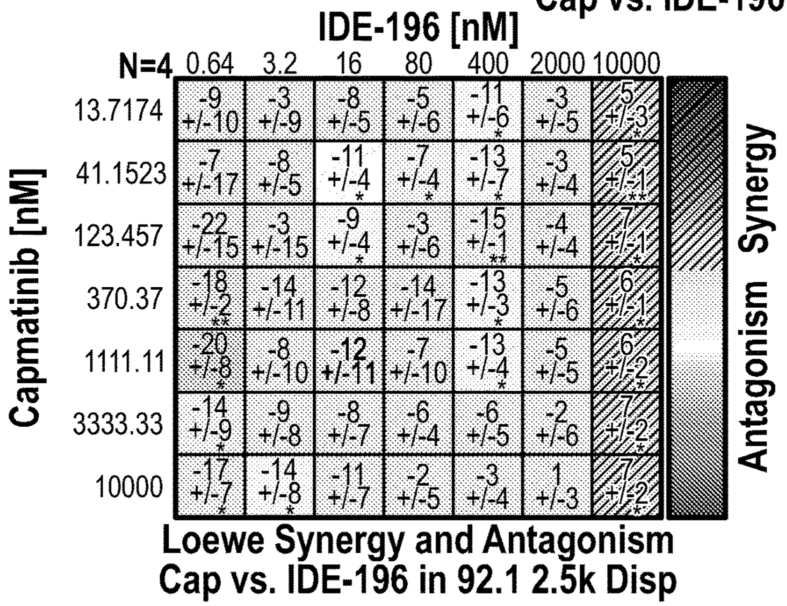
Figure 6B:
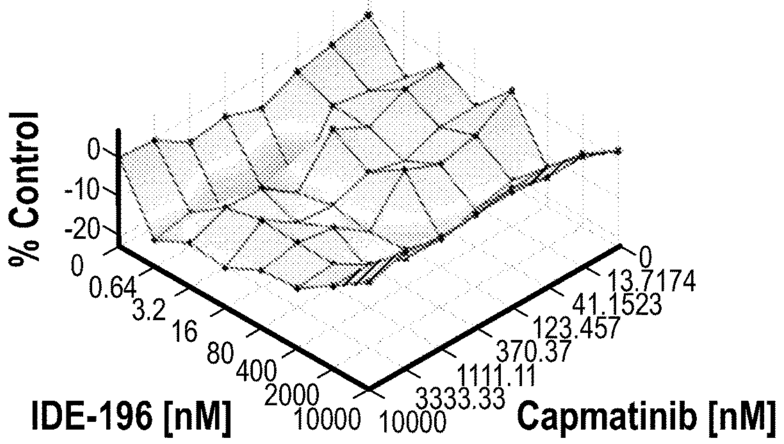
Figure 6B:
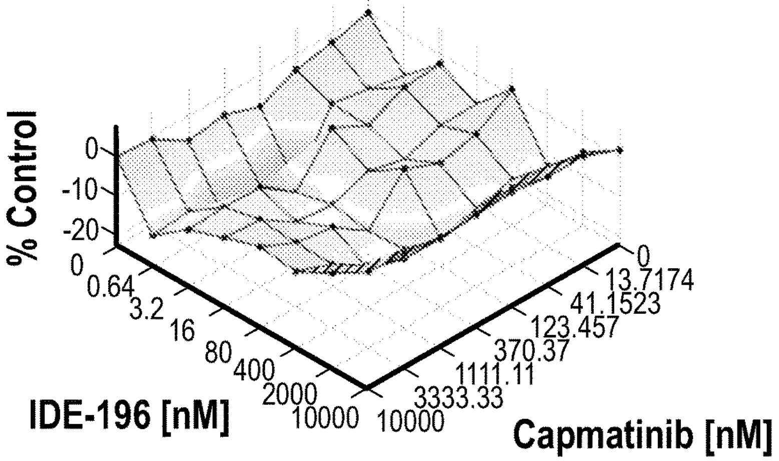
Figure 6B:
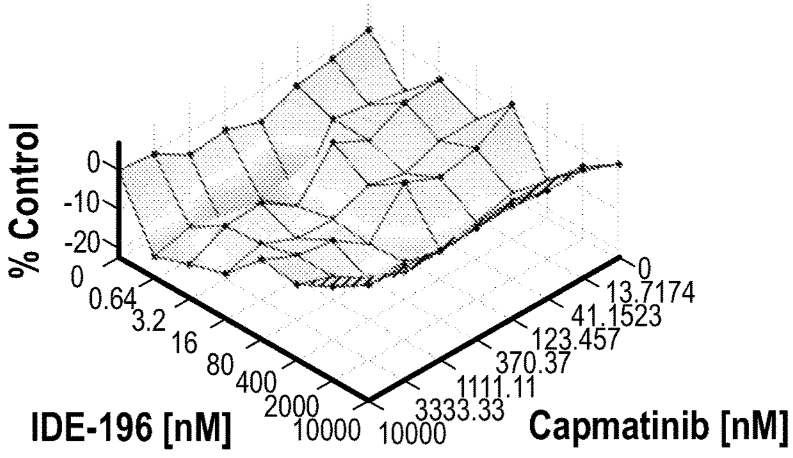
Figure 6B:
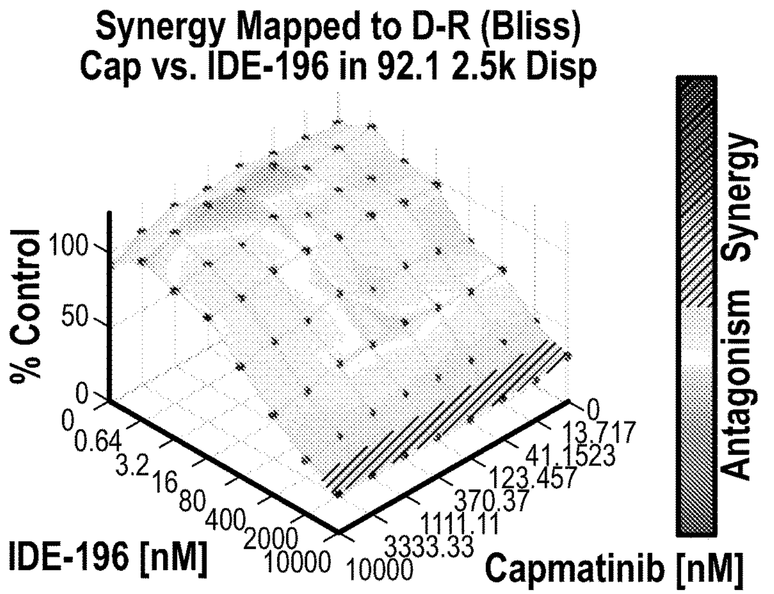
Figure 6B:
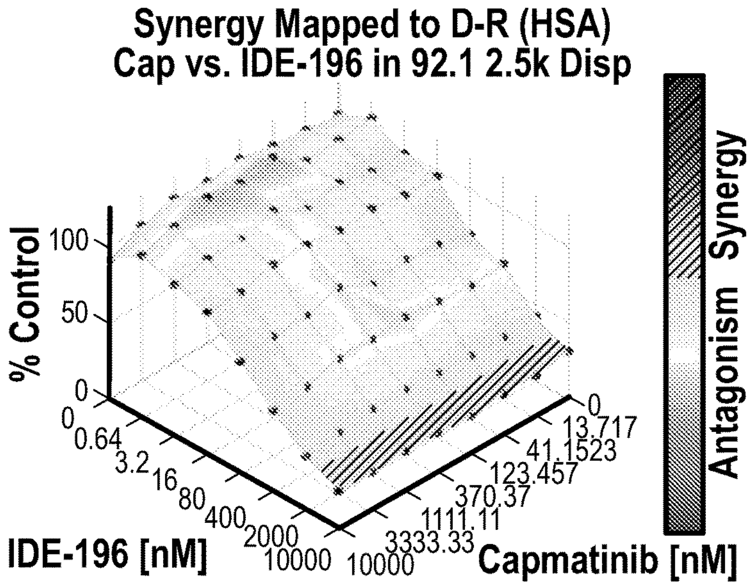
Figure 6B:
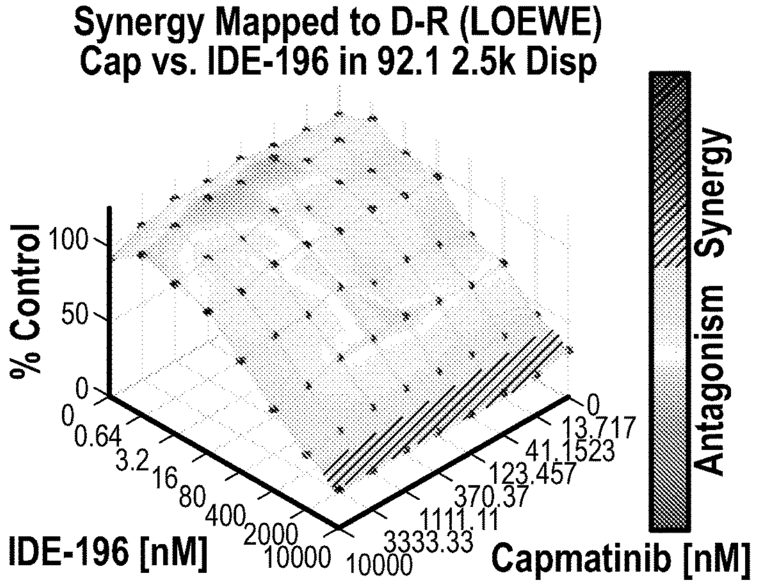
Figure 7A:
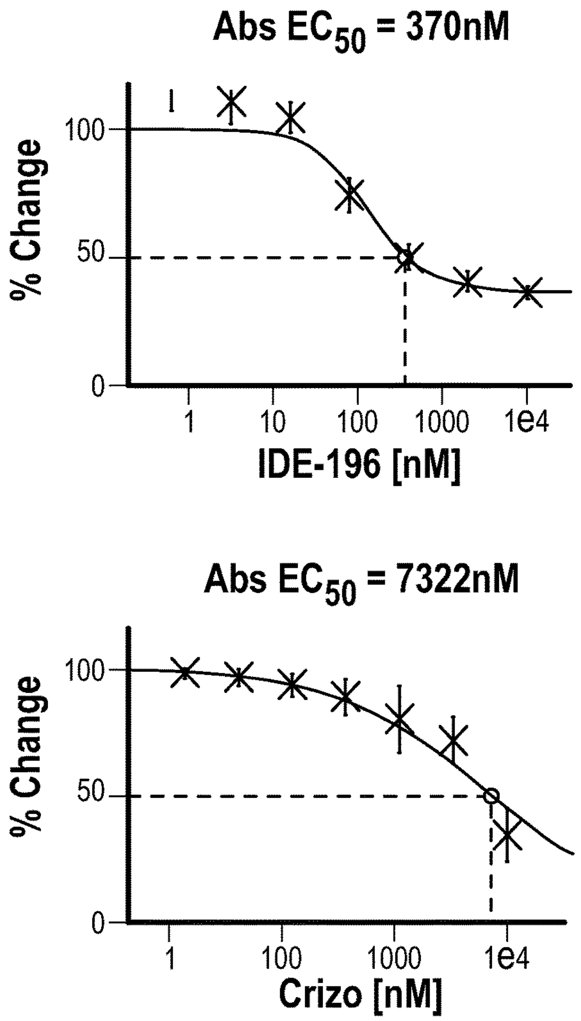
FIG. 7A provides charts illustrating the effect of a PKC inhibitor, e.g., IDE 196 (Compound A) and a cMET inhibitor (crizotinib) on the viability of MM28 metastatic uveal melanoma cells in the presence of HGF.
Figure 7A:
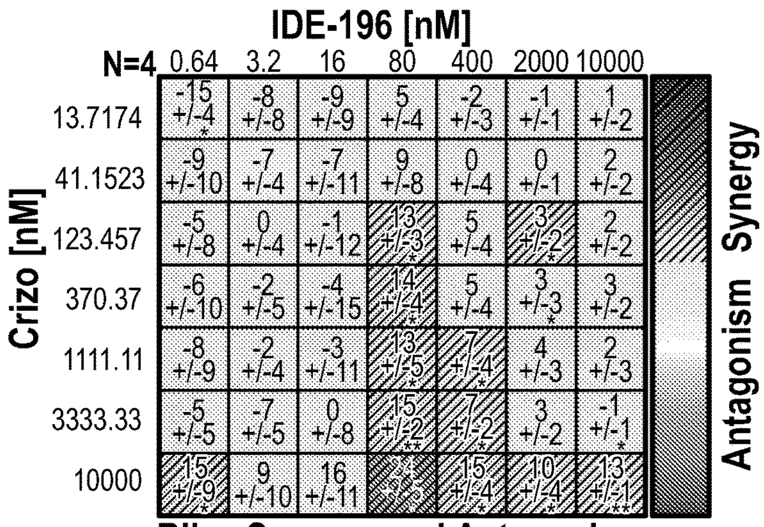
Figure 7A:
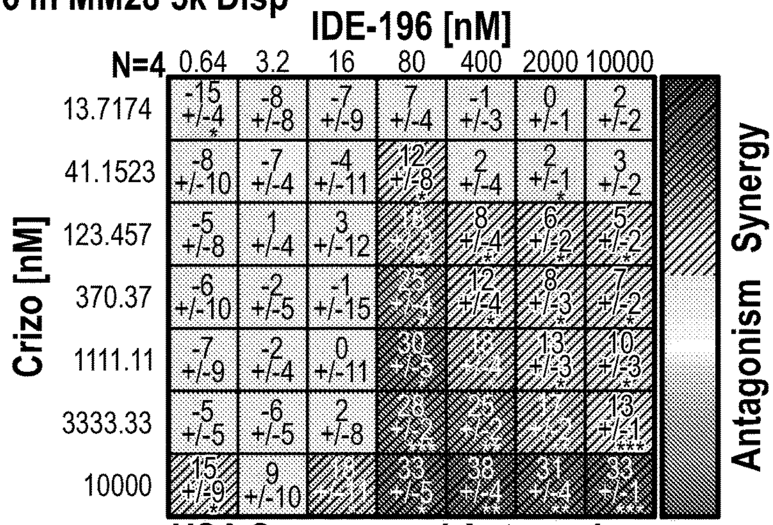
Figure 7A:
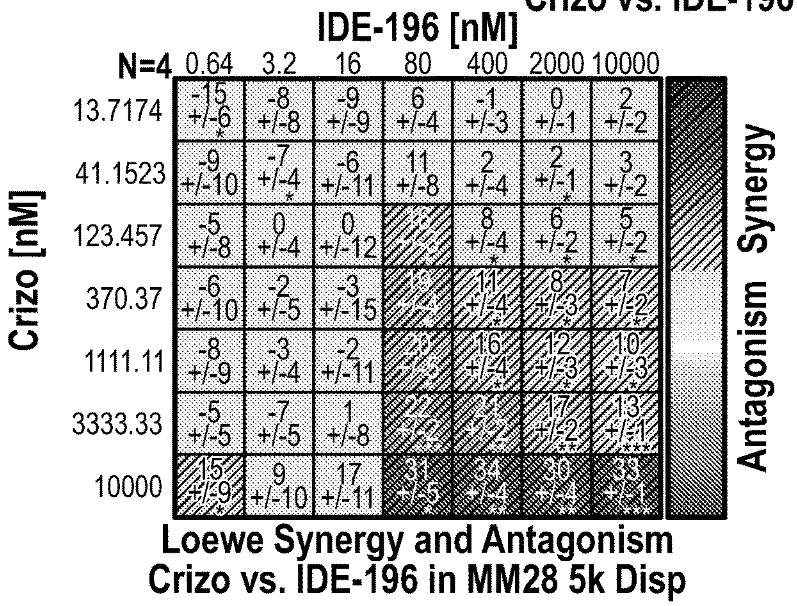
Figure 7A:
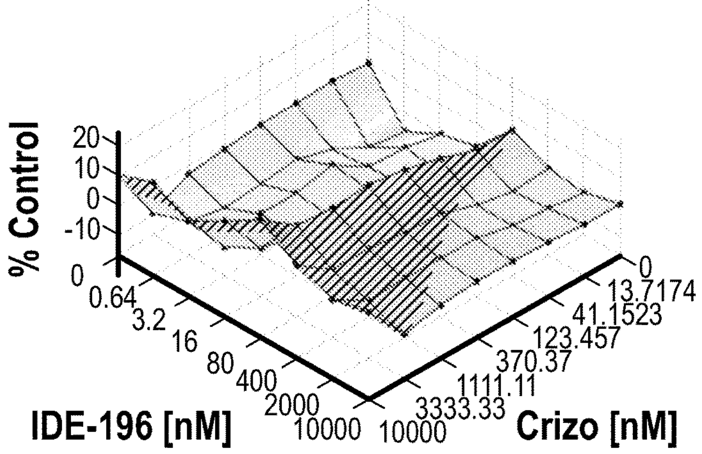
Figure 7A:
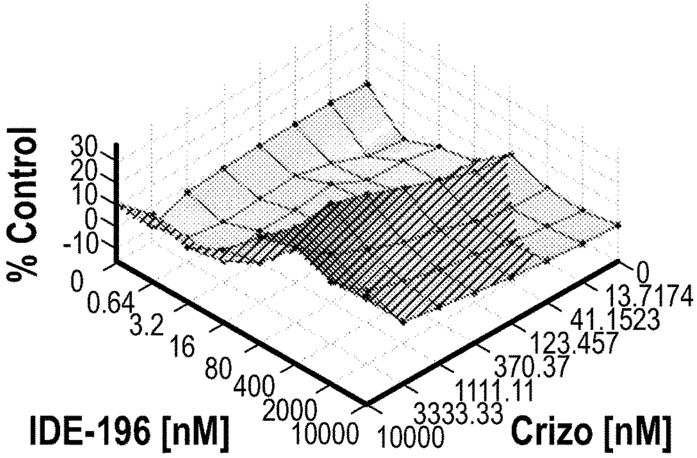
Figure 7A:
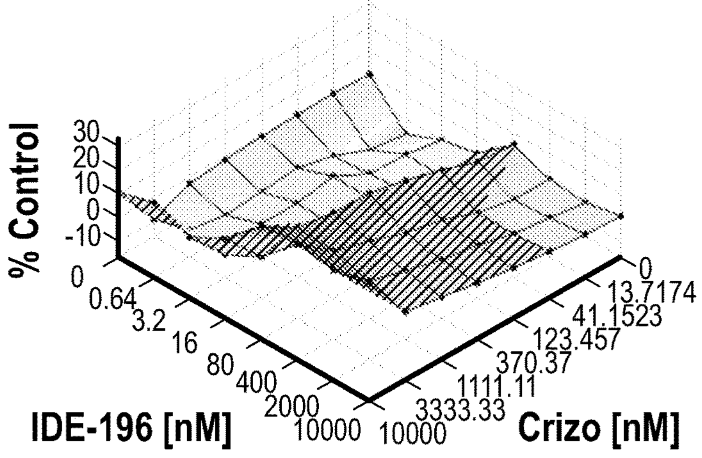
Figure 7A:
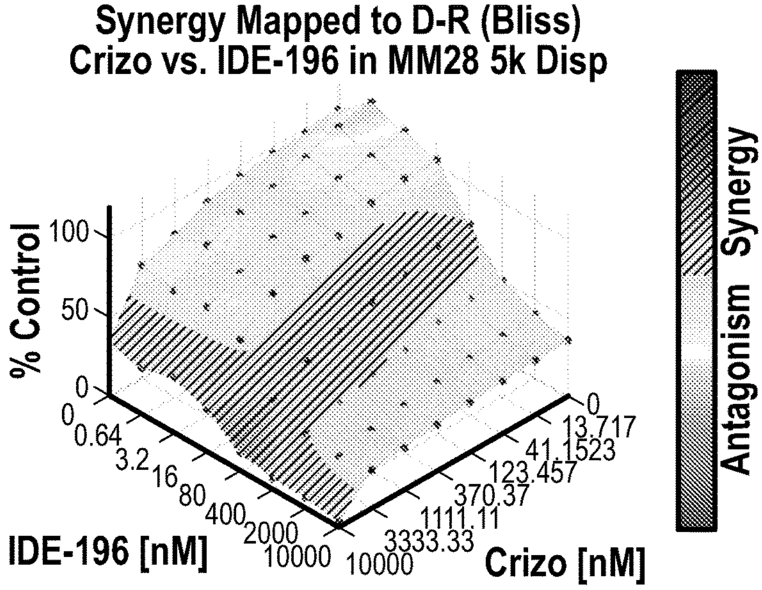
Figure 7A:
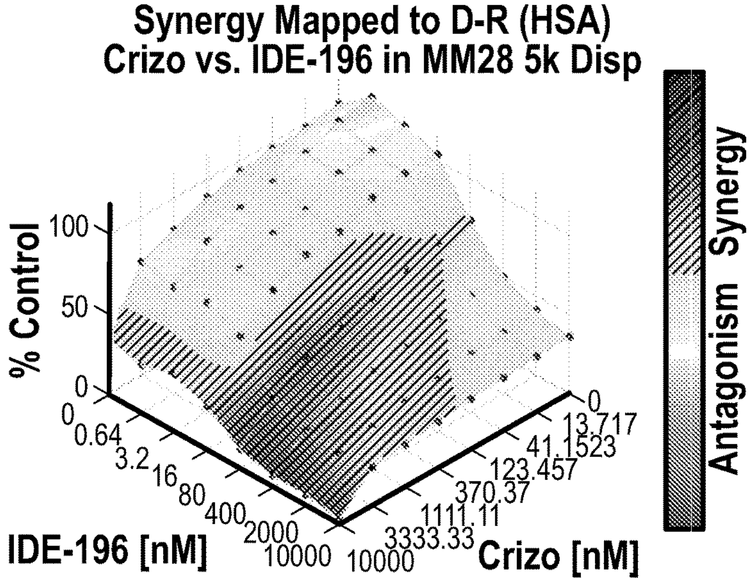
Figure 7A:
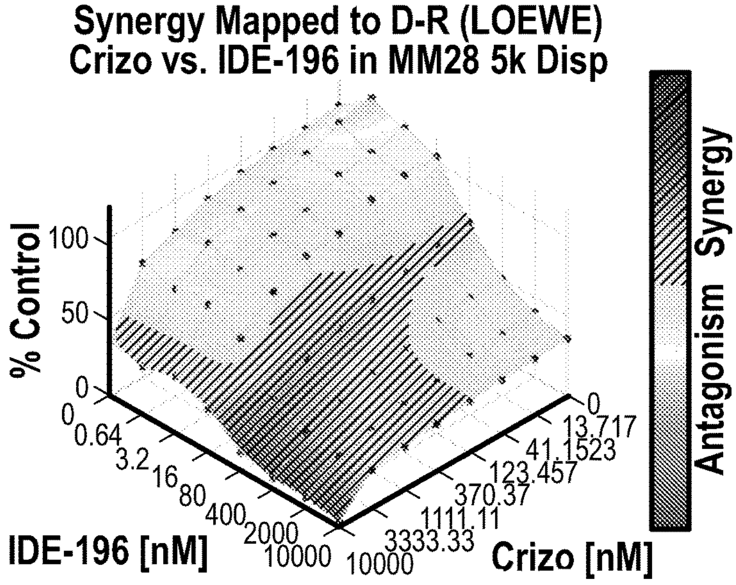
Figure 7B:
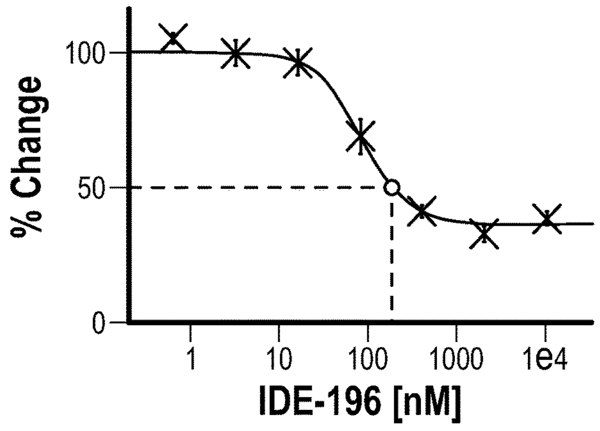
FIG. 7B provides charts illustrating the effect of a PKC inhibitor, e.g., IDE 196 (Compound A) and a cMET inhibitor (capmatinib) on the viability of MM28 metastatic uveal melanoma cells in the presence of HGF.
Figure 7B:
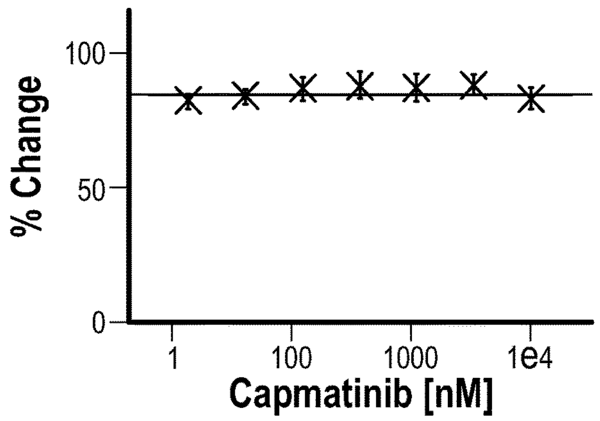
Figure 7B:
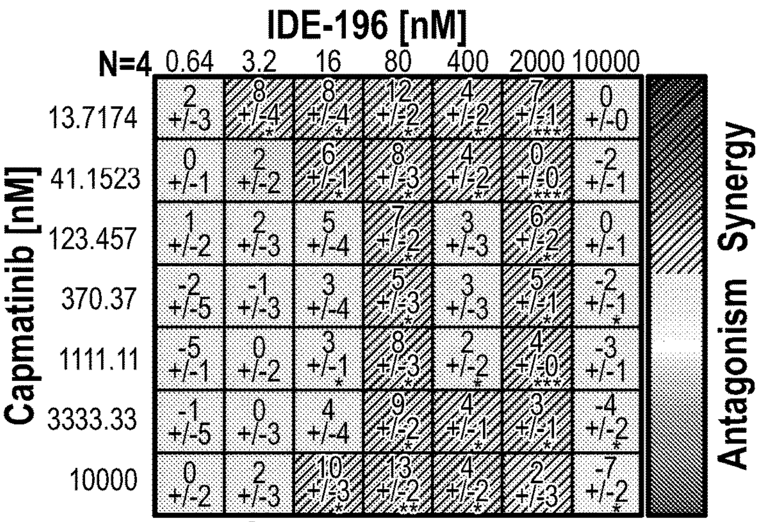
Figure 7B:
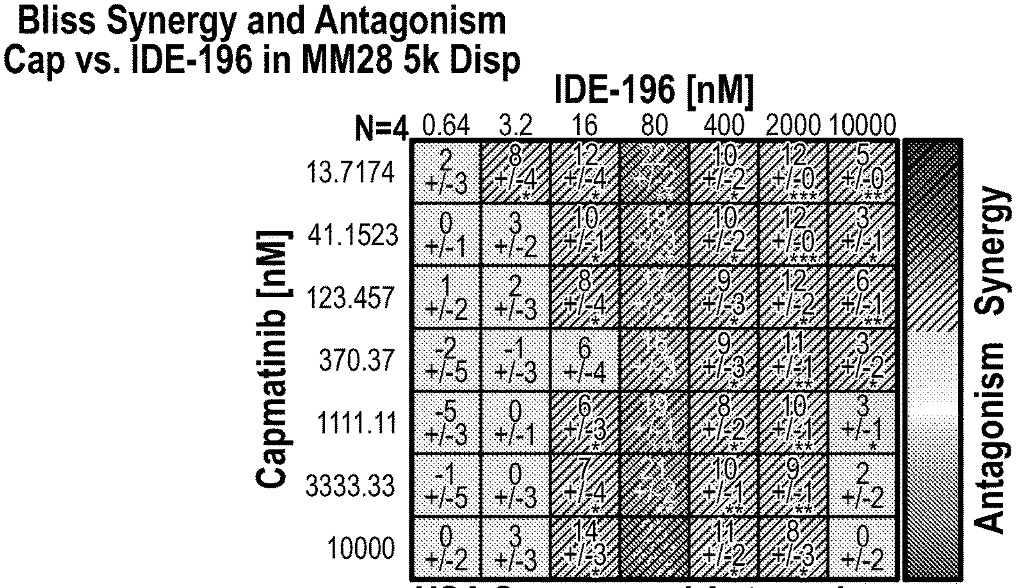
Figure 7B:
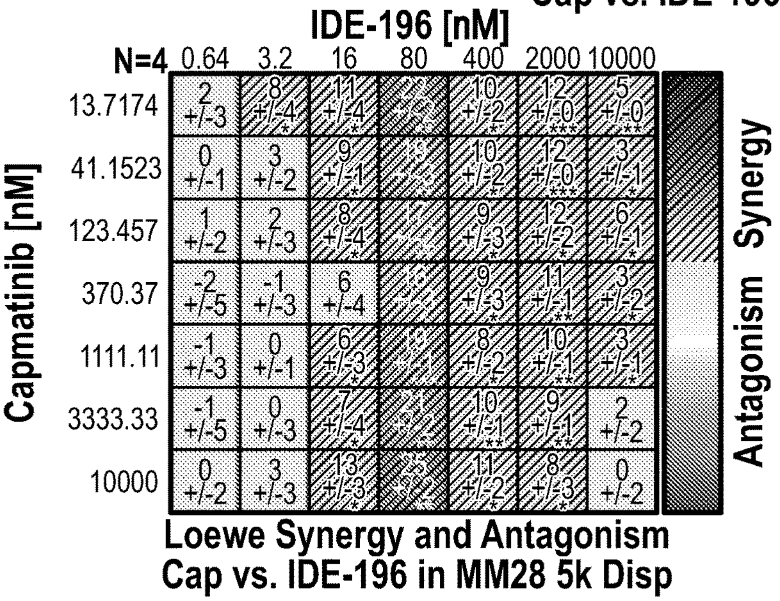
Figure 7B:
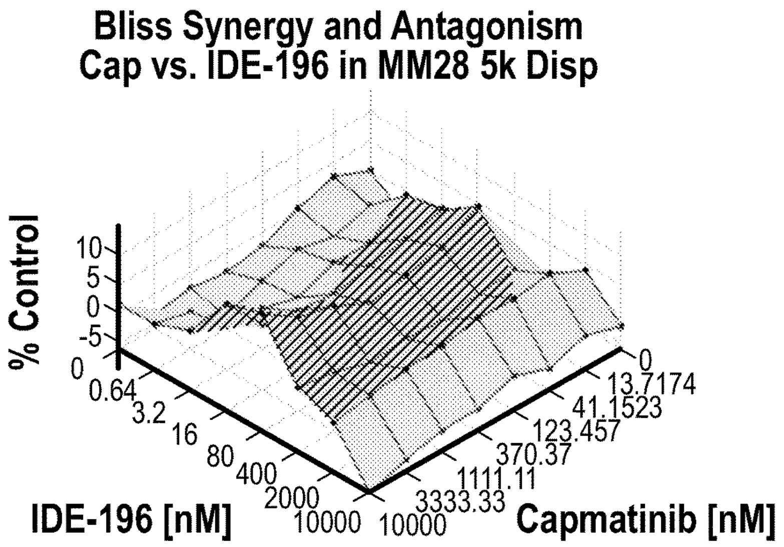
Figure 7B:
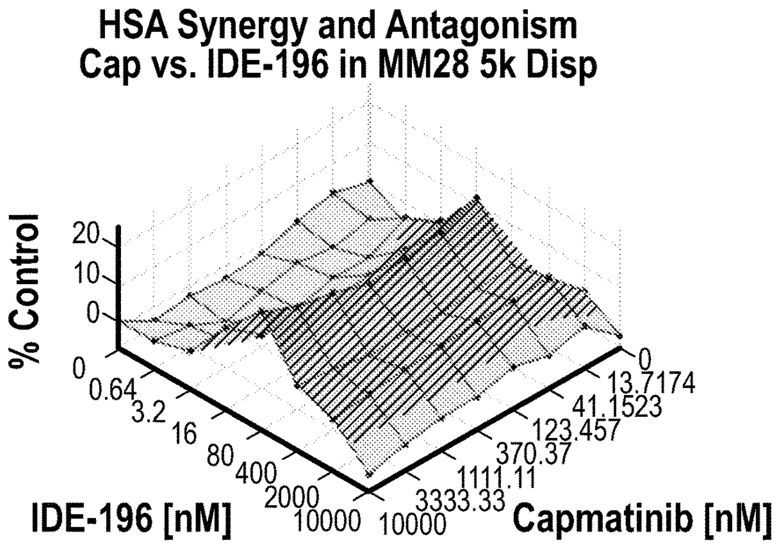
Figure 7B:
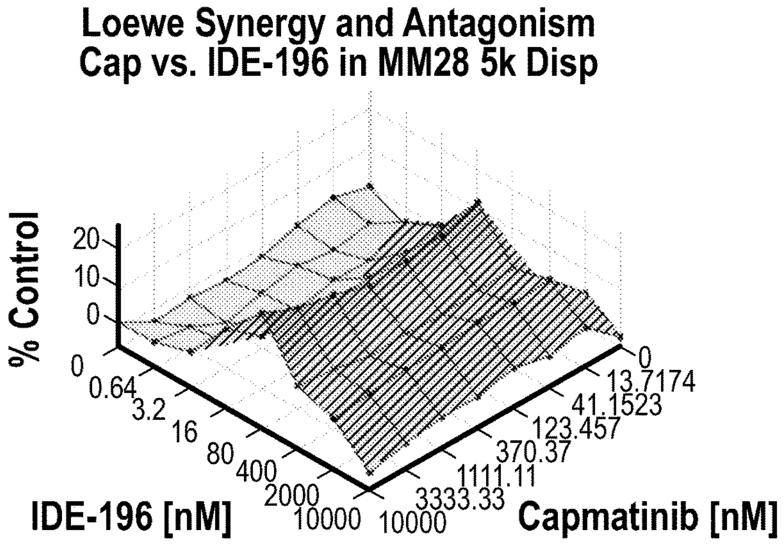
Figure 7B:
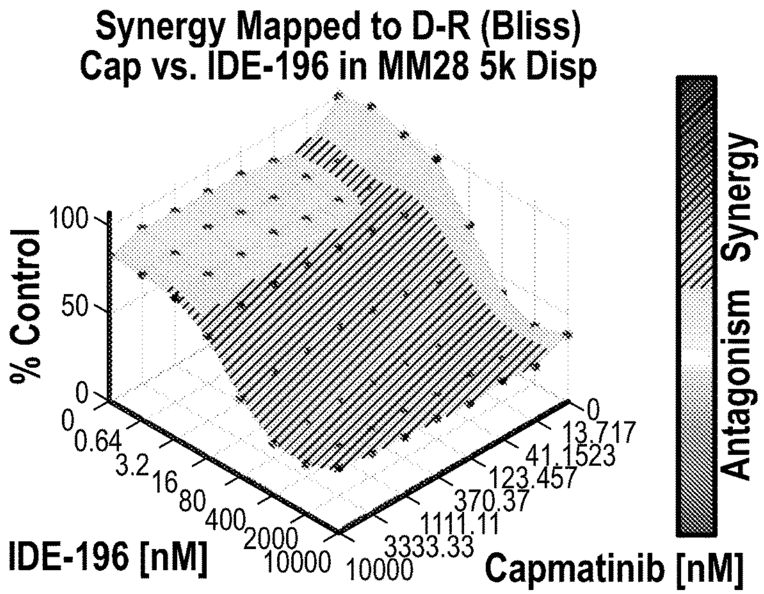
Figure 7B:
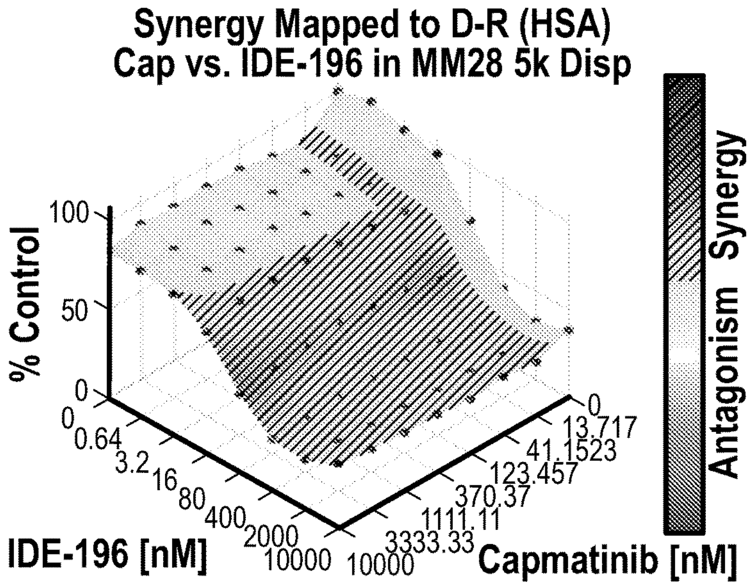
Figure 7B:
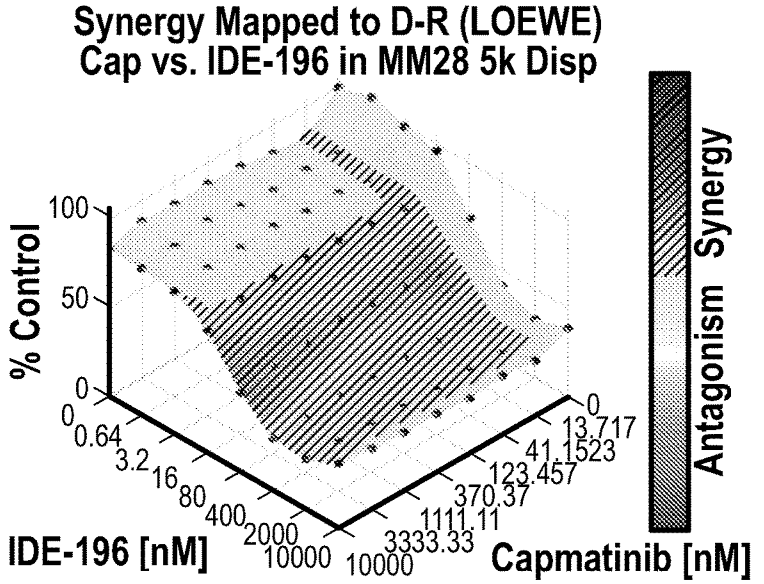

Cell viability: To evaluate the sensitivity of the uveal melanoma cell lines to the IDE196-MET inhibitor combination in the presence of HGF, cell viability changes in MEL-202, 92.1 and MM28 cells were assessed at different combinations of IDE196 with the cMET inhibitors, crizotinib and capmatinib. Combination results showed that the highest synergy was observed at concentrations of crizotinib between 41.15-370.37 nM and at IDE196 concentrations between 80-400 nM in MEL-202 cells (FIG. 5A). The capmatinib-IDE196 combination showed high synergy across all doses of capmatinib starting at doses of 80 nM IDE196 in MEL-202 (FIG. 5B). In 92.1 cells, modest synergy was observed at crizotinib concentrations from 1-3 uM and IDE196 concentrations from 0.8-10 uM (FIG. 6A). However, capmatinib and IDE196 did not synergize at any dose combination in 92.1 cells (FIG. 6B). In MM28, high synergy was observed at crizotinib concentrations from 0.123-10 uM and IDE196 concentrations from 0.8-10 uM (FIG. 7A). Capmatinib-IDE196 combination showed high synergy across all the doses in MM28 (FIG. 7B). The synergy was seen across all algorithms (HSA, Loewe and Bliss) used in the combenefit analysis.

PD analysis: HGF induced pMET, PERK levels (MAPK pathway) and pAKT and pPRAS40 (PI3K pathway) levels in MEL-202 (FIG. 5C) and MM28 (FIG. 6C). Crizotinib alone or in combination with IDE196 strongly inhibited the activation of all these analytes in these cell lines. In 92.1 cells (FIG. 7C), basal levels of pMET were low compared to MEL-202 and MM28 however a modest decrease in pERK, pAKT and pPRAS40 was observed at higher concentrations of crizotinib alone or in combination with IDE196. In the presence of HGF, IDE196 alone did not inhibit pERK even at the highest concentrations and there was no effect on pAKT or pPRAS40 in all cell lines. A dose-dependent decrease in pMARCKS or pPKCδ was observed with IDE196 alone and in combination with crizotinib in the presence of HGF. These results demonstrate that the combination of crizotinib and IDE196 inhibits HGF-induced cMET activation and signaling through MAPK and PI3K pathways. This data corresponds well with the high synergy observed in MEL-202 and MM28. In 92.1, the reduction in signaling through MAPK and PI3K pathways was modest which correlated with the modest synergy observed between crizotinib and IDE196.

Figure 5C:
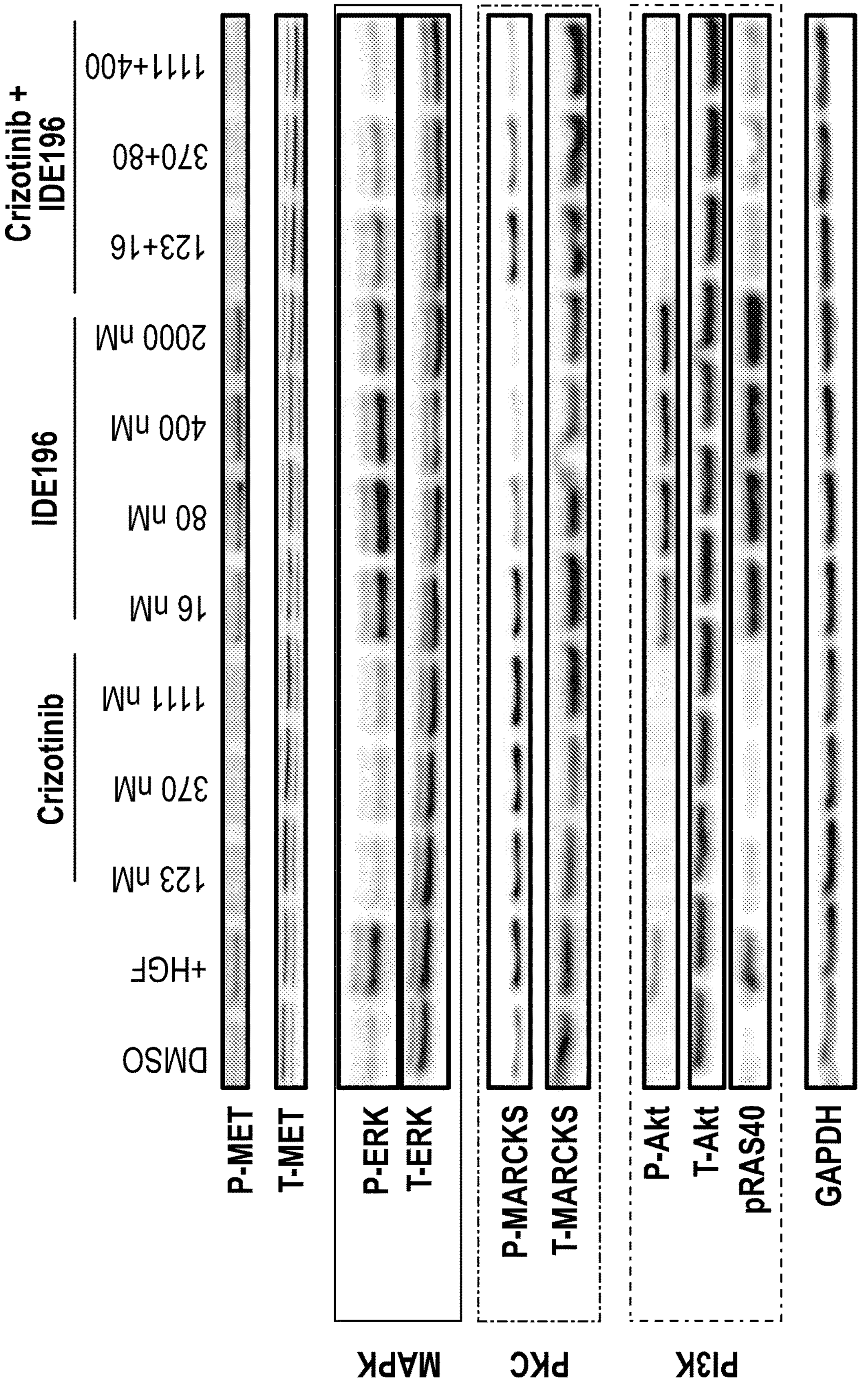
FIG. 5C provides western blots illustrating the pharmacodynamic effects of drug treatments on analytes of cMET, MAPK, PI3K and PKC signaling pathways.
Figure 6C:
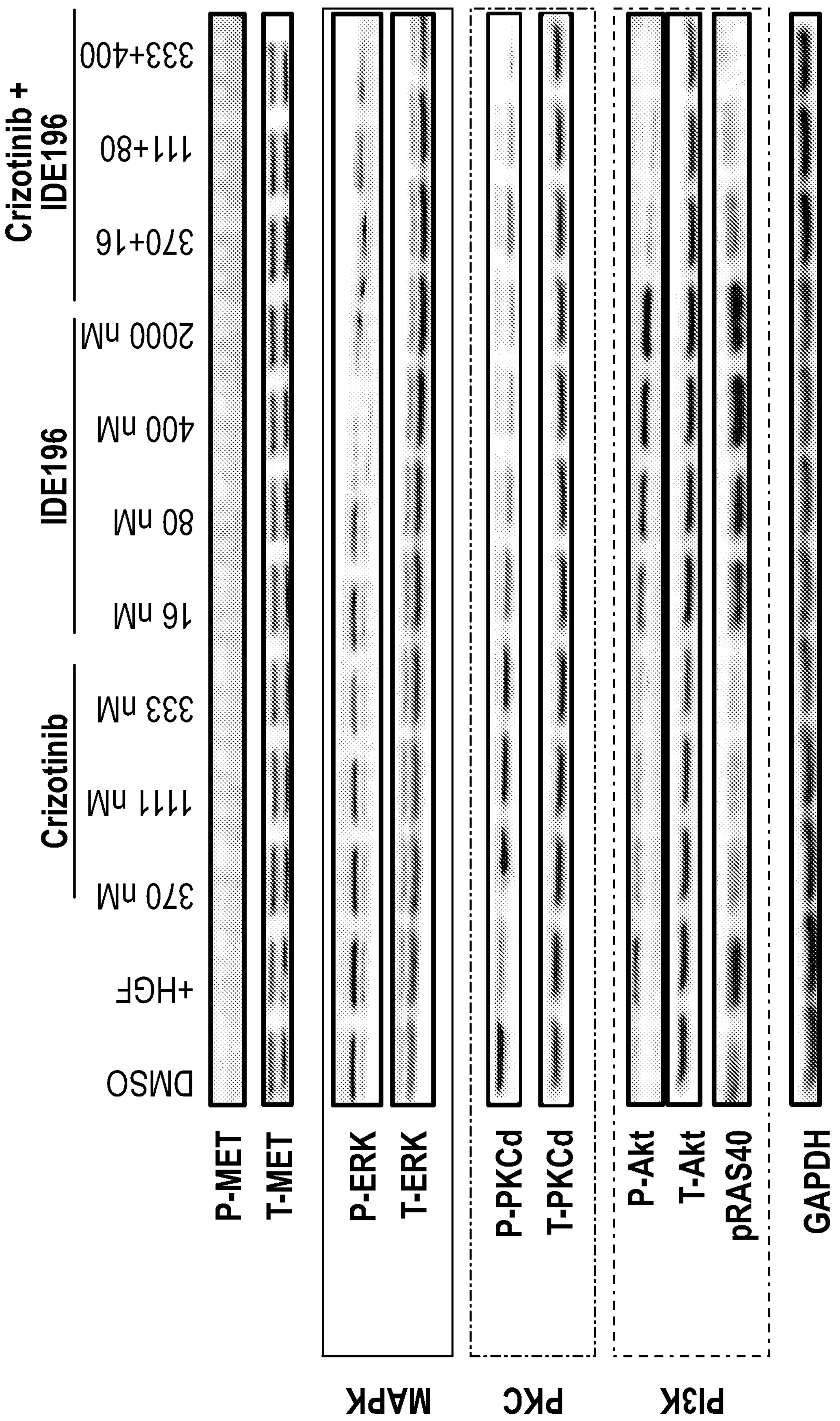
FIG. 6C provides western blots illustrating the pharmacodynamic effects of drug treatments on analytes of cMET, MAPK, PI3K and PKC signaling pathways.

FIGS. 5A, 5B and 5C, show the synergy of crizotinib/capmatinib with IDE196 on the viability of MEL-202 cells and associated PD analysis for the crizotinib-IDE196 combination. FIG. 5A shows the cytotoxic effects of IDE196 and crizotinib individually and in combination on the cell viability of MEL-202 cells (N=3). FIG. 5B shows the cytotoxic effects of IDE196 and capmatinib individually and in combination on the cell viability of MEL-202 cells (N=3). FIG. 5C shows a PD analysis showing the effects of drug treatments on analytes of cMET, MAPK, PI3K and PKC signaling pathways.

FIGS. 6A, 6B and 6C, show the extent of synergy, if any, of crizotinib/capmatinib with IDE196 on the viability of 92.1 cells and associated PD analysis for crizotinib-IDE196 combinations FIG. 6A shows the cytotoxic effects of IDE196 and crizotinib individually and in combination on the cell viability of 92.1 cells (N=3). FIG. 6B shows the cytotoxic effects of IDE196 and capmatinib individually and in combination on the cell viability of 92.1 cells (N=3). FIG. 6C shows a PD analysis showing the effects of drug treatments on analytes of cMET, MAPK, PI3K and PKC signaling pathways.

Figure 7C:
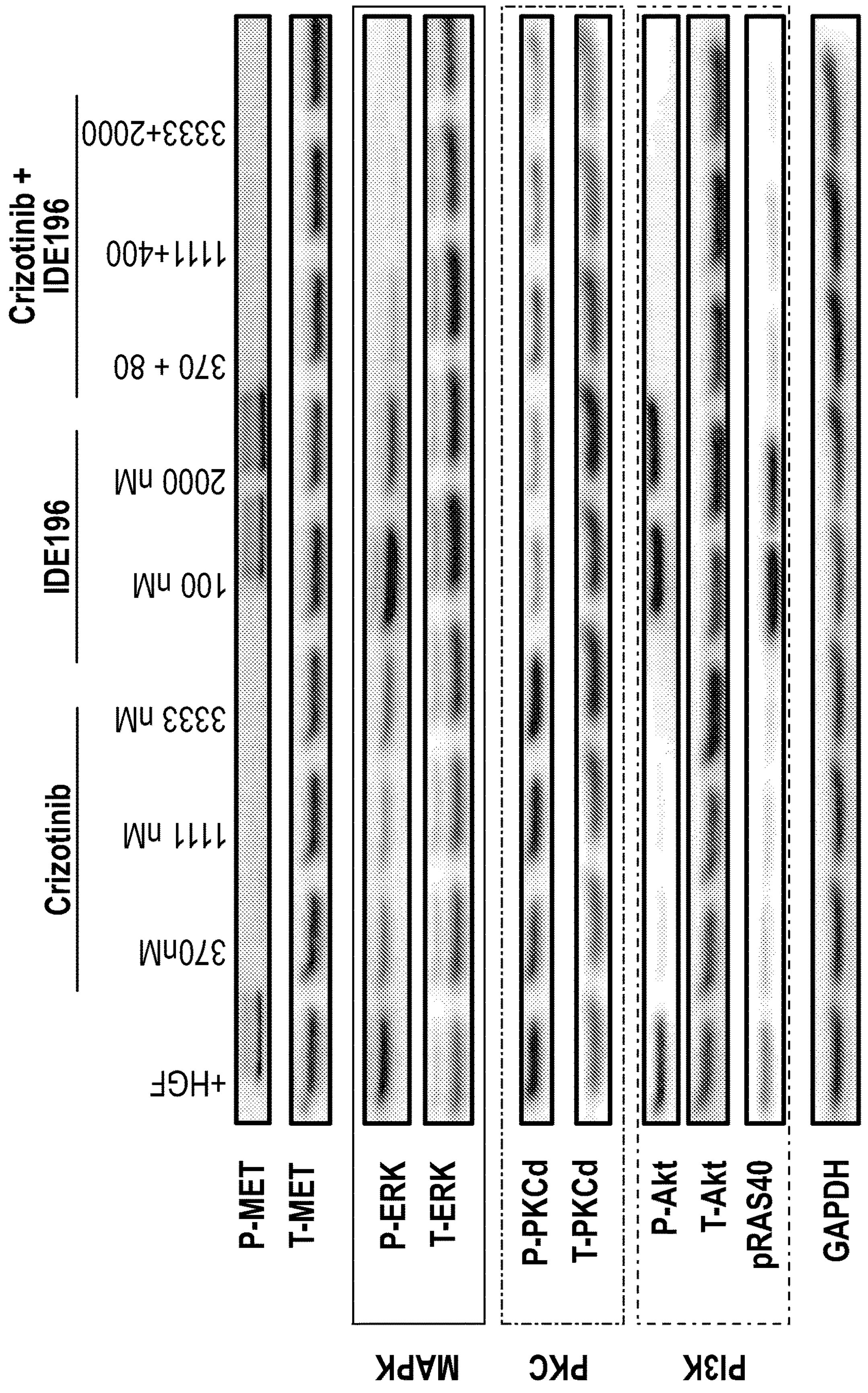
FIG. 7C provides western blots illustrating the pharmacodynamic effects of drug treatments on analytes of cMET, MAPK, PI3K and PKC signaling pathways.

FIGS. 7A, 7B and 7C, show synergy of crizotinib/capmatinib with IDE196 on the viability of MM28 cells and associated PD analysis for crizotinib-IDE196 combination. FIG. 7A shows the cytotoxic effects of IDE196 and crizotinib individually and in combination on the cell viability of MM28 cells (N=3). FIG. 7B shows the cytotoxic effects of IDE196 and capmatinib individually and in combination on the cell viability of MM28 cells (N=3). FIG. 7C shows a PD analysis showing the effects of drug treatments on analytes of cMET, MAPK, PI3K and PKC signaling pathways.

In summary, these data and various referenced figures show:

a. synergy/antagonism results (HSA, Bliss, and Loewe) for each plate in the dose matrix of Compound A and crizotinib in MEL-202 cells with HGF; a summary of cell viability data across the same matrix, and dose response curves for each of Compound A and crizotinib;

b. synergy/antagonism results (HSA, Bliss, and Loewe) for each plate in the dose matrix of Compound A and capmatinib in MEL-202 cells with HGF; a summary of cell viability data across the same matrix, and dose response curves for each of Compound A and capmatinib;

c. synergy/antagonism results (HSA, Bliss, and Loewe) for each plate in the dose matrix of Compound A and crizotinib in 92.1 cells with HGF; a summary of cell viability data across the same matrix, and dose response curves for each of Compound A and crizotinib;

d. synergy/antagonism results (HSA, Bliss, and Loewe) for each plate in the dose matrix of Compound A and capmatinib in 92.1 cells with HGF; a summary of cell viability data across the same matrix, and dose response curves for each of Compound A and capmatinib;

e. synergy/antagonism results (HSA, Bliss, and Loewe) for each plate in the dose matrix of Compound A and crizotinib in MM28 cells with HGF; a summary of cell viability data across the same matrix, and dose response curves for each of Compound A and crizotinib;

f. synergy/antagonism results (HSA, Bliss, and Loewe) for each plate in the dose matrix of Compound A and capmatinib in MM28 cells with HGF; a summary of cell viability data across the same matrix, and dose response curves for each of Compound A and capmatinib;

g. provides pharmacodynamic results for the combination of Compound A and crizotinib at varying concentrations in 92.1 (with exogenous HGF), MEL-202 (with exogenous HGF) and MM28 cells (with exogenous HGF).

Thus, these results show that the combinations of IDE 196 (Compound A) and crizotinib/capmatinib cooperate in the presence of exogenous HGF to block activation of MAPK signaling, and further block cMET, MARCKS, and PI3K signaling. Accordingly, the combination of a cMET inhibitor with a PKC inhibitor provides a synergistic anti-proliferative effect on tumor cells having elevated cMET presence.

Example 5

Evaluating cMET Presence in Uveal Melanoma Tissue Using RNA-Seq

IDE196 was clinically tested in humans in a monotherapy trial (NCT02601378). Pre- and post-dose biopsies were obtained from patients on this trial and whole transcriptome RNA-seq was performed on these biopsies to determine transcriptional changes upon treatment. To assess MET expression/activity in baseline patient samples, the RNA-seq data was aligned to GrCh38 with STAR, following which transcripts per million (TPMs) were quantified using RSEM. cMET expression was then plotted across response categories including patients with progressive disease (PD); stable disease (SD) for either < or > than 6 months or a partial response (PR). See FIG. 8A.

Figure 8B:
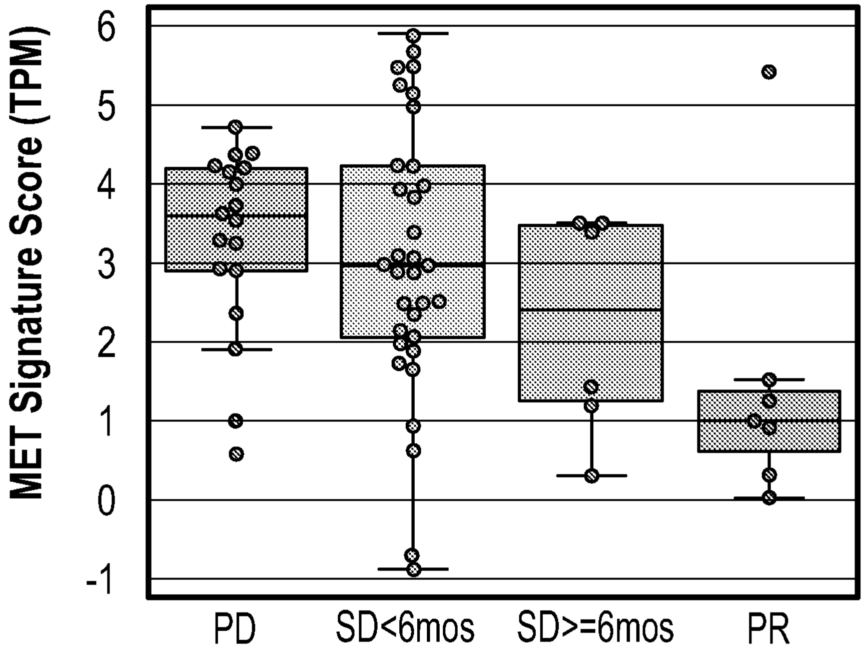

In addition to MET gene expression, a MET signature score was also applied to these samples as shown in FIG. 8B. The score was calculated from RNA expression of genes correlated with cMET. Firstly, correlations between gene-level TPMs for each gene with cMET were calculated. After examining the distribution of correlations, the genes that had the highest subset of correlations: those with a correlation with cMET>0.7 or <−0.7 were characterized as 'module' genes. Correlations between all of these module genes with one another were calculated; the module genes were then split into two modules: 1) an 'up' module which contains all module genes positively correlated with cMET, and 2) a 'down' module which contains all genes negatively correlated with cMET. The average TPMs across genes in the modules for each of the up and down modules for each patient were calculated, providing 2 averages per patient. These two averages were then subtracted (up Module-down Module) to create a single final cMET signature score, where a high positive number is indicative of relatively higher cMET signaling activity in a patient compared to the others in the cohort. To statistically test whether this score was different between response groups, an ANOVA and ordinal regression were calculated (linear regression, where for each patient, a response is assigned a number representing where on the scale of responses it falls in the appropriate order; PD=4, SD<6 mos=3, SD>6 mos=2, PR=1). The ANOVA was close to significance (p=0.052) and the ordinal regression was highly significant (p=0.0079). The box plots show that cMET expression is highest in MUM (metastatic uveal melanoma) patients, with progressive disease that did not respond to the PKC monotherapy treatment and lowest in patients who had a partial response to monotherapy treatment, i.e., PR patients. Based on this analysis, cMET activation was highest in patients with progressive disease and lowest in patients that had a partial response in this human clinical trial, substantiating the discovery that elevated cMET activation/expression is a prognostic indicator of a less favorable response to IDE196 monotherapy, for example, the patients that did not respond to PKC monotherapy generally had a MET signature score of 2 or greater, with most scores clustering around 3 to 5, e.g., around 3, 3.5, 4, and 4.5, relative to the test patient population. In contrast, patients that showed a response to PKC monotherapy, generally had scores below 2, with most scores clustering around 0 to 1.5, e.g., around 0, 0.5, 1, and 1.5, relative to the test patient population. The particular RNA transcripts that provided the MET signature score data shown in FIG. 8B correspond to the genes set forth in Table 5, below.

TABLE 5

| RNA Transcript | cMET Correlation |
|---|---|
| KIF1B | Up |
| CLCNKA | Up |
| CLIC4 | Up |
| FABP3 | Up |
| DOCK7 | Up |
| LRRC39 | Up |
| CAMSAP2 | Up |
| RASGRP3 | Up |
| AC020594.1 | Up |
| FAM98A | Up |
| ALS2CR12 | Up |
| ADAM23 | Up |
| AC010731.2 | Up |
| XRCC5 | Up |
| HTR2B | Up |
| SRD5A3 | Up |
| SLC45A2 | Up |
| LHFPL2 | Up |
| C5orf24 | Up |
| SGCD | Up |
| ATP10B | Up |
| GPNMB | Up |
| VPS41 | Up |
| SUMF2 | Up |
| MAGI2 | Up |
| LHFPL3 | Up |
| KMT2E | Up |
| SRPK2 | Up |
| MET | Up |
| CALU | Up |
| TMEM209 | Up |
| CHCHD3 | Up |
| AC021097.1 | Up |
| GPM6B | Up |
| FAM120C | Up |
| SDCBP | Up |
| RAB2A | Up |
| CHD7 | Up |
| ARFGEF1 | Up |
| PIP4P2 | Up |
| AC087439.1 | Up |
| ASAP1 | Up |
| VLDLR | Up |
| BNC2 | Up |
| STAM | Up |
| AC069542.1 | Up |
| C10orf90 | Up |
| BICD1 | Up |
| AC048344.4 | Up |
| AC026356.2 | Up |
| PLXNC1 | Up |
| GNPTAB | Up |
| NT5DC3 | Up |
| AL136418.1 | Up |
| HEATR5A | Up |
| RHOJ | Up |
| PLD4 | Up |
| AHNAK2 | Up |
| FMN1 | Up |

TABLE 5-continued

| RNA Transcript | cMET Correlation |
|---|---|
| AC090877.1 | Up |
| AC019278.1 | Up |
| ADAM10 | Up |
| MINDY2 | Up |
| PEAK1 | Up |
| IQGAP1 | Up |
| AC015818.2 | Up |
| SSH2 | Up |
| PSMD11 | Up |
| TIMP2 | Up |
| AC022966.2 | Up |
| PTPRM | Up |
| AP001029.2 | Up |
| SPIRE1 | Up |
| ANKRD30B | Up |
| RNU6-1210P | Up |
| AP006565.1 | Up |
| LINC01906 | Up |
| FGF7P1 | Up |
| AP005121.1 | Up |
| SOCS6 | Up |
| MBP | Up |
| AC018529.2 | Up |
| AC011472.3 | Up |
| KDELR3 | Up |
| SEPT3 | Up |
| SLC25A38 | Down |
| GP1BA | Down |

Example 6

Evaluating cMET Presence in Uveal Melanoma Tissue Using Immunohistochemistry (IHC)

cMET expression levels are evaluated in archival tissue specimens using CONFIRM anti-total MET (SP44) rabbit monoclonal primary antibody (Ventana Medical Systems, Inc.; cat no. 790-4430), according to the manufacturer's instructions, which can include preparing tissue samples by fixing in 10% buffered formalin, embedding in paraffin and then made into continuous 4 μm tissue sections for IHC examination. Staining is performed on a Ventana Benchmark XT instrument using CC1 standard antigen retrieval from Ventana Medical Systems (Oro Valley, AZ). Incubation with primary antibody is performed for 16 minutes at 37° C. using a 9.75 ug/mL concentration of primary antibody. Specifically bound primary antibody is detected using ultra View methodology with diaminobenzidine (Ventana Medical Systems); sections are counterstained with hematoxylin. Staining intensities are evaluated by two pathologists blinded to the diagnosis of individual patients. c-MET is localized primarily in the cytoplasm and membrane. Intensity is scored according to a four-tier systems: 0, no staining; 1+, weak; 2+, moderate; and 3+, strong. The scoring system represents composite scoring that is devised to evaluate both staining intensity (negative, weak, moderate, and strong), and the proportion of tumor cells that exhibited the respective staining intensity). Tumors with ≥50% of tumor cells exhibiting moderate to strong staining intensity are predefined as cMET-positive, prior to unblinding the treatment assignment. See, Koeppen H, Yu W, Zha J, et al. Biomarker analyses from a placebo-controlled phase II study evaluating erlotinib±onartuzumab in advanced non-small cell lung cancer: MET expression levels are predictive of patient benefit. Clin Cancer Res. 2014; 20(17): 4488-4498. doi: 10.1158/1078-0432.CCR-13-1836; Xu et al., BMC Cancer. 2015; 15:6; and Spigel et al., Clin Lung Cancer. 2012; 13(6): 500, each of which is incorporated by reference herewith in its entirety.

In a first scoring system, H-score assessment is determined by a protocol corresponding to Xu et al., BMC Cancer. 2015; 15:6, which is incorporated by reference here with in its entirety. In this scoring system, staining intensity (0-3) and the percentage of positive cells (0-100%). Each individual intensity level is multiplied by the percentage of cells and all values are added to obtain a final IHC score, ranging from 0 to 300. The final score is calculated from the scores of assessment at membranous and cytoplasmic expression. Scores for a panel of tissues from a population of patients having uveal melanoma are assessed and a median value is determined, which defines the cutoff value for elevated and non-elevated cMET. For example, in Xu et al., an H-score of 20 is determined as a cutoff for the tumor having elevated cMET presence, where the cutoff is determined by an analysis of tissue samples from representative patient population. Subsequently, scoring can be determined by comparison to representative stained tissue samples for scores of 0, 1, 2, or 3.

A second scoring system is based on a scoring criteria (positively defined as having ≥50% of tumor cells positive for membranous or cytoplasmic and/or c-Met immunostaining with moderate or strong intensity, i.e. ≥2+) adapted from Spigel et al., Clin Lung Cancer. 2012; 13 (6): 500, which is incorporated by reference here with in its entirety.

A third scoring system is based on the following table, in which "weak" staining is scaled to correspond to a prior biopsy from the same tumor site in the same patient, and elevated cMET corresponds to a score of 2 or greater. In a fourth scoring system, also based on the following table, "weak" staining corresponds to the level of staining seen in 92.1 cells, while "moderate" staining corresponds to the intensity level of staining seen in MEL-202 cells and MM28 cells, and elevated cMET corresponds to a score of 2 or greater.

TABLE 5

| IHC Score | Staining Criteria |
|---|---|
| 0 | Samples with negative or equivocal staining, or less than 50% tumor cells with weak or greater staining. |
| 1 | 50% or more tumor cells with weak or greater staining, but less than 50% tumor cells with moderate or greater staining. |
| 2 | 50% or more tumor cells with moderate or greater staining, but less than 50% tumor cells with strong or greater staining. |
| 3 | 50% or more tumor cells with strong or greater staining |

Example 7

In Vivo Evaluation of IDE196 (Compound A)—cMET Inhibitor Combination

The combination of IDE196 and crizotinib will be assessed in vivo using potentially two different humanized HGF liver orthotopic MUM models (see details below). These models enable implantation of the uveal melanoma tumor cells directly into the liver microenvironment where they form tumors which can be measured in response to drug treatments. This approach has been used for both uveal melanoma PDX models and cells lines. See Sugase et al; Kageyama et al; Cheng. In this study, orthotopic human uveal melanoma hepatic metastasis mouse models with tdTomato fluorescent protein (tdUM001 and tdUM004) and MM28 metastatic uveal melanoma cell lines will be used. The in vivo efficacy of treating with IDE196, Crizotinib as single agents and in combination will be quantified by looking at the log-fluorescent signal intensity of tumor (IVIS) and tumor size (CT scan) and in vivo tumor PD will be assessed. See Kageyama K, Ohara M, Saito K, et al. Establishment of an orthotopic patient-derived xenograft mouse model using uveal melanoma hepatic metastasis. *J Transl Med.* 2017; 15 (1): 145. Published 2017 Jun. 23. doi: 10.1186/s12967-017-1247-z; Cheng H, Terai M, Kageyama K, et al. Paracrine Effect of NRG1 and HGF Drives Resistance to MEK Inhibitors in Metastatic Uveal Melanoma. *Cancer Res.* 2015; 75 (13): 2737-2748. doi: 10.1158/0008-5472.CAN-15-0370.

Mouse Models

As murine HGF is unable to activate human MET present in the tumor cells, both mouse models exhibit elevated hHGF driven by a transgenic promoter (first model) or by the introduction of a hHGF knock-in allele (second model). The first model utilizes the hHGF-Tg SCID mouse which is homozygous for the severe combined immunodeficiency spontaneous motation (Prkdc$^{scid}$, commonly referred to as scid) and hemizygous for the hHGF-Tg transgene (Tg(Mt1-HGF)#Gvw; mouse metallothionein I promoter which drives the expression of the human HGF. These mice have elevated serum hHGF titer which is known to enhance the growth of MET expressing human tumor xenografts derived from lung, breast, kidney, colon, stomach and pancreas. See Zhang Y W, Su Y, Lanning N, et al. Enhanced growth of human met-expressing xenografts in a new strain of immunocompromised mice transgenic for human hepatocyte growth factor/scatter factor. Oncogene. 2005; 24 (1): 101-106. doi: 10.1038/sj.onc. 1208181.

The second model utilizes the NSG-hHGFki mice are NOD.scid.112Ryd$^{null}$ ("NSG") animals with the Hgf$^{tm1.1(HGF)Aveo}$ "humanized" knock-in allele (hHGFki). Mice homozygous for hHGFki express only the human form of HGF. These mice express human hepatocyte growth factor (HGF) in place of the endogenous mouse HGF as the endogenous mouse promoter drives expression of human HGF. In homozygous hHGFki mice, HGF expression from the knock-in allele is observed in developing embryo, as well as adult liver, kidney and lung See Serreze D V, Chapman H D, Post C M, Johnson E A, Suarez-Pinzon W L, Rabinovitch A. Th1 to Th2 cytokine shifts in nonobese diabetic mice: sometimes an outcome, rather than the cause, of diabetes resistance elicited by immunostimulation. *J Immunol.* 2001; 166 (2): 1352-1359; Jangphattananont N, Sato H, Imamura R, et al. Distinct Localization of Mature HGF from its Precursor Form in Developing and Repairing the Stomach *Int. J Mol Sci.* 2019; 20 (12): 2955. Published 2019 Jun. 17. doi: 10.3390/ijms20122955.

Exemplary Embodiments

The following exemplary embodiments are provided, the numbering of which is not to be construed as designating levels of importance. These exemplary embodiments provide further detail and explanation of aspects of the invention including the methods of treatment, the pharmaceutical composition products, the combination compositions and the kits.

Embodiment 1 provides a method of treatment, comprising:

- selecting a patient having metastatic uveal melanoma or having a tumor having a GNAQ or GNA11 mutation ("GNAQ/11 tumor");
- co-administering to the patient a cMET inhibitor and a protein kinase C inhibitor, wherein the protein kinase C inhibitor is represented by Formula II:

(II)

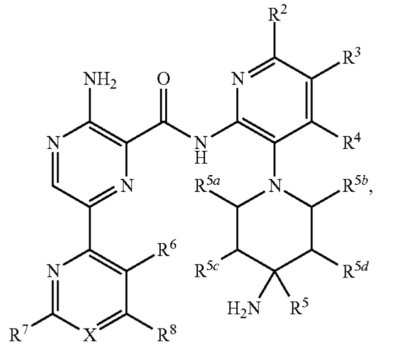

or a pharmaceutically acceptable salt thereof, wherein:

X is N or CR;

R, $R^2$, $R^3$ and $R^4$ are each independently selected from the group consisting of H, $^2$H, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2$H, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$ alkoxy (optionally substituted by one or more halogens);

$R^{5a}$ and $R^{5b}$ are each independently selected from the group consisting of H, $^2$H and $C_{1-3}$alkyl; wherein $C_{1-3}$ alkyl may optionally be substituted by one, two, three or more substituents, each independently selected from the group consisting of fluorine, hydroxyl and $C_{1-3}$alkoxy; or $R^{5a}$ and $R^{5b}$ are taken together to form a methylene or ethylene bridging group;

$R^{5c}$ and $R^{5d}$ are each independently selected from the group consisting of H, $^2$H, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2$H, halogen, $C_{1-3}$ alkyl, $C_{1-3}$alkoxy, $C_{3-7}$cycloalkyl and a 4-7 membered heterocyclyl having one, two or three heteroatoms each independently selected from the group consisting of N, O and S; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 2 provides a method of treating a patient having metastatic uveal melanoma, the method comprising:

selecting a patient with metastatic uveal melanoma having an elevated cMET presence determined by assessing a biopsy of the metastatic uveal melanoma; and co-administering to the patient a cMET inhibitor and a protein kinase C inhibitor, wherein the protein kinase C inhibitor is represented by Formula II:

(II)

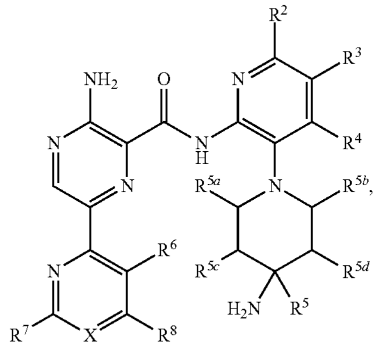

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2H$, $—CH_3$, $—CH_2F$, $—CHF_2$, $—CF_3$, $—CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$alkoxy; or $R^{5c}$ and $R^{5d}$ taken together form a methylene, ethylene or $—CH_2—O$-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 3 provides method of treating a patient having a tumor with a GNAQ or GNA11 mutation ("GNAQ/11 tumor"), the method comprising:

selecting a patient with a GNAQ/11 tumor having an elevated cMET presence determined by assessing a biopsy of the GNAQ/11 tumor; and co-administering to the patient a cMET inhibitor and a protein kinase C inhibitor, wherein the protein kinase C inhibitor is represented by Formula II:

(II)

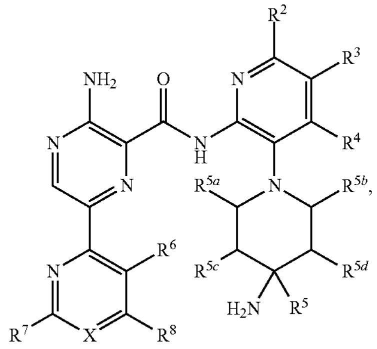

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens);

$R^5$ is selected from the group consisting of H, $^2H$, $—CH_3$, $—CH_2F$, $—CHF_2$, $—CF_3$, $—CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$alkyl; wherein $C_{1-3}$alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or $—CH_2—$O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 4 provides the method of Embodiment 1, further comprising obtaining a biopsy, or obtaining information about a biopsy, of the metastatic uveal melanoma.

Embodiment 5 provides the method Embodiment 1, further comprising obtaining a biopsy, or obtaining information about a biopsy, of the GNAQ/11 tumor.

Embodiment 6 provides the method of Embodiment 4 or 5, further comprising assessing cMET presence in the biopsy.

Embodiment 7 provides the method of Embodiment 6, further comprising selecting the patient having an elevated cMET presence as determined by assessing the biopsy.

Embodiment 8 provides the method of any one of Embodiments 2-7, further comprising obtaining the biopsy from the patient.

Embodiment 9 provides the method of any one of Embodiments 2-8, further comprising obtaining multiple biopsies, or obtaining information about cMET presence in multiple biopsies, in each case the multiple biopsies being taken at separate points of time.

Embodiment 10 provides the method of any one of Embodiments 2-9, wherein the biopsy is a tumor biopsy.

Embodiment 11 provides the method of any one of Embodiments 2-10, wherein the biopsy is a tissue biopsy, a surgical resection, or both.

Embodiment 12 provides the method of any one of Embodiments 2-11, wherein the biopsy is obtained by core needle biopsy.

Embodiment 13 provides the method of any one of Embodiments 2-12, comprising qualitatively, or quantitatively, measuring total cMET, phosphorylated cMET, non-phosphorylated cMET, or a combination thereof, in the biopsy.

Embodiment 14 provides the method of any one of Embodiments 2-13, comprising contacting an anti-cMET antibody with the biopsy.

Embodiment 15 provides the method of Embodiment 14, wherein the anti-cMET antibody is phospho-specific.

Embodiment 16 provides the method of Embodiment 14, wherein the anti-cMET antibody is not phospho-specific.

Embodiment 17 provides the method of any one of Embodiments 14-16, wherein the anti-cMET antibody detects total cMET (T-MET).

Embodiment 18 provides the method of any one of Embodiments 14-17, wherein the anti-cMET antibody is optionally labeled or includes a second reporter antibody that is capable of detecting the anti-cMET antibody.

Embodiment 19 provides the method of any one of Embodiments 2-13, comprising contacting the biopsy with a ligand for cMET.

Embodiment 20 provides the method of Embodiment 19, wherein the ligand is a ligand of an extracellular domain of cMET.

Embodiment 21 provides the method of Embodiment 19, wherein the ligand is a ligand of an intracellular domain of cMET.

Embodiment 22 provides the method of any one of Embodiments 19-21, wherein the ligand is an antibody.

Embodiment 23 provides the method of any one of Embodiments 18-22, wherein the ligand optionally carries or can be detected by a separate chromogenic, fluorescent, radiologic, or isotopic label.

Embodiment 24 provides the method of any one of Embodiments 2-23, comprising determining elevated cMET presence in the biopsy by performing ELISA, western blotting, IHC—F, IHC—P, immunocytochemistry, immunofluorescence, flow cytometry, mass cytometry, or immunoprecipitation.

Embodiment 25 provides the method of any one of Embodiments 2-24, wherein the biopsy is prepared in the form of tissue sections.

Embodiment 26 provides the method of Embodiment 25, wherein the tissue sections are fixed and paraffin-embedded.

Embodiment 27 provides the method of any one of Embodiment 2-24, wherein the biopsy is frozen.

Embodiment 28 provides the method of any one of Embodiments 2-24, wherein the biopsy is prepared in the form of isolated cells, lysed cells, homogenate, cell fraction, or a combination thereof.

Embodiment 29 provides the method of Embodiment 28, wherein the biopsy is cultured cells.

Embodiment 30 provides the method of any one of Embodiments 2-29, comprising monitoring the patient over a duration of time during which cMET presence is periodically assessed in multiple biopsies over the duration of time.

Embodiment 31 provides the method of any one of Embodiments 2-30, further comprising:

obtaining the biopsy from the patient;

determining a concentration level of cMET in the biopsy; and evaluating whether the determined level of cMET in the biopsy is equal to or greater than a predetermined level of cMET.

Embodiment 32 provides the method of any one of Embodiments 2-31, further comprising:

obtaining an initial biopsy from the metastatic uveal melanoma or the GNAQ/11 tumor of the patient and preparing a first tissue section therefrom;

obtaining a second biopsy from healthy tissue of the patient that is the same type as the tissue including the metastatic uveal melanoma or the GNAQ/11 tumor and preparing a second tissue section therefrom;

contacting an optionally labeled cMET antibody with the first tissue section;

contacting an optionally labeled cMET antibody with the second tissue section;

determining elevated cMET presence in the second tissue section compared to the first tissue section.

Embodiment 33 provides the method of any one of Embodiments 2-31, comprising:

obtaining the biopsy from the metastatic uveal melanoma or GNAQ/11 tumor of the patient and preparing a cell preparation therefrom in the form of a cell isolate, lysate, homogenate, fraction, or a combination thereof;

obtaining healthy cells of the same type and in the same form as the biopsy cell preparation;

contacting an optionally labeled cMET antibody with the biopsy cell preparation;

contacting an optionally labeled cMET antibody with the healthy cell preparation;

determining elevated cMET presence in the biopsy cell preparation compared to the healthy cell preparation.

Embodiment 34 provides the method of any one of Embodiments 2-33, comprising assessing HGF concentration in the biopsy.

Embodiment 35 provides the method of Embodiment 31 or 32 wherein the optionally labeled cMET antibody comprises a primary cMET antibody and a secondary labeled reporter antibody that binds with the primary cMET antibody.

Embodiment 36 provides the method of any one of Embodiments 2-34, wherein the biopsy has an HGF concentration of from about 0.1 ng/ml to about 1,000 ng/ml.

Embodiment 37 provides the method of any one of Embodiments 2-35, wherein the biopsy has an HGF concentration of about 1.0 ng/ml or greater.

Embodiment 38 provides the method of any one of Embodiments 1-36, comprising assessing genetic mutation in the patient.

Embodiment 39 provides the method of any one of Embodiments 1-37, comprising assessing genetic mutation in cfDNA of the patient.

Embodiment 40 provides the method of any one of Embodiments 1-38, comprising obtaining a sample containing cfDNA.

Embodiment 41 provides the method of any one of Embodiments 1-39, wherein the sample is a liquid sample.

Embodiment 42 provides the method of any one of Embodiments 1-40, wherein the liquid sample is a hematologic sample.

Embodiment 43 provides the method of any one of Embodiments 2-36, comprising assessing genetic mutation in the biopsy.

Embodiment 44 provides the method of Embodiment 37-42, wherein genetic mutation is assessed by genetic sequencing, Southern blotting, FISH, high-throughput sequencing, phage display, shotgun sequencing, PCR, or RT-PCR.

Embodiment 45 provides the method of any one of Embodiments 1 or 3-43, wherein the GNAQ or GNA11 mutation is a gain of function mutation.

Embodiment 46 provides the method of any one of Embodiments 1 or 3-44, wherein the GNAQ or GNA11 mutation is a substitution of glutamine in codon 209 (Q209), a substitution of arginine in codon 183 ($R^{183}$), or both.

Embodiment 47 provides the method of any one of Embodiments 1 or 3-45, wherein the GNAQ or GNA11 mutation is other than a substitution of glutamine in codon 209 (Q209) or other than a substitution of arginine in codon 183 ($R^{183}$), respectively.

Embodiment 48 provides the method of any one of Embodiments 1 or 3-46, wherein the GNAQ/11 tumor comprises one or more of a Q209P, Q209L, Q209H, Q209K, Q209Y, or R183Q mutation in GNAQ.

Embodiment 49 provides the method of any one of Embodiments 1 or 3-47, wherein the GNAQ/11 tumor comprises one or more of a Q209P, Q209L, Q209H, or Q209K mutation in GNA11.

Embodiment 50 provides the method of any one of Embodiments 1 or 3-48, wherein the GNAQ/11 tumor is a solid tumor.

Embodiment 51 provides the method of any one of Embodiments 1 or 3-49, wherein the GNAQ/11 tumor is pancreatic, stomach, colorectal, uterine, cervical, bladder, hepatocellular carcinoma, head and neck, prostate, breast, lung adenocarcinoma, or cutaneous melanoma.

Embodiment 52 provides the method of any one of Embodiments 1 or 3-50, wherein the GNAQ/11 tumor is pancreatic, stomach, colorectal, cervical, bladder, lung adenocarcinoma, or cutaneous melanoma.

Embodiment 53 provides the method of any one of Embodiments 1 or 3-51, wherein the GNAQ/11 tumor is cutaneous melanoma.

Embodiment 54 provides the method of any one of Embodiments 1 or 3-52, wherein the GNAQ/11 tumor is colorectal.

Embodiment 55 provides the method of any one of Embodiments 1 or 3-53, wherein the GNAQ/11 tumor is pancreatic.

Embodiment 56 provides the method of any one of Embodiments 1 or 3-54, wherein the GNAQ/11 tumor is in the liver.

Embodiment 57 provides the method of any one of Embodiments 1 or 3-55, wherein the GNAQ/11 tumor is a metastatic tumor.

Embodiment 58 provides the method of any one of Embodiments 1 or 3-56, wherein the GNAQ/11 tumor is a metastatic tumor other than metastatic uveal melanoma.

Embodiment 59 provides the method of any one of Embodiments 1 or 3-57, wherein the GNAQ/11 tumor is metastatic and metastasized to a secondary site that has an HGF concentration of from about 0.1 ng/ml to about 1,000 ng/ml.

Embodiment 60 provides the method of Embodiment 58, wherein the secondary site has an HGF concentration of about 1.0 ng/ml or greater.

Embodiment 61 provides the method of any Embodiment 58 or 59, wherein the secondary site is the liver.

Embodiment 62 provides the method of any one of Embodiments 1 or 3-49, wherein the GNAQ/11 tumor is metastatic uveal melanoma.

Embodiment 63 provides the method of any one of Embodiments 1-49 or 61, wherein the patient has uveal melanoma that is metastasized to, or at risk of metastasizing to, a secondary site that has an HGF concentration from about 0.1 ng/ml to about 1,000 ng/ml.

Embodiment 64 provides the method of Embodiment 62, wherein the secondary site has an HGF concentration of about 1.0 ng/ml or greater.

Embodiment 65 provides the method of Embodiment 62 or 63, wherein the secondary site is the liver.

Embodiment 66 provides the method of any one of Embodiments 1 or 3-55, wherein the GNAQ/11 tumor is non-metastatic.

Embodiment 67 provides the method of any one of Embodiments 1 or 3-57, wherein the GNAQ/11 tumor is a non-uveal tumor.

Embodiment 68 provides the method of any one of Embodiments 1 or 3-51, 53-57, wherein the GNAQ/11 tumor is a non-melanocytic tumor.

Embodiment 69 provides the method of any one of Embodiments 1 or 3-49, wherein in the GNAQ/11 is primary uveal melanoma.

Embodiment 70 provides the method of any one of Embodiments 1 or 3-68, wherein in the GNAQ/11 is a recurred tumor.

Embodiment 71 provides the method of any one of Embodiments 1 or 3-69, wherein the GNAQ/11 tumor lacks one or more activating mutations in BRAF, KRAS, or EGRF.

Embodiment 72 provides the method of any one of Embodiments 1 or 3-70, wherein the GNAQ/11 tumor has a low load of mutations in one or more of BAP1, SF3β1, E1F1AX, TERT, BRAF, CDKN2A, NRAS, KRAS, or EGRF.

Embodiment 73 provides the method of any one of Embodiments 1-71, wherein the protein kinase C inhibitor, the cMET inhibitor, or both, are administered to the patient without activating BRAF, KRAS, ERK, GSK3-beta, PIM 2, or EGRF.

Embodiment 74 provides the method of any one of Embodiments 2-72, wherein elevated cMET presence is relative to a predetermined level.

Embodiment 75 provides the method of any one of Embodiments 2-73, wherein elevated cMET presence is relative to a cMET presence in a healthy uveal cell, or healthy cell of the type from which the biopsy is derived, in the same patient.

Embodiment 76 provides the method of any one of Embodiments 2-73, wherein elevated cMET presence is relative to an average cMET presence in healthy uveal cells, or healthy cells of the type from which the biopsy is derived, in the patient's patient population having a tumor of the same tissue type.

Embodiment 77 provides the method of any one of Embodiments 2-73, wherein elevated cMET presence is relative to a cMET presence in a non-metastatic uveal melanoma cell, or non-metastatic GNAQ/11 tumor cell of the type from which the biopsy is derived, in the same patient.

Embodiment 78 provides the method of any one of Embodiments 2-73, wherein elevated cMET presence is relative to an average cMET presence in a non-metastatic uveal melanoma cell, or non-metastatic GNAQ/11 tumor cell of the type from which the biopsy is derived, in the patient's patient population having a tumor of the same tissue type.

Embodiment 79 provides the method of any one of Embodiments 2-77, wherein elevated cMET presence is relative to a prior assessed level of cMET presence in an earlier biopsy of the same cell type from the same patient.

Embodiment 80 provides the method of any one of Embodiments 2-78, wherein elevated cMET presence is relative to a cMET presence in a standard primary uveal melanoma cell of a primary uveal melanoma cell culture Embodiment 81 provides the method of any one of Embodiments 2-79, wherein cMET presence is elevated in the biopsy as determined by a histology score of at least 2 according to an IHC scale, or as determined by a measured cMET presence at least 25% greater relative to a cMET presence in a healthy uveal cell or healthy cell of the type from which the biopsy is derived in the same patient, relative to an average cMET presence in healthy uveal cells or healthy cells of the type from which the biopsy is derived in the patient's patient population having a tumor of the same tissue type, relative to a cMET presence in a non-metastatic uveal melanoma cell or non-metastatic GNAQ/11 tumor cell of the type from which the biopsy is derived in the same patient, relative to an average cMET presence in a non-metastatic uveal melanoma cell or non-metastatic GNAQ/11 tumor cell of the type from which the biopsy is derived in the patient's patient population having a tumor of the same tissue type, relative to a prior assessed level of cMET presence in an earlier biopsy of the same cell type from the same patient.

Embodiment 82 provides the method of any one of Embodiments 2-80, wherein cMET presence is elevated in the biopsy as determined by a histology score of at least 2 according to an IHC scale, or as determined by a measured cMET presence at least 50% greater relative to a cMET presence in a healthy uveal cell or healthy cell of the type from which the biopsy is derived in the same patient, relative to an average cMET presence in healthy uveal cells or healthy cells of the type from which the biopsy is derived in the patient's patient population having a tumor of the same tissue type, relative to a cMET presence in a non-metastatic uveal melanoma cell or non-metastatic GNAQ/11 tumor cell of the type from which the biopsy is derived in the same patient, relative to an average cMET presence in a non-metastatic uveal melanoma cell or non-metastatic GNAQ/11 tumor cell of the type from which the biopsy is derived in the patient's patient population having a tumor of the same tissue type, relative to a prior assessed level of cMET presence in an earlier biopsy of the same cell type from the same patient.

Embodiment 83 provides the method of any one of Embodiments 2-81, wherein cMET presence is elevated in the biopsy as determined by a histology score of at least 3 according to an IHC scale, or as determined by a measured cMET presence at least 100% greater relative to a cMET presence in a healthy uveal cell or healthy cell of the type from which the biopsy is derived in the same patient, relative to an average cMET presence in healthy uveal cells or healthy cells of the type from which the biopsy is derived in the patient's patient population having a tumor of the same tissue type, relative to a cMET presence in a non-metastatic uveal melanoma cell or non-metastatic GNAQ/11 tumor cell of the type from which the biopsy is derived in the same patient, relative to an average cMET presence in a non-metastatic uveal melanoma cell or non-metastatic GNAQ/11 tumor cell of the type from which the biopsy is derived in the patient's patient population having a tumor of the same tissue type, relative to a prior assessed level of cMET presence in an earlier biopsy of the same cell type from the same patient.

Embodiment 84 provides the method of any one of Embodiments 2-83, comprising determining elevated cMET presence in the biopsy by performing evaluating cMET expression using next-generation sequencing (NGS).

Embodiment 85 provides the method of any one of Embodiments 2-84, comprising determining elevated cMET presence in the biopsy by performing RNA-seq.

Embodiment 86 provides the method of any one of Embodiments 2-85, wherein elevated cMET presence is determined by measuring cMET mRNA expression levels relative to expression levels healthy uveal cell or healthy cell of the type from which the biopsy is derived in the same patient, relative to an average cMET presence in healthy uveal cells or healthy cells of the type from which the biopsy is derived in the patient's patient population having a tumor of the same tissue type.

Embodiment 87 provides the method of any one of Embodiments 2-86, wherein elevated cMET presence is determined by measuring cMET mRNA expression levels, standardized with an internal expression reference.

Embodiment 88 provides the method of Embodiment 87, wherein the internal expression reference is a house-keeping gene.

Embodiment 89 provides the method of any one of Embodiments 1, 2, or 4-88 for reducing cell proliferation of metastatic uveal melanoma.

Embodiment 90 provides the method of any one of Embodiments 1 or 3-89 for reducing cell proliferation of GNAQ/11 tumor.

Embodiment 91 provides the method of any one of Embodiments 1, 2, or 4-90 for reducing growth of metastatic uveal melanoma.

Embodiment 92 provides the method of any one of Embodiments 1 or 3-91 for reducing growth of GNAQ/11 tumor.

Embodiment 93 provides the method of any one of Embodiments 1-92 for treating metastatic disease or preventing metastatic disease progression.

Embodiment 94 provides the method of any one of Embodiments 1 or 3-93, wherein the patient has a GNAQ/11 tumor, and the protein kinase C inhibitor is administered in an amount that when taken together with the cMET inhibitor reduces proliferation, growth, or metathesis of the GNAQ/11 tumor, whereas the protein kinase C inhibitor administered at the same amount alone does not reduce proliferation, growth, or metathesis of the GNAQ/11 tumor in the patient.

Embodiment 95 provides the method of any one of Embodiments 1, 2, or 4-94, wherein the patient has metastatic uveal melanoma, and the protein kinase C inhibitor is administered in an amount that when taken together with the cMET inhibitor reduces proliferation, growth, or metathesis of the metastatic uveal melanoma, whereas the protein kinase C inhibitor administered at the same amount alone does not reduce proliferation, growth, or metathesis of the metastatic uveal melanoma in the patient.

Embodiment 96 provides the method of any one of Embodiments 1 or 3-95, wherein the patient has GNAQ/11 tumor, and the cMET inhibitor is administered in an amount that when taken together with the protein kinase C inhibitor reduces proliferation, growth, or metathesis of the GNAQ/11 tumor, whereas the cMET inhibitor administered at the same amount alone does not reduce proliferation, growth, or metathesis of the GNAQ/11 tumor in the patient.

Embodiment 97 provides the method of any one of Embodiments 1, 2, or 4-96, wherein the patient has metastatic uveal melanoma, and the cMET inhibitor is administered in an amount that when taken together with the protein kinase C inhibitor reduces proliferation, growth, or metathesis of the metastatic uveal melanoma, whereas the cMET inhibitor administered at the same amount alone does not reduce proliferation, growth, or metathesis of the metastatic uveal melanoma in the patient.

Embodiment 98 provides the method of any one of Embodiments 2-97, wherein the biopsy has elevated cMET presence, and the protein kinase C inhibitor and the cMET inhibitor are each administered to the patient in amounts that when taken together provide a therapeutic benefit whereas each agent administered at the same amount alone does not provide the therapeutic benefit.

Embodiment 99 provides the method of any one of Embodiments 1-98, wherein the PKC inhibitor and the cMET inhibitor are simultaneously administered to the patient as a single composition or separate compositions.

Embodiment 100 provides the method of any one of Embodiments 1-99, wherein the PKC inhibitor and the cMET inhibitor are administered to the patient as a single composition.

Embodiment 101 provides the method of any one of Embodiments 1-100, wherein the PKC inhibitor and the cMET inhibitor are administered to the patient at different times as separate compositions.

Embodiment 102 provides the method of Embodiment 101, wherein the PKC inhibitor and cMET inhibitor are sequentially administered, in any order, such that at least some portion of the first half-life of each inhibitor overlaps.

Embodiment 103 provides the method of Embodiment 102, wherein the PKC inhibitor is administered first, and the cMET inhibitor is administered second within the period of one half-life of the PKC inhibitor.

Embodiment 104 provides the method of Embodiment 102, wherein the cMET inhibitor is administered first, and the PKC inhibitor is administered second within the period of one half-life of the cMET inhibitor.

Embodiment 105 provides a method of treating a patient having metastatic uveal melanoma or having a tumor with a GNAQ or GNA11 mutation ("GNAQ/11 tumor"), the method comprising:

assessing cMET presence, or activity, in a biopsy of the metastatic uveal melanoma or the GNAQ/11 tumor;

if the cMET presence, or activity, is elevated in the metastatic uveal melanoma or the GNAQ/11 tumor, then co-administering to the patient a cMET inhibitor and a protein kinase C inhibitor; and if cMET presence is not elevated in the metastatic uveal melanoma or the GNAQ/11 tumor, then administering to the patient the protein kinase C inhibitor without the cMET inhibitor, wherein the protein kinase C inhibitor is represented by Formula II:

(II)

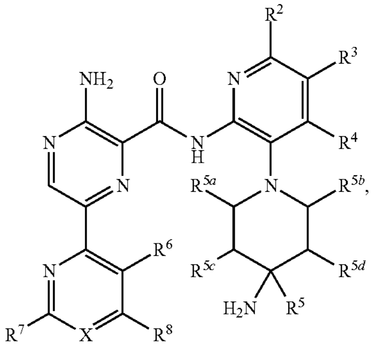

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$ alkoxy (optionally substituted by one or more halogens);

$R^{5a}$ and $R^{5b}$ are each independently selected from the group consisting of H, $^2H$ and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$alkyl, $C_1$-3alkoxy, $C_{3-7}$cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 106 provides the method of any one of Embodiments 1-105, wherein X is N and $R^2$, $R^3$ and $R^4$ are each independently H or halo.

Embodiment 107 provides the method of any one of Embodiments 1-106, wherein $R^2$, $R^3$ and $R^4$ are each H.

Embodiment 108 provides the method of any one of Embodiments 1-107, wherein $R^5$ is H or $CH_3$.

Embodiment 109 provides the method of any one of Embodiments 1-108, wherein $R^5$ is $CH_3$.

Embodiment 110 provides the method of any one of Embodiments 1-109, wherein $R^6$ and $R^7$ are each independently selected from H, halo, $C_{1-3}$ haloalkyl, $C_{1-3}$ haloalkoxy, $C_{3-7}$ cycloalkyl, morpholino, piperidinyl and piperazinyl.

Embodiment 111 provides the method of any one of Embodiments 1-110, wherein one of $R^6$ and R is $C_{1-3}$ haloalkyl, $C_{1-3}$ haloalkoxy, $C_{3-7}$ cycloalkyl, morpholino, piperidinyl and piperazinyl, and one of $R^6$ and $R^7$ is H.

Embodiment 112 provides the method of any one of Embodiments 1-111, wherein one of $R^6$ and $R^7$ is trifluoromethyl or trifluoromethoxy and one of $R^6$ and R is H.

Embodiment 113 provides the method of any one of Embodiments 1-112, wherein $R^{5a}$, $R^{5b}$, $R^{5c}$ and $R^{5d}$ are each H.

Embodiment 114 provides the method of any one of Embodiments 1-113, wherein the protein kinase C inhibitor is:

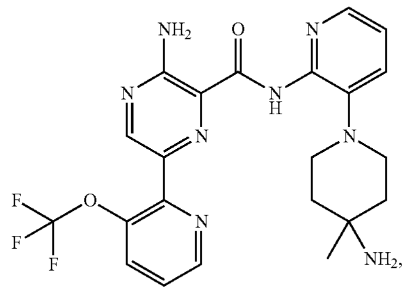

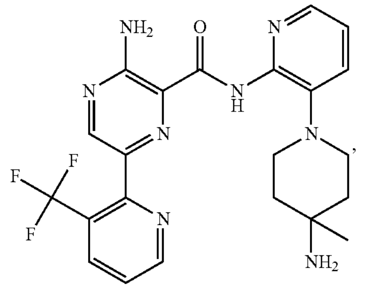 [SMILES: CC1(N)CCN(c2cccnc2NC(=O)c2nc(-c3ncccc3C(F)(F)F)cnc2N)CC1]

or

-continued

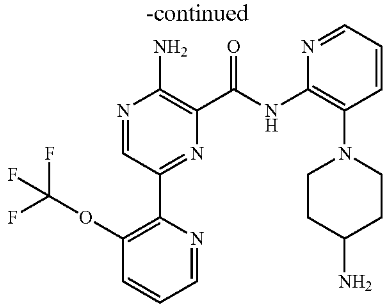

or a pharmaceutically acceptable salt thereof.

Embodiment 115 provides the method of any one of Embodiments 1-114, wherein the protein kinase C inhibitor is:

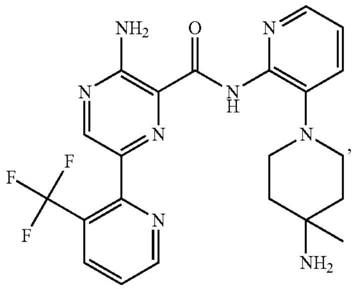

or a pharmaceutically acceptable salt thereof.

Embodiment 116 provides the method of any one of Embodiments 1-115, wherein the cMET inhibitor is an inhibitor of intracellular ATP-cMET ligand-receptor binding.

Embodiment 117 provides the method of any one of Embodiments 1-116, wherein the cMET inhibitor is an ATP-competitive small molecule cMET inhibitor.

Embodiment 118 provides the method of any one of Embodiments 1-117, wherein the cMET inhibitor is selected from the group consisting of crizotinib, capmatinib, cabozantinib, tivantinib, and any combination thereof.

Embodiment 119 provides the method of any one of Embodiments 1-118, wherein the cMET inhibitor is capmatinib.

Embodiment 120 provides the method of any one of Embodiments 1-118, wherein the cMET inhibitor also has activity as an ALK inhibitor, a RAS1 inhibitor, or both.

Embodiment 121 provides the method of any one of Embodiments 1-118, wherein the cMET inhibitor is crizotinib.

Embodiment 122 provides the method of any one of Embodiments 1-121, wherein the protein kinase C inhibitor is administered at a dose of from about 100 mg to about 1000 mg daily.

Embodiment 123 provides the method of any one of Embodiments 1-122, wherein the protein kinase C inhibitor is administered at a dose of from about 10 mg to about 400 mg βID.

Embodiment 124 provides the method of any one of Embodiments 1-123, wherein the protein kinase C inhibitor is administered at a dose of about 50 mg βID, 100 mg βID, 150 mg βID, 200 mg βID, 250 mg βID, 300 mg βID, 350 mg βID, or 400 mg βID.

Embodiment 125 provides the method of any one of Embodiments 1-124, wherein the protein kinase C inhibitor is administered according to a dosing regimen comprising a dosing cycle comprising a first dosing series, followed by a second dosing series, wherein:

(a) the first dosing series comprises a dose of about 200 mg βID of compound (I), or a pharmaceutically acceptable salt thereof, and (b) the second dosing series comprises a dose of about 400 mg βID of compound (I), or a pharmaceutically acceptable salt thereof.

Embodiment 126 provides the method of Embodiment 125, wherein the length of the first dosing series is 5 to 10 days, and the length of the second dosing series is 18 to 23 days; and the length of first dosing cycle comprising first dosing series and second dosing series is 28 days.

Embodiment 127 provides a pharmaceutical product comprising a protein kinase C inhibitor, a cMET inhibitor, and a pharmaceutically-acceptable carrier, wherein the protein kinase C inhibitor is represented by Formula II:

(II)

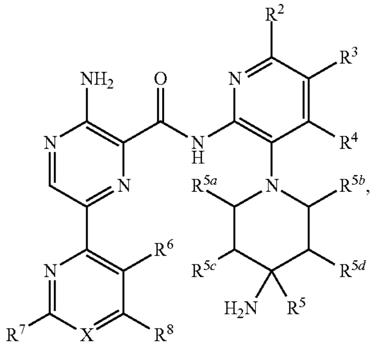

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group; $R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 128 provides the pharmaceutical product of Embodiment 127, wherein the protein kinase C inhibitor and the cMET inhibitor are formulated together in a single unit dosage form comprising the pharmaceutically-acceptable carrier.

Embodiment 129 provides the pharmaceutical product of Embodiment 128, wherein the protein kinase C inhibitor and the cMET inhibitor are formulated into two separate unit dosage forms, each having a pharmaceutically-acceptable carrier.

Embodiment 130 provides a kit comprising:

a protein kinase C inhibitor and a cMET inhibitor, which are formulated together, or separately, into one or more pharmaceutical compositions, each of which comprises a pharmaceutically-acceptable carrier; and instructions for using the protein kinase C inhibitor and the cMET inhibitor together in a combination therapy, wherein the protein kinase C inhibitor is represented by Formula II:

(II)

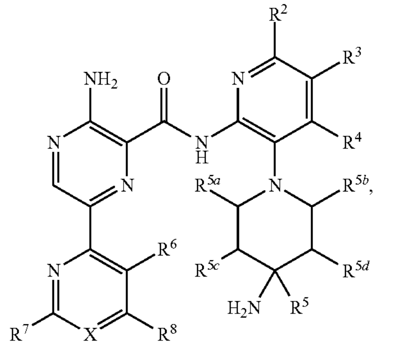

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$alkoxy may optionally be substituted by one, two, three or more halogens; and wherein $C_{1-3}$alkyl may optionally be substituted by one, two, three or more substituents, each independently selected from the group consisting of hydroxyl, halogen and $C_{1-3}$alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$alkyl, $C_1$-3alkoxy, $C_{3-7}$cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens Embodiment 131 provides a kit comprising:

a pharmaceutical composition comprising a protein kinase C inhibitor and a pharmaceutically-acceptable carrier; and a probe, or reference standard, for assessing cMET presence, wherein the protein kinase C inhibitor is represented by Formula II:

(II)

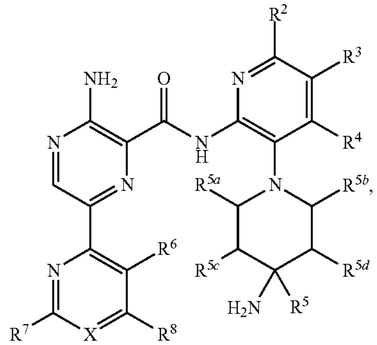

or a pharmaceutically acceptable salt thereof, wherein:

X is N or CR;

R, $R^2$, $R^3$ and $R^4$ are each independently selected from the group consisting of H, $^2H$, halogen, hydroxyl, $C_{1-3}$ alkoxy and $C_{1-3}$ alkyl; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens);

$R^5$ is selected from the group consisting of H, $^2H$, —$CH_3$, —$CH_2F$, —$CHF_2$, —$CF_3$, —$CH_2OH$ and $C_{2-3}$ alkyl; wherein $C_{2-3}$ alkyl may optionally be substituted by one, two, three or more substituents, each independently selected from the group consisting of fluorine, hydroxyl and $C_{1-3}$alkoxy (optionally substituted by one or more halogens);

$R^{5a}$ and $R^{5b}$ are each independently selected from the group consisting of H, $^2H$ and $C_{1-3}$alkyl; wherein $C_{1-3}$ alkyl may optionally be substituted by one, two, three or more substituents, each independently selected from the group consisting of fluorine, hydroxyl and $C_{1-3}$ alkoxy; or $R^{5a}$ and $R^{5b}$ are taken together to form a methylene or ethylene bridging group;

$R^{5c}$ and $R^{5d}$ are each independently selected from the group consisting of H, $^2H$, fluorine, hydroxyl, $C_{1-3}$ alkoxy and $C_{1-3}$ alkyl; wherein $C_{1-3}$ alkyl may optionally be substituted by one, two, three or more substituents, each independently selected from the group consisting of fluorine, hydroxyl and $C_{1-3}$ alkoxy; or $R^{5c}$ and $R^{5d}$ taken together form a methylene, ethylene or —$CH_2$—O-bridging group;

$R^6$, $R^7$ and $R^8$ are each independently selected from the group consisting of H, $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; wherein $C_{1-3}$ alkoxy may optionally be substituted by one, two, three or more halogens; and wherein $C_{1-3}$ alkyl may optionally be substituted by one, two, three or more substituents, each independently selected from the group consisting of hydroxyl, halogen and $C_{1-3}$ alkoxy (optionally substituted by one or more halogens); or wherein $R^6$ and $R^8$ optionally forms a partially unsaturated carbobicyclic or heterobicyclic ring with the heteroaryl ring to which they are attached, wherein the carbobicyclic or heterobicyclic ring may optionally be substituted by one, two or three groups, each independently selected from the group consisting of $^2H$, halogen, $C_{1-3}$ alkyl, $C_{1-3}$ alkoxy, $C_{3-7}$ cycloalkyl and a 4-7 membered heterocyclyl having one, two or three heteroatoms each independently selected from the group consisting of N, O and S; and wherein $C_{1-3}$ alkyl and $C_{1-3}$ alkoxy may optionally be substituted by one, two, three or more halogens.

Embodiment 132 provides the method, pharmaceutical product, or kit, of any one of Embodiments 1-131, wherein the protein kinase C inhibitor has least a 1000 fold greater inhibitory activity against protein kinase C isoform delta, epsilon, eta, or theta than against kinases outside the protein kinase C kinome.

Embodiment 133 provides the method, pharmaceutical product, or kit, of any one of Embodiments 1-131, wherein the protein kinase C inhibitor has at least a 1000 fold lower inhibitory activity against GSK3-beta than against protein kinase C isoform theta.

Embodiment 134 provides the method, pharmaceutical product, or kit, of any one of Embodiments 1-131, wherein the protein kinase C inhibitor has greater inhibitory activity against each of protein kinase C isoform delta, epsilon, eta, and theta than against protein kinase C isoform alpha, beta 1, beta 2, or gamma.

Embodiment 135 provides the method, pharmaceutical product, or kit, of any one of Embodiments 1-131, wherein the protein kinase C inhibitor exhibits at least a 5 fold lower inhibitory activity against protein kinase C isoforms alpha, beta 1, beta 2, or gamma than against protein kinase C isoform delta, epsilon, eta, or theta.

Embodiment 136 provides the method, pharmaceutical product, or kit, of any one of Embodiments 1-131, wherein the protein kinase C inhibitor exhibits at least a 20 fold lower inhibitory activity against protein kinase C isoform beta 1 than against protein kinase C isoform theta.

Embodiment 137 provides the method, pharmaceutical product, or kit, of any one of Embodiments 1-131, wherein the protein kinase C inhibitor has an $IC_{50}$ of less than 50 nM for one or more of protein kinase C isoforms delta, epsilon, eta, and theta.

Embodiment 138 provides the method, pharmaceutical product, or kit, of any one of Embodiments 1-131, wherein the protein kinase C inhibitor has an $IC_{50}$ of less than 5 nM with respect to one or more of protein kinase C isoforms delta, epsilon, eta, and theta.

Embodiment 139 provides the method, pharmaceutical product, or kit, of any one of Embodiments 1-131, wherein the protein kinase C inhibitor has an $IC_{50}$ of greater than 50 nM with respect to protein kinase C isoforms beta 1, beta 2, or both.

Embodiment 140 provides the method, pharmaceutical product, or kit, of any one of Embodiments 1-131, wherein the protein kinase C inhibitor has an $IC_{50}$ of greater than 5,000 nM with respect to PIM 2, GSK3β, or both.

Embodiment 141 provides the method of Embodiment 85, wherein performing RNA-Seq involves assessing a MET signature score based on calculating RNA expression from one or more genes correlated with cMET.

Embodiment 142 provides the method of Embodiment 141, wherein elevated cMET presence is determined by measuring a patient's MET signature score relative to MET signature scores in the patient's patient population.

Embodiment 143 provides the method of Embodiment 142, wherein the MET signature scores in the patient's patient population are ranked according to response group, preferably such that a score of 4=progressive disease, 3=stable disease for less than 6 months, 2=stable disease ≥6 months, and 1=partial response to monotherapy, and the patient's MET signature score is 2 or greater, 3 or greater, or around 3, 3.5, 4, or 4.5.

Embodiment 144 provides the pharmaceutical product, or kit, of any one of Embodiments 127-140 for use in treating a patient having metastatic uveal melanoma, for use in treating a tumor with a GNAQ or GNA11 mutation ("GNAQ/11 tumor"), or both.

Embodiment 145 provides the pharmaceutical product, or kit, of any one of Embodiments 127-140 for use in the method of any one of Embodiments 1-126 or 141-143.

Embodiment 146 provides the use of the cMET inhibitor and the protein kinase C inhibitor, or the pharmaceutical product of Embodiment 127-129, for the manufacture of a medicament for treating a patient according to the method of any one of Embodiments 1-126 or 141-143.

Embodiment 147 provides a method, pharmaceutical product, or kit of any one or combination of the preceding Embodiments, optionally configured such that any or all elements or options recited therein are available to use or select from.

SUMMARY STATEMENTS

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The invention has been described broadly and generically herein. Each of the narrower species and subgeneric groupings falling within the generic disclosure also form part of the invention. This includes the generic description of the invention with a proviso or negative limitation removing any patient matter from the genus, regardless of whether or not the excised material is specifically recited herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

All patents, publications, scientific articles, web sites and other documents and material references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

All references cited herein are incorporated herein by reference as if fully set forth herein in their entirety.

What is claimed is:

1. A method of treating metastatic uveal melanoma in a patient in need thereof, comprising:

co-administering to the patient crizotinib; and a protein kinase C inhibitor represented by:

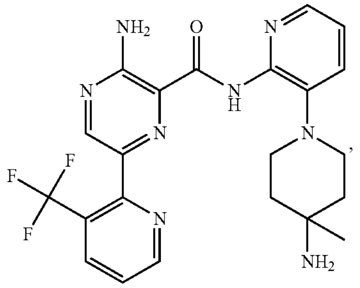 [SMILES: CC1(N)CCN(c2cccnc2NC(=O)c2nc(-c3ncccc3C(F)(F)F)cnc2N)CC1]

or a pharmaceutically acceptable salt thereof.

2. The method of claim 1, wherein the protein kinase C inhibitor is:

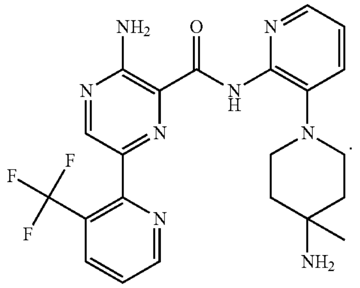 [SMILES: CC1(N)CCN(c2cccnc2NC(=O)c2nc(-c3ncccc3C(F)(F)F)cnc2N)CC1]

3. A method of treating metastatic uveal melanoma in a patient in need thereof, comprising:

administering to the patient crizotinib; and administering to the patient a compound represented by:

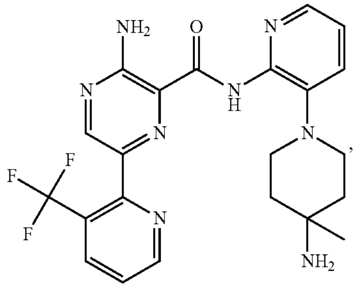 [SMILES: CC1(N)CCN(c2cccnc2NC(=O)c2nc(-c3ncccc3C(F)(F)F)cnc2N)CC1]

thereby treating the metastatic uveal melanoma.

4. The method of claim 3, wherein the crizotinib and the compound are administered to the patient simultaneously.

5. The method of claim 3, wherein the crizotinib and the compound are administered to the patient sequentially.

6. The method of claim 3, wherein the crizotinib and the compound are administered to the patient as separate compositions.

7. The method of claim 6, wherein crizotinib and the compound are each administered orally.

* * * * *